(12) United States Patent
Martial et al.

(10) Patent No.: US 7,655,626 B2
(45) Date of Patent: Feb. 2, 2010

(54) ANTIANGIOGENIC PEPTIDES

(75) Inventors: Joseph Martial, Modave (BE); Ingrid Struman, Boncelles (BE); Ngoc-Quynh-Nhu Nguyen, Ans (BE); Robert Brasseur, Haillot (BE); Laurence Lins, Vieusart (BE)

(73) Assignees: Universite de Liege, Angleur (BE); Faculte Universitaire des Sciences Agronomiques de Gembloux, Gembloux (BE)

( * ) Notice: Subject to any disclaimer, the term of this patent is extended or adjusted under 35 U.S.C. 154(b) by 18 days.

(21) Appl. No.: 11/573,660

(22) PCT Filed: Aug. 11, 2005

(86) PCT No.: PCT/EP2005/053952

§ 371 (c)(1),
(2), (4) Date: May 2, 2007

(87) PCT Pub. No.: WO2006/018418

PCT Pub. Date: Feb. 23, 2006

(65) Prior Publication Data

US 2008/0039384 A1    Feb. 14, 2008

(30) Foreign Application Priority Data

Aug. 16, 2004   (EP) .................. 04103920

(51) Int. Cl.
*A61K 38/00* (2006.01)
*A61K 38/10* (2006.01)
*A61K 38/22* (2006.01)
*C07K 14/47* (2006.01)

(52) U.S. Cl. .............. 514/12; 514/2; 514/14; 514/44; 514/327; 530/324; 530/326

(58) Field of Classification Search ............ None
See application file for complete search history.

(56) References Cited

FOREIGN PATENT DOCUMENTS

EP       1 378 515 A1    1/2004
WO       WO 98/51323     11/1998
WO       WO 2006/018418 A2   2/2006

OTHER PUBLICATIONS

Brasseur et al., 1997, TIBS, vol. 22, pp. 167-171.*
Nguyen et al., 2006, PNAS, vol. 103, No. 39, pp. 14319-14324.*
Kinet et al., "Characterization of Lactogen Receptor-binding Site 1 of Human Prolactin" *The Journal of Biological Chemistry* 271(24): 14353-14360 (1996).
Bushell, G. et al. (1993) "Evidence supporting a role for cathepsin B in the generation of T cell antigenic epitopes of human growth hormone" *Molecular Immunology* 30: 587-591.
Dings, R.P.M. et al. (2003) "Discovery and development of anti-angiogenic peptides: a structural link" *Angiogenesis* 6:83-91.
Lins, L. et al (2001) "Computational study of lipid-destabilizing protein fragments: towards a comprehensive view of tilted peptides" *Structure, Function and Genetics* 44:435-447.
Piossek, C. et al. (1999) "Vascular endothelial growth factor (VEGF) receptor II-derived peptides Inhibit VEGF" *The Journal of Biological Chemistry* 274:5612-5619.

* cited by examiner

*Primary Examiner*—Robert Landsman
*Assistant Examiner*—Ian Dang
(74) *Attorney, Agent, or Firm*—Knobbe Martens Olson & Bear LLP

(57) ABSTRACT

The present invention refers to a pharmaceutical composition comprising an isolated antiangiogenic peptide or a recombinant protein comprising the antiangiogenic peptide, wherein the peptide is between 11 and 40 amino acids in length and having antiangiogenic activity, the peptide comprising the amino acid sequence: X1-X2-X3-X4-X5-X6-X7-X8-X9-X10-X11-X12-X13-X14, wherein X1 is any amino acid residue compatible with forming a helix; X2 is an amino acid residue of: Leu, Ile, Val; X3 is an amino acid residue of: Arg, Lys, His, Ser, Thr; X4 is an amino acid residue of: Ile, Leu, Val; X5 is any amino acid residue compatible with forming a helix; X6 is an amino acid residue of: Leu, Ile, Val; X7 is an amino acid residue of: Leu, Ile, Val, Ser, Thr; X8 is any amino acid residue compatible with forming a helix; X9 is any amino acid residue compatible with forming a helix; X10 is an amino acid residue of: Gln, Glu, Asp, Arg, His, Lys, Asn; X11 is an amino acid residue of: Ser, Thr; X12 is an amino acid residue of: Trp, Tyr, Phe; X13 is an amino acid residue of: Leu, Ile, Val, Asn, Gln; X14 is an amino acid residue of: Glu, Gln, Asp, Asn.

12 Claims, 18 Drawing Sheets

A.

LPICPGGAARCQVTLRDLFDRAVVLSHYIHNLSSEMFSEFDKRYTHGRGF

ITKAINSCHTSSLATPEDKEQAQQMNQKDFLSLIVSILRSWNEPLYHLVT

EVRGMQEAPEAILSKAVEIEEQTKRLLEGMELIVSQVHPETKENEIYPVW

SGLPSLQMADEESRLSAYYNLLHCLRRDSHKIDNYLKLLKCRIIHNNNC

B.

```
hPRL     FLSLIVSILRSWNE    (SEQ ID NO: 3)
hGH      LLRISLLLIQSWLE    (SEQ ID NO: 1)
hGH-v    LLRISLLLIQSWLE    (SEQ ID NO: 1)
hPL      LLRISLLLIESWLE    (SEQ ID NO: 2)
```

Fig. 1

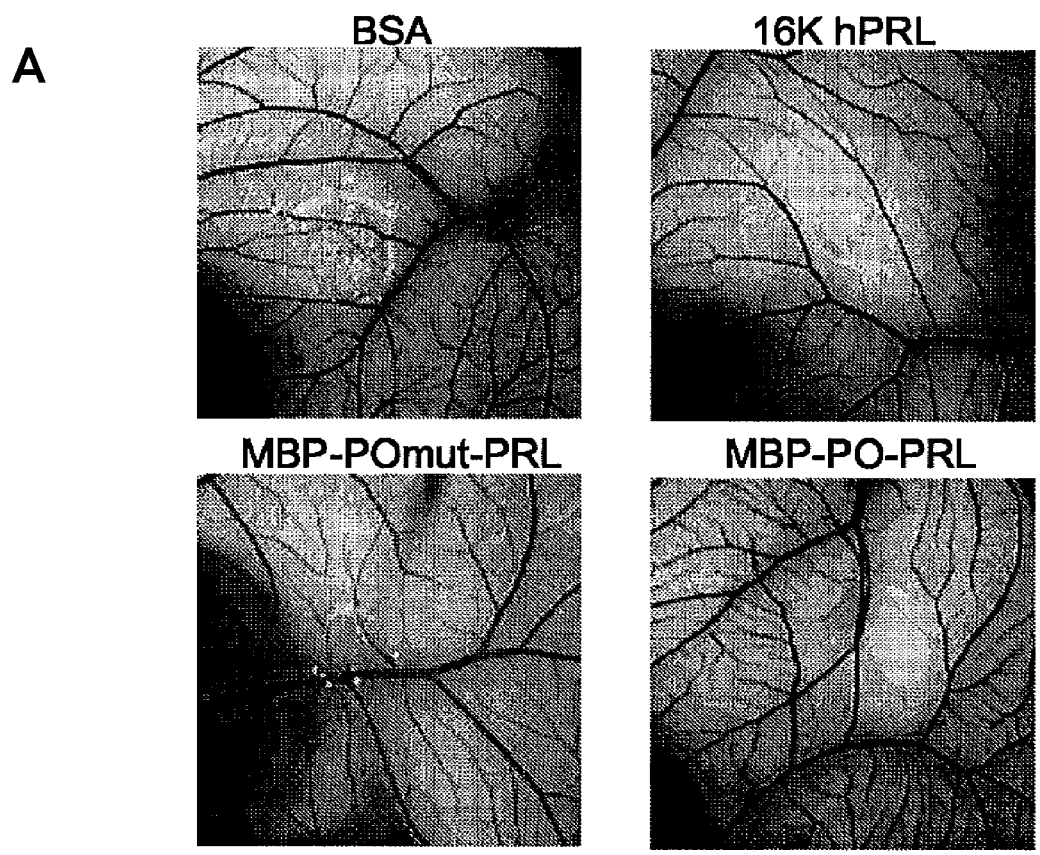
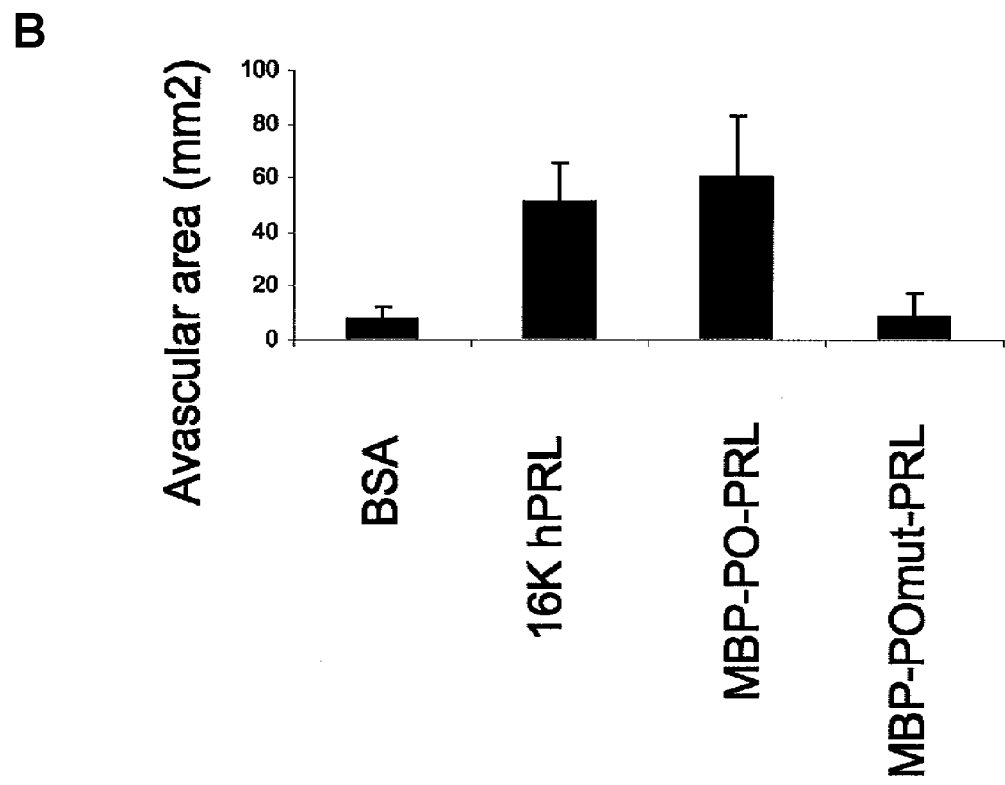
Fig. 10

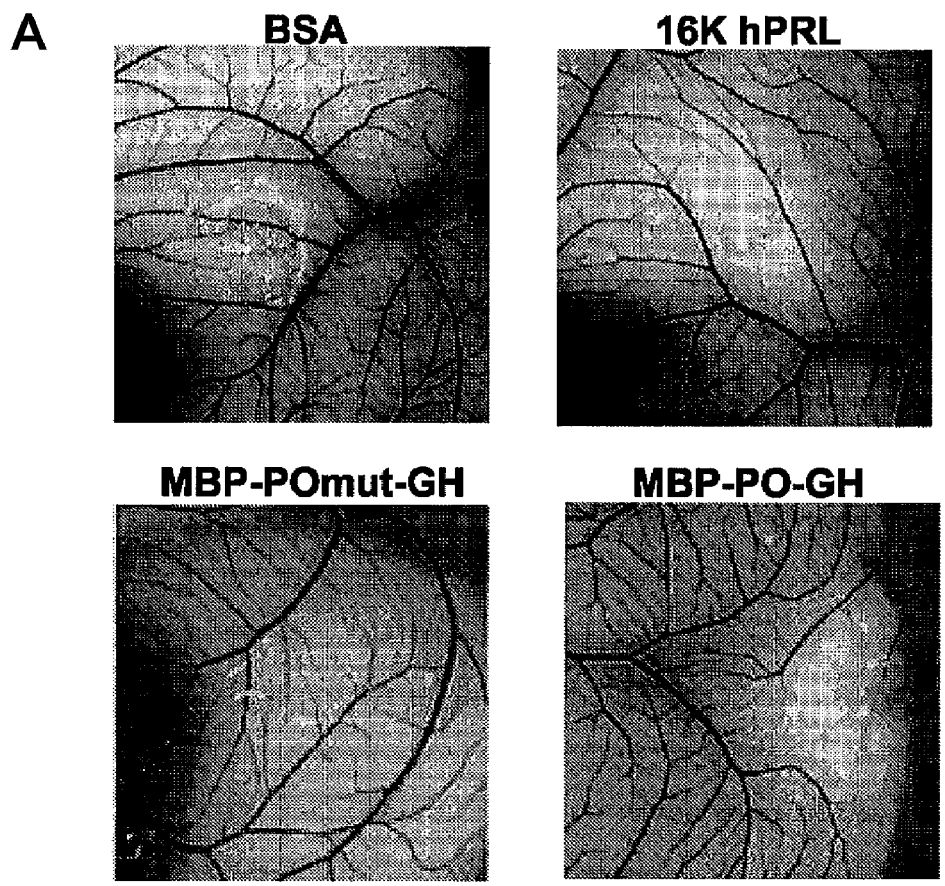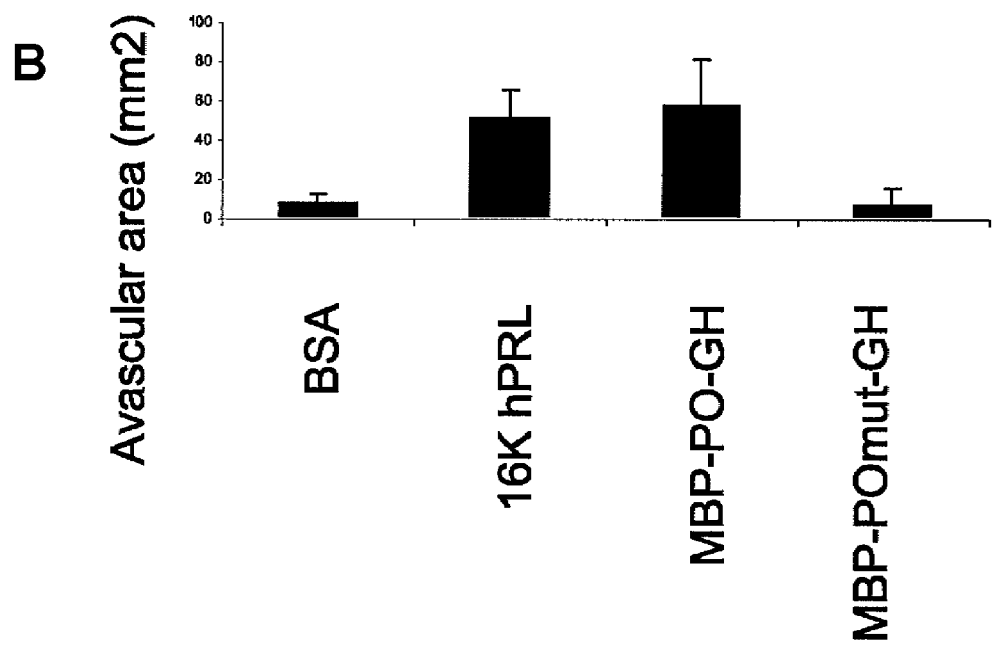
Fig. 12

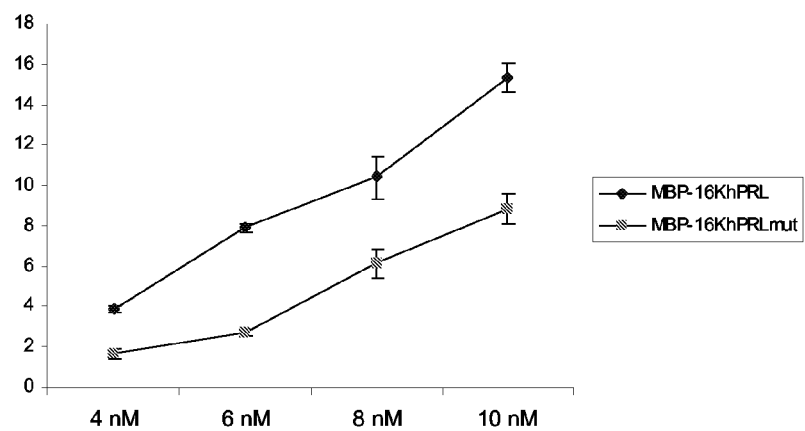
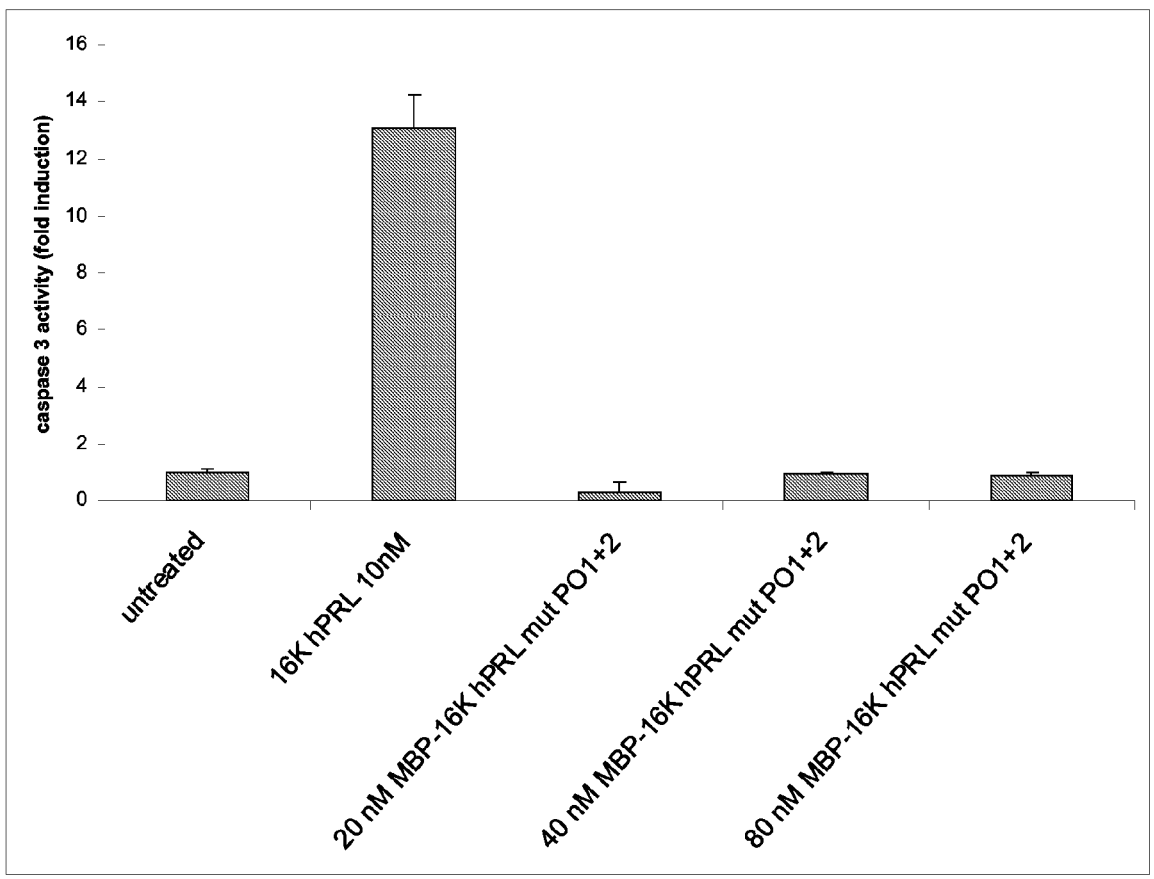
Fig. 17

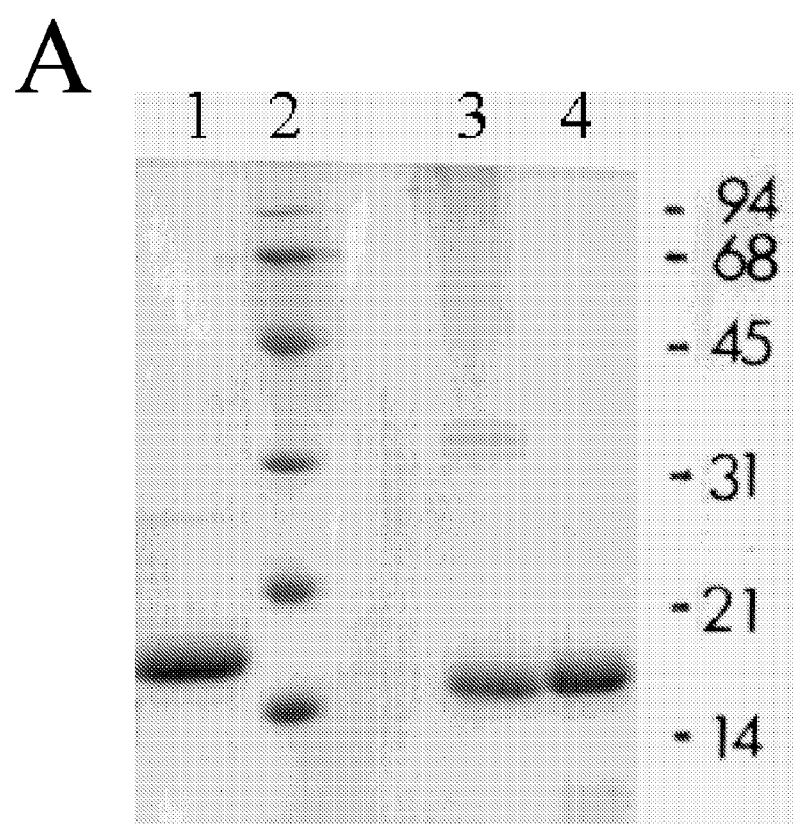
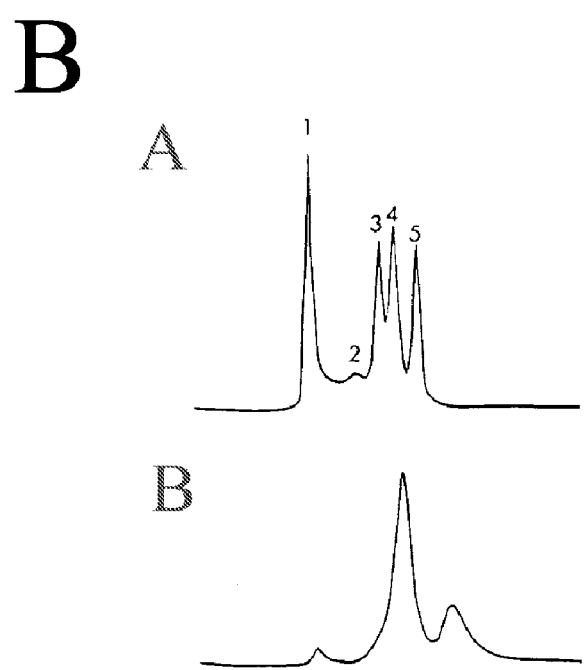
Fig. 18

ANTIANGIOGENIC PEPTIDES

RELATED APPLICATIONS

This application is a U.S. National Phase of International Application No. PCT/EP2005/053952, filed Aug. 11, 2005, designating the U.S. and published in English on Feb. 23, 2006 as WO 2006/018418, which claims the benefit of European Application No. 04103920.7, filed Aug. 16, 2004.

The present invention refers to antiangiogenic peptides, especially to tilted peptides having antiangiogenic properties and peptides from the prolactin/growth hormone family having antiangiogenic properties.

TECHNICAL FIELD

Angiogenesis, the process of capillary formation from pre-existing ones, is essential for normal growth and tissue repair. However, excessive angiogenesis has been shown to be involved in many diseases such as rheumatoid arthritis, diabetic retinopathy or cancer (angiogenesis related diseases) and the use of inhibitors of angiogenesis appears as a promising therapeutic treatment in these cases (the so-called anti-angiogenic therapy). In the state of art it was shown that the 16 kDa N-terminal fragment of the prolactin (16K PRL) is a powerful agent for anti-tumoral therapy oriented towards the destruction of newly-formed blood vessels essential for tumor growth. The N-terminal 16K fragments of others members of the human prolactin/growth hormone family, i.e. 16K growth hormone (16K hGH), 16K growth hormone variant (16K hGH-V) and 16K placental lactogen (16K hPL), also inhibit angiogenesis while, in contrast, the full-length hormones stimulate capillary formation (Struman, I., et al. Proc Natl Acad Sci USA 96:1246-51 (1999)).

BACKGROUND OF THE INVENTION

Angiogenesis is an essential component of normal processes such as growth and tissue repair (Conway, E. M., et al. Cardiovasc Res 49:507-21. (2001)) (Folkman, J. Semin Oncol 28:536-42. (2001)). Angiogenesis is also involved in the development of many pathological situations commonly called angiogenic diseases. Examples of pathological conditions leading to angiogenic diseases are, among other, arthritis, diabetic retinopathy, psoriasis, obesity and cancer (Carmeliet, P. Nat Med 9:653-60 (2003)). In the latter case, formation of new capillaries is essential not only for the growth of the primary tumor but also for the spreading of metastases (Fidler, I. J. Nat Rev Cancer 3:453-8 (2003)).

Recently the search for angiogenic inhibitors has been vigorously pursued. Currently, several angiogenic inhibitors including thrombospondin, platelet factor 4, angiostatin, endostatin, fumagillin and thalidomide are being studied. Several of these are in clinical trials e.g. fumagillin and thalidomide.

Also recently a new antiangiogenic factor has been identified: the 16 kDa N-terminal fragment of prolactin (human 16K prolactin or 16K hPRL). It was shown that 16K hPRL displays antiangiogenic properties both in vitro and in vivo (Ferrara, N., et al. Endocrinology 129:896-900 (1991), Clapp, C., et al. Endocrinology 133:1292-9. (1993), Lee, H., et al. Endocrinology 139:3696-703 (1998)). The 16K hPRL inhibits endothelial cell proliferation and induces their apoptosis (D'Angelo, G., et al. Proc Natl Acad Sci USA 92:6374-8 (1995), D'Angelo, G., et al. Mol Endocrinol 13:692-704 (1999), Martini, J. F., et al. Mol Endocrinol 14:1536-49. (2000)). Indeed, treatment of BEC (brain endothelial cell) with recombinant 16K prolactin increases DNA fragmentation in BEC in a time- and dose-dependent fashion (Martini, J. F., et al. Mol Endocrinol 14:1536-49. (2000)). 16K prolactin-induced apoptosis is correlated with the rapid activation of caspases 1 and 3 and an increase in the conversion of Bcl-X to its proapoptotic form. Further it was determined that the NF-κB signaling pathway is involved in mediating the apoptotic action of 16K hPRL in BEC. In a dose-dependent manner, treatment with 16K hPRL induces IκB-α degradation permitting translocation of NF-κB to the nucleus and reporter gene activation. Inhibition of NF-κB activation by overexpression of a non-degradable IκB-α mutant or treatment with NF-κB inhibitors blocks 16K hPRL-induced apoptosis. Treatment with 16K hPRL activates the initiator caspases 8 and 9 and the effector caspase 3, all of which are essential for inducing endothelial cell apoptosis. Activation of the caspases cascade by 16K hPRL is also NF-κB-dependent (Tabruyn, S. P., et al. Mol Endocrinol 17:1815-23 (2003)). 16K hPRL was shown to inhibit proliferation by inducing a cell cycle arrest at both the G1-S and G2-M phases (Tabruyn et al., Mol Endocrinol, 19, 1932-1942 (2005)).

In a recent publication it was disclosed that inhibition of angiogenesis by 16K hPRL is able to prevent the growth of subcutaneously implanted human colon tumors in the mouse (Bentzien, F., et al. Cancer Res 61:7356-62. (2001)). More recently, an adenovirus vector was engineered allowing the expression of 16K hPRL in situ. Further, the ability of 16K hPRL to prevent angiogenesis in a mouse model of retinopathy (Raisler, B. J., et al. Proc Natl Acad Sci USA 99:8909-14. (2002)) was evaluated. Results indicate that 16K hPRL produced in situ by adenovirus-mediated gene transfer inhibits vascular growth in the mouse retina (Pan et al., Invest Opthalmol V is Sci 45(7): 2413-2419 (2004). Taken together, these results suggested that 16K hPRL may be used as an agent for antitumoral therapy which is performing its effects through the destruction of newly formed blood vessels essential for tumor growth.

The N-terminal 16K fragments of others members of the human prolactin/growth hormone family (PRL/GH family), i.e. 16K growth hormone (16K hGH), 16K growth hormone variant (16K hGH-V) and 16K placental lactogen (16K hPL), were shown also to inhibit angiogenesis while, in contrast, the full-length hormones stimulate capillary formation (Struman, I., et al. Proc Natl Acad Sci U S A 96:1246-51 (1999)). Thus it appeared important to identify, within the 16K fragments, the region that is responsible for their antiangiogenic activity and to understand why these regions are inactive when they are included within the full-length proteins.

The disadvantage of the polypeptides of the state of art was that longer polypeptides are difficult to produce and difficult to purify. Further problems were due to instability and problems concerning their introduction into pharmaceutical compositions.

The object of the present invention was to identify and to provide the effective peptides having antiangiogenic activity which are easier to produce, purify and to handle. A further object was to provide pharmaceutical compositions comprising such peptides having antiangiogenic activity.

SUMMARY OF THE INVENTION

The object of the present invention was solved by a pharmaceutical composition comprising an isolated antiangiogenic peptide or a recombinant protein comprising the anti-angiogenic peptide, wherein the peptide is between 11 and 40 amino acids in length and having antiangiogenic activity, the peptide comprising the amino acid sequence:

X1-X2-X3-X4-X5-X6-X7-X8-X9-X10-X11-X12-X13-X14, wherein

X1 is any amino acid residue compatible with forming a helix;
X2 is an amino acid residue of: Leu, Ile, Val;
X3 is an amino acid residue of: Arg, Lys, His, Ser, Thr;
X4 is an amino acid residue of: Ile, Leu, Val;
X5 is any amino acid residue compatible with forming a helix;
X6 is an amino acid residue of: Leu, Ile, Val;
X7 is an amino acid residue of: Leu, Ile, Val, Ser, Thr;
X8 is any amino acid residue compatible with forming a helix;
X9 is any amino acid residue compatible with forming a helix;
X10 is an amino acid residue of: Gln, Glu, Asp, Arg, His, Lys, Asn;
X11 is an amino acid residue of: Ser, Thr;
X12 is an amino acid residue of: Trp, Tyr, Phe;
X13 is an amino acid residue of: Leu, Ile, Val, Asn, Gln;
X14 is an amino acid residue of: Glu, Gln, Asp, Asn, (SEQ ID NO: 21).

In a preferred embodiment the antiangiogenic peptide preferably is between 11 and 20, more preferred between 11 and 16 and most preferred between 11 and 14 amino acids in length. The antiangiogenic peptide may be as short as 11, 12 or 13 amino acid residues. Surprisingly, the inventors have found that such small peptides still have strong antiangiogenic activities. The advantage of these peptides is that they are effective peptides having antiangiogenic activity which are also easier to produce, purify and to handle. The invention also provides a recombinant protein comprising said antiangiogenic peptide. In this case the moiety of the recombinant protein not covering the antiangiogenic peptide serves as carrier for the antiangiogenic peptide. As example for a recombinant protein comprising the antiangiogenic peptide, maltose binding protein MBP can be mentioned to which the antiangiogenic peptide is fused by genetic engineering techniques.

The present invention therefore provides a pharmaceutical composition comprising an isolated antiangiogenic peptide or a recombinant protein comprising the antiangiogenic peptide, wherein the peptide is between 11 and 40 amino acids in length and having antiangiogenic activity, the peptide comprising from 11 to 14 consecutive amino acid residues of the following amino acid sequence:

X1-X2-X3-X4-X5-X6-X7-X8-X9-X10-X11-X12-X13-X14, wherein

X1 is any amino acid residue compatible with forming a helix;
X2 is an amino acid residue of: Leu, Ile, Val;
X3 is an amino acid residue of: Arg, Lys, His, Ser, Thr;
X4 is an amino acid residue of: Ile, Leu, Val;
X5 is any amino acid residue compatible with forming a helix;
X6 is an amino acid residue of: Leu, Ile, Val;
X7 is an amino acid residue of: Leu, Ile, Val, Ser, Thr;
X8 is any amino acid residue compatible with forming a helix;
X9 is any amino acid residue compatible with forming a helix;
X10 is an amino acid residue of: Gln, Glu, Asp, Arg, His, Lys, Asn;
X11 is an amino acid residue of: Ser, Thr;
X12 is an amino acid residue of: Trp, Tyr, Phe;
X13 is an amino acid residue of: Leu, Ile, Val, Asn, Gln;
X14 is an amino acid residue of: Glu, Gln, Asp, Asn (SEQ ID NO: 21).

This means that in case the antiangiogenic peptide is shorter than 14 amino acid residues the peptide may cover the above mentioned sequence from X1-X11, X1-X12, X1-X13, X2-X12, X2-X13, X2-X14, X3-X13, X3-X14 and X4-X14, respectively.

In a further preferred embodiment the peptide is defined as follows, wherein

X1 is any amino acid residue compatible with forming a helix, preferably Phe, Leu;
X2 is an amino acid residue of: Leu;
X3 is an amino acid residue of: Arg, Ser;
X4 is an amino acid residue of: Ile, Leu;
X5 is any amino acid residue compatible with forming a helix, preferably Ile, Ser;
X6 is an amino acid residue of: Leu, Val;
X7 is an amino acid residue of: Leu, Ser;
X8 is any amino acid residue compatible with forming a helix, preferably Ile, Leu;
X9 is any amino acid residue compatible with forming a helix, preferably Leu, Ile;
X10 is an amino acid residue of: Gln, Glu, Arg;
X11 is an amino acid residue of: Ser;
X12 is an amino acid residue of: Trp;
X13 is an amino acid residue of: Leu, Asn;
X14 is an amino acid residue of: Glu, (SEQ ID NO: 22).

In an even further preferred embodiment the peptide is defined as follows, wherein X1 is an amino acid residue of: Leu, Phe;
X2 is an amino acid residue of: Leu;
X3 is an amino acid residue of: Arg, Ser;
X4 is an amino acid residue of: Ile, Leu;
X5 is an amino acid residue of: Ser, Ile;
X6 is an amino acid residue of: Leu, Val;
X7 is an amino acid residue of: Leu, Ser,
X8 is an amino acid residue of: Leu, Ile;
X9 is an amino acid residue of: Ile, Leu;
X10 is an amino acid residue of: Gln, Glu, Arg;
X11 is an amino acid residue of: Ser;
X12 is an amino acid residue of: Trp;
X13 is an amino acid residue of: Leu, Asn;
X14 is an amino acid residue of: Glu, (SEQ ID NO: 23).

These sequences comprise the sequences and their homologous derivatives of tilted peptides of the prolactin/growth hormone family. Preferably, the amino acid sequence X1-X14 of the peptide is having at least 71%, preferably at least 78%, more preferably at least 85% and most preferred at least 92% identity to one of the following sequences:

```
                                            (SEQ ID NO: 1)
a) Leu Leu Arg Ile Ser Leu Leu Leu Ile Gln Ser Trp
   Leu Glu;

(SEQ ID NO: 2)
b) Leu Leu Arg Ile Ser Leu Leu Leu Ile Glu Ser Trp
   Leu Glu;

(SEQ ID NO: 3)
c) Phe Leu Ser Leu Ile Val Ser Ile Leu Arg Ser Trp
   Asn Glu;
``` wherein the replaced amino acid residues are replaced by homologous amino acid residues. These sequences comprise the sequences and their homologous derivatives of tilted peptides of the prolactin/growth hormone family. The homologous amino acid residues are those having similar features concerning hydrophobicity, polarity, charge, steric features. Preferably the peptide is a tilted peptide. The term "homology" is further explained and defined below.

In a further preferred embodiment the amino acid sequence X1-X14 of the peptide represents a tilted peptide. Preferably, the calculated mean hydrophobicity of the tilted peptide is higher than 0.1 and the tilted peptide is defined by the characteristics that if the three-dimensional structure of the peptide is arranged as alpha-helix the calculated hydrophobic isopotential of the peptide is asymmetric and the calculated minimal energy conformation is oriented at a hydrophobic/hydrophilic interface and the calculated angle between the helix axis and the interface plane of hydrophobic and hydrophilic phases is between 30° and 70°. In a preferred embodiment the calculated mean hydrophobicity of the tilted peptide is higher than 0.2, preferably higher than 0.3, more preferred higher than 0.5, more preferred higher than 0.8 and most preferred higher than 0.9.

Further, it is preferred that the calculated angle between the helix axis of the tilted peptide and the interface plane of hydrophobic and hydrophilic phases is between 35° and 65°, preferably between 40° and 60° and most preferred between 40° and 50°. The closer the angle between the helix axis of the peptide and the interface plane of hydrophobic and hydrophilic phases tends towards 45° the higher is the antiangiogenic activity of the peptide.

The object is also solved by a pharmaceutical composition comprising the above defined antiangiogenic peptide or comprising a polynucleotide encoding an antiangiogenic peptide or encoding a recombinant protein comprising the antiangiogenic peptide.

The object of the present invention is also solved by a pharmaceutical composition comprising one or more of the following substances:
a) a peptide having the sequence Leu Leu Arg Ile Ser Leu Leu Leu Ile Gln Ser Trp Leu Glu (SEQ ID NO: 1), (hGH, hGH-v);
b) a peptide having the sequence Leu Leu Arg Ile Ser Leu Leu Leu Ile Glu Ser Trp Leu Glu (SEQ ID NO: 2), (hPL);
c) a peptide having the sequence Phe Leu Ser Leu Ile Val Ser Ile Leu Arg Ser Trp Asn Glu (SEQ ID NO: 3); (hPRL);
d) a peptide having the sequence Pro Leu Tyr His Leu Val Thr Glu Val Arg Gly Met Gln Glu Ala (SEQ ID NO: 8), (hPRL);
e) a peptide having at least 70%, preferably at least 80%, more preferably 85% and most preferred at least 90% identity to the peptide of a) to d), wherein the replaced amino acid residues preferably are replaced by homologous amino acid residues;
f) a recombinant protein comprising any one of the peptide sequences of a) to e);
g) a polynucleotide encoding an antiangiogenic peptide of any one of a) to e) or encoding a recombinant protein of f).

The abbreviations following the sequence identity number in a) to d) indicate the origin of the peptide.

The object is also solved by a pharmaceutical composition comprising a peptide or a recombinant protein or a polynucleotide of as mentioned above. In a preferred embodiment the peptide represents a tilted peptide.

Further the present invention provides a pharmaceutical composition comprising two peptides having the sequences SEQ ID NO: 3 and SEQ ID NO: 8, respectively; or peptides having at least 70%, preferably at least 80%, more preferably 85% and most preferred at least 90% identity to said peptides, wherein the replaced amino acid residues preferably are replaced by homologous amino acid residues; or
recombinant proteins comprising separately or in combination said peptide sequences; or
polynucleotides encoding said antiangiogenic peptides or encoding said recombinant proteins. Surprisingly it was shown that the peptides having the sequences SEQ ID NO: 3 and SEQ ID NO: 8, respectively, in combination have a stronger antiangiogenic effect than if the peptides were used separately. Preferably, the peptides are fused to carrier proteins which are recombinant proteins comprising said peptide sequence. Two alternatives are possible: there is either a recombinant protein provides which carries one kind of peptide, or one recombinant protein which carries both antiangiogenic peptides. In the latter case the antiangiogenic peptides are fused together in direct neighborhood or are separated by a linker sequence.

In a preferred embodiment the above described amino acid sequence X1-X14, or the peptide (the antiangiogenic peptide), or the recombinant protein comprising the peptide, respectively, forms a trimeric structure. The trimeric organisation of the peptide or the recombinant protein comprising the peptide, respectively, is important to maintain the antiangiogenic activity.

The object of the present invention is also solved by a peptide selected from the group:
a) a peptide having the sequence Phe Leu Ser Leu Ile Val Ser Ile Leu Arg Ser Trp Asn Glu (SEQ ID NO: 3), (hPRL);
b) a peptide having the sequence Pro Leu Tyr His Leu Val Thr Glu Val Arg Gly Met Gln Glu Ala (SEQ ID NO: 8), (hPRL)
c) a peptide having at least 70%, preferably at least 80%, more preferably 85% and most preferred at least 90% identity to the peptide of a) or b), wherein the replaced amino acid residues preferably are replaced by homologous amino acid residues;
d) a recombinant protein comprising the peptide sequences of a) to c);
e) a polynucleotide encoding an antiangiogenic peptide of a) to c) or encoding a recombinant protein of d).

In the hPRL sequence two tilted peptides have been identified (SEQ ID NOs: 3 and 8. As shown in example 8.3 and 8.4 also the second tilted peptide region of the 16K hPRL plays a role in 16K hPRL antiangiogenic activity. The 16K hPRL was mutated in its two tilted peptide regions and was produced in fusion with the MBP. This protein is called MBP-16 KhPRL-mut PO 1+2. The ability of MBP-16K hPRL and MBP-16 KhPRLmut PO 1+2 to induce caspase 3 activation is shown in FIG. 17, panel B. The activation of the caspase 3 is abolished when ABAE cells are treated with the MBP-16 KhPRLmut PO 1+2 by comparison with the MBP-16 KhPRL. These results show that both tilted peptide regions are required for the antiangiogenic activity of 16K hPRL.

The present invention further provides a composition comprising two peptides having the sequences SEQ ID NO: 3 and SEQ ID NO: 8 or
peptides having at least 70%, preferably at least 80%, more preferably 85% and most preferred at least 90% identity to said peptides, wherein the replaced amino acid residues preferably are replaced by homologous amino acid residues; or
recombinant proteins comprising separately or in combination said peptide sequences; or
polynucleotides encoding said antiangiogenic peptides or encoding said recombinant proteins.

Further, the object is solved by the use of a peptide or a recombinant protein or a polynucleotide as mentioned above for the manufacture of a medicament for the preventive and/or therapeutic treatment of angiogenesis-related diseases.

The object is also solved by the use of one or more of the following substances for the manufacture of a medicament for the preventive and/or therapeutic treatment of angiogenesis related diseases:

a) a peptide having the sequence Leu Leu Arg Ile Ser Leu Leu Leu Ile Gln Ser Trp Leu Glu (SEQ ID NO: 1), (hGH, hGH-v);
b) a peptide having the sequence Leu Leu Arg Ile Ser Leu Leu Leu Ile Glu Ser Trp Leu Glu (SEQ ID NO: 2), (hPL);
c) a peptide having the sequence Phe Leu Ser Leu Ile Val Ser Ile Leu Arg Ser Trp Asn Glu (SEQ ID NO: 3), (hPRL);
d) a peptide having the sequence Pro Leu Tyr His Leu Val Thr Glu Val Arg Gly Met Gln Glu Ala (SEQ ID NO: 8), (hPRL);
e) a peptide having the sequence Ala Gly Ala Val Val Gly Gly Leu Gly Gly Tyr Met Leu Gly Ser Ala Met Ser (SEQ ID NO: 5), (prion);
f) a peptide having the sequence Gly Ala Ile Ile Gly Leu Met Val Gly Gly Val Val Ile Ala (SEQ ID NO: 6), (β-amyloid);
g) a peptide having the sequence Gly Val Phe Val Leu Gly Phe Leu Gly Phe Leu Ala (SEQ ID NO: 7), (SIV fusion protein);
h) a peptide having any one of the following sequences:

Gly Ala Ile Ile Gly Leu Met Val Gly Gly Val Val
(SEQ ID NO: 24) (β-amyloid),

Ala Val Gly Ile Gly Ala Leu Phe Leu Gly Phe Leu
(SEQ ID NO: 25) (HIV),

Lys Thr Asn Met Lys His Met Ala Gly Ala Ala Ala
Ala Gly Ala Val Val Gly Gly Leu Gly
(SEQ ID NO: 26) (Prp 106-126 (Prion)), Phe Ala Gly Val Val Leu Ala Gly Ala Ala Leu Gly
(SEQ ID NO: 27) (Measles virus), Phe Ile Gly Ala Ile Ile Gly Ser Val Ala Leu Gly
Val Ala Thr Ala Ala Gly (SEQ ID NO: 28) (NDV), Phe Leu Gly Phe Leu Leu Gly Val Gly Ser Ala Ile
Ala Ser Gly Val Ala (SEQ ID NO: 29)
(Rous sarcoma virus), Phe Phe Gly Ala Val Ile Gly Thr Ile Ala Leu Gly
Val Ala Thr Ser Ala (SEQ ID NO: 30)
(Sendai virus), Ser Pro Val Ala Ala Leu Thr Leu Gly Leu Ala Leu
(SEQ ID NO: 31) (BLV), Gly Pro Val Ser Leu Thr Leu Ala Leu Leu Leu Gly
Gly Leu Thr Met Gly (SEQ ID NO: 32) (MLV), Gly Ala Ala Ile Gly Leu Ala Trp Ile Pro Tyr Phe
Gly Pro Ala Ala Glu (SEQ ID NO: 33) (Ebola), Met Leu Leu Gln Ala Phe Leu Phe Leu Leu Ala Gly
Phe Ala Ala Lys Ile Ser Ala (SEQ ID NO: 34)
(Yeast invertase SP), Arg Pro Ala Leu Leu Ala Leu Leu Ala Leu Pro Ala
(SEQ ID NO: 35) (ApoB 100 SP), Val Thr Val Val Leu Trp Ser Ala Tyr Pro Val Val
Trp Leu Ile Gly (SEQ ID NO: 36) (1bct 177), Gly Ala Gly Ile Val Pro Leu Asn Ile Glu Thr Leu
Leu Phe Met Val Leu Asp (SEQ ID NO: 37)
(1bct 195), Ile Lys Lys Ala Gly Thr Glu Leu Val Asn Phe Leu
Ser Tyr Phe Val Glu Leu (SEQ ID NO: 38) (ApoA-II), Ala Ser Leu Leu Ser Phe Met Gln Gly Tyr Met Lys
His Ala Thr (SEQ ID NO: 39) (apo C-III), Phe Gly Phe Pro Glu His Leu Leu Val Asp Phe Leu
Gln Ser Leu Ser (SEQ ID NO: 40) (CETP), Asp Phe Phe Thr Ile Trp Leu Asp Leu Asn Met Phe
Leu (SEQ ID NO: 41) (LCAT), Phe Leu Glu Leu Tyr Arg His Ile Ala Gln His Gly
Phe (SEQ ID NO: 42) (HLP), Ile Gly Glu Ala Ile Arg Val Ile Ala Glu Arg Gly
Leu (SEQ ID NO: 43) (LPL), Gly Leu Phe Gly Ala Ile Ala Gly Phe Ile Glu Asn
Gly Trp Glu Gly Met Ile Asp Gly (SEQ ID NO: 44)
(Influenza HA-2), Met Glu Asn Ile Thr Ser Gly Phe Leu Gly Pro Leu
Leu Val Leu Gln (SEQ ID NO: 45)
(Hepatitis B, S protein), Thr Glu Leu Val Asn Phe Leu Ser Tyr Phe Val Glu
Leu (SEQ ID NO: 46) (Human Apo A-II Sakacin P), Val Ile Gly Thr Asn Ala Val Ser Ile Glu Thr Asn
Ile Glu (SEQ ID NO: 47) (Meltrine), Asp Ser Thr Lys Cys Gly Lys Leu Ile Cys Thr Gly
Ile Ser Ser Ile Pro (SEQ ID NO: 4) (Fertiline), Ala Ser Leu Leu Ser Phe Met Gln Gly Tyr Met Lys
His Ala Thr (SEQ ID NO: 13) (APO C-III), i) a peptide having at least 70%, preferably at least 80%, more preferably 85% and most preferred at least 90% identity to the peptide of a) to h), wherein the replaced amino acid residues preferably are replaced by homologous amino acid residues;
j) a recombinant protein comprising any one of the peptide sequences of a) to i);
k) a polynucleotide encoding an antiangiogenic peptide of any one of a) to i) or encoding a recombinant protein of j).

The abbreviations following the sequence identity number in a) to h) indicate the origin of the peptide. The peptides have been described in the prior art as follows: SEQ ID NOs: 5-7, 24, 25, 27-43 in Lins, L. et al., Proteins 44, 435-447 (2001); SEQ ID NO: 13 in Lins, L. et al., Proteins Eng. 15, 513-520 (2002); SEQ ID NO: 26 in Dupiereux, I. et al., Biochem. Biophys. Res. Commun., 331, 894-901 (2005); SEQ ID NOs: 4, 44-47 in Brasseur, R. Mol. Membr. Biol. 17, 31-40 (2000). The term "angiogenesis related diseases" refers for example to diseases like rheumatoid arthritis, diabetic retinopathy or cancer.

The present invention further provides a composition comprising two peptides having the sequences SEQ ID NO: 3 and SEQ ID NO: 8, respectively, or peptides having at least 70%, preferably at least 80%, more preferably 85% and most preferred at least 90% identity to said peptides, wherein the replaced amino acid residues preferably are replaced by homologous amino acid residues; or recombinant proteins comprising separately or in combination said peptide sequences; or polynucleotides encoding said antiangiogenic peptides or encoding said recombinant proteins.

The object is also solved by a method for the preventive and/or therapeutic treatment of angiogenesis-related diseases, wherein a therapeutically effective dose of a peptide or a recombinant protein or a polynucleotide as mentioned above is administered to a patient.

The object is also solved by a pharmaceutical composition comprising a substance selected from the group:
a) a tilted peptide, wherein the peptide is having antiogenic properties and the peptide has a length of 11 to 20 amino acids;
b) a recombinant protein comprising the peptide of a);
c) a polynucleotide encoding the peptide of a) or the recombinant protein of b).

In a preferred embodiment the calculated mean hydrophobicity of the peptide is higher than 0.1 and the tilted peptide is defined by the characteristics that if the three-dimensional structure of the peptide is arranged as alpha-helix the calculated hydrophobic isopotential of the peptide is asymmetric and the calculated minimal energy conformation is oriented at a hydrophobic/hydrophilic interface and the calculated angle between the helix axis and the interface plane of hydrophobic and hydrophilic phases is between 30° and 70°.

In a further preferred embodiment the calculated mean hydrophobicity of the peptide is higher than 0.2, preferably higher than 0.3, more preferred higher than 0.5, even more preferred higher than 0.8 and most preferred higher than 0.9.

Further it is preferred that the calculated angle between the helix axis of the peptide and the interface plane of hydrophobic and hydrophilic phases is between 35° and 65°, preferably between 40° and 60° and most preferred between 40° and 50°.

The object is also solved by a pharmaceutical composition comprising an isolated antiangiogenic peptide or a recombinant protein comprising the antiangiogenic peptide, wherein the peptide is a tilted peptide and derived from a protein of the prolactin (PRL)-growth hormone family (GH). The features for defining a tilted peptide are defined above. In an alternative embodiment a pharmaceutical composition is provided which comprises a polynucleotide encoding said antiangiogenic peptide or encoding a recombinant protein comprising said antiangiogenic peptide, wherein the peptide is a tilted peptide and derived from a protein of the prolactin (PRL)-growth hormone family (GH).

In a further embodiment a pharmaceutical composition is provided which comprises an isolated antiangiogenic peptide or a recombinant protein comprising the antiangiogenic peptide, wherein the antiangiogenic peptide is derived from a protein of the prolactin (PRL)-growth hormone family (GH) and is having any one of the following sequences:
a) a peptide having the sequence Leu Leu Arg Ile Ser Leu Leu Leu Ile Gln Ser Trp Leu Glu (SEQ ID NO: 1), (hGH, hGH-v)
b) a peptide having the sequence Leu Leu Arg Ile Ser Leu Leu Leu Ile Glu Ser Trp Leu Glu (SEQ ID NO: 2), (hPL);
c) a peptide having the sequence Phe Leu Ser Leu Ile Val Ser Ile Leu Arg Ser Trp Asn Glu (SEQ ID NO: 3), (hPRL);
d) a peptide having the sequence Pro Leu Tyr His Leu Val Thr Glu Val Arg Gly Met Gln Glu Ala (SEQ ID NO: 8), (hPRL).

In a particular preferred embodiment a pharmaceutical composition is provided which comprises an isolated antiangiogenic peptide or a recombinant protein comprising the antiangiogenic peptide, wherein the antiangiogenic peptide is derived from the prolactin (PRL) protein, wherein the antiangiogenic peptide or its sequence, respectively, is having any one of the following sequences:
a) a peptide having the sequence Phe Leu Ser Leu Ile Val Ser Ile Leu Arg Ser Trp Asn Glu (SEQ ID NO: 3), (hPRL);
b) a peptide having the sequence Pro Leu Tyr His Leu Val Thr Glu Val Arg Gly Met Gln Glu Ala (SEQ ID NO: 8), (hPRL).

The present invention further provides a pharmaceutical composition comprising two isolated antiangiogenic peptides or recombinant proteins comprising separately or in combination said antiangiogenic peptides, wherein the antiangiogenic peptides are derived from the prolactin (PRL) protein and are having the following sequences:
a) a peptide having the sequence Phe Leu Ser Leu Ile Val Ser Ile Leu Arg Ser Trp Asn Glu (SEQ ID NO: 3), (hPRL);
b) a peptide having the sequence Pro Leu Tyr His Leu Val Thr Glu Val Arg Gly Met Gln Glu Ala (SEQ ID NO: 8), (hPRL).

In a preferred embodiment the above mentioned peptides are comprised in a pharmaceutical composition. Such a pharmaceutical composition is used for preventive and/or therapeutic treatment of angiogenesis-related diseases. Further there is provided the use of said peptides or of said recombinant protein or said polynucleotide for the manufacture of a medicament for the preventive and/or therapeutic treatment of angiogenesis-related diseases. The present invention also provides a method for the preventive and/or therapeutic treatment of angiogenesis-related diseases characterized in that a therapeutically effective amount or dose of a peptide or a recombinant protein or a polynucleotide is administered to a patient. The term "angiogenesis related diseases" refers for example to diseases like rheumatoid arthritis, diabetic retinopathy or cancer.

The present invention was achieved by the search for antiangiogenic peptides that mimic the PRL/GH 16K fragments activity. The design of peptides represents a powerful approach for the development of new bioactive molecules. In the field of angiogenesis, many inhibitors are indeed cryptic fragments of endogenous molecules that are not themselves antiangiogenic; this is the case for the 16K hPRL, endostatin (collagen XVIII fragment)(O'Reilly, M. S., et al. Cell 88:277-85. (1997)), angiostatin (plasminogen fragment)(O'Reilly, M. S., et al. Cell 79:315-28. (1994)), among others. Recently, several synthetic peptides inhibiting angiogenesis have been identified. These peptides have been obtained either by dissecting arbitrarily the molecules into shorter peptides (Maeshima, Y., et al. J Biol Chem 276:31959-68 (2001)), or by phage-display screening (Hetian, L., et al. J Biol Chem 277:43137-42 (2002)). Less frequently, a more rationale structural approach was used (Sebti, S. M. and Hamilton, A. D. Oncogene 19:6566-73 (2000)). With this approach, the Anginex peptide was designed based on a comparative structural analysis performed on several antiangiogenic factors: PF4 (platelet factor-4), IL-8 (interleukine-8) et BPI (bactericidal-permeability increasing protein) (Griffioen, A. W., et al. Biochem J 354:233-42 (2001)).

From a therapeutic point of view, the benefit of using peptides would appear to be a rather low: they present shorter half-lives and weaker activities. However, in the field of angiogenesis, the activity of several peptides was shown to be similar to and even sometimes higher than that of the parent molecule (Griffioen, A. W., et al. Biochem J 354:233-42 (2001)) (Sebti, S. M. and Hamilton, A. D. Oncogene 19:6566-73 (2000)). Furthermore, peptides present the advantage of being more easily produced. This is an important issue since many antiangiogenic protein fragments like angiostatin, endostatin or 16K hPRL are usually very difficult to produce.

Tilted peptides (or oblique-oriented peptides [PO]) were discovered by molecular modelling some fifteen years ago (Brasseur, R. J Biol Chem 266:16120-7 (1991)). They are short protein fragments (10 to 20 amino acids) adopting an helical structure with an asymmetrical distribution of hydrophobic residues. To satisfy their hydrophobic gradient, these peptides adopt an oblique orientation when interacting with a hydrophobic/hydrophilic interface such as the lipid/water interface (Brasseur, R. Mol Membr Biol 17:31-40 (2000)). This obliquity allows them to destabilize the system in which they have been inserted and displays a potential role in the function of the protein they belong to (Lins, L., et al. Proteins 44:435-47 (2001)). On the other hand, through this destabilizing activity, most of these peptides induce liposome fusion in vitro (Martin, I., et al. Biochem Biophys Res Commun 175:872-9 (1991), Pillot, T., et al. J Biol Chem 271:28757-65 (1996), Pillot, T., et al. J Mol Biol 274:381-93 (1997), Lins, L., et al. Protein Eng 15:513-20 (2002)). Mutations that modify the hydrophobic distribution and thus the oblique orientation of the peptide modify their fusiogenic potential. For some of these peptides, mutagenesis has been performed on the full-length protein; the results confirmed the importance of the hydrophobic gradient in the activity of the peptide and the function of the protein (Horth, M., et al. Embo J 10:2747-55 (1991), Talmud, P., et al. Protein Eng 9:317-21 (1996), Lins, L., et al. Protein Eng 15:513-20 (2002)).

Tilted peptides have been discovered in many different proteins exhibiting various functions. For example, tilted peptides have been discovered in viral fusion proteins (Horth, M., et al. Embo J 10:2747-55 (1991), Voneche, V., et al. J Biol Chem 267:15193-7 (1992), Epand, R. F., et al. Biochem Biophys Res Commun 205:1938-43 (1994)), in the β-amyloid peptide (Pillot, T., et al. J Biol Chem 271:28757-65 (1996)), in signal peptides, lipid-transfer protein, (Brasseur, R., et al. Trends Biochem Sci 22:167-71 (1997)) and in prion protein (Pillot, T., et al. J Mol Biol 274:381-93 (1997)). Recently, the presence of tilted peptides in lipid bilayers has been demonstrated by neutron diffraction (Bradshaw, J. P., et al. Biochemistry 39:6581-5 (2000)).

The present invention provides peptides derived from the 16K fragments that can be used in antiangiogenic therapy. The present inventors hypothesize that a region, having the characteristic of a tilted peptide, is buried in the PRL/GH structure becomes exposed in the 16K fragment and responsible for the activity of the 16K fragments. Furthermore, the inventors propose that this region should be presented in an adequate way to be active. Such a way could be achieved by 16K hPRL. In this case, 16K hPRL adopts a new tridimensional structure, which is different from full-length hPRL, and which is characterized by a trimeric organization. This structure allows the exposition of the tilted peptide region. Another way is to fuse this region to the maltose binding protein (MBP). MBP allows an adequate presentation of the tilted peptide region. Without being bound to any theory, the trimeric organisation in the 16K hPRL protein fragment also applies to the peptide according to the present invention.

Using molecular modelling, the present inventors identified within the PRL/GH 16K fragments, a region that is susceptible to be exposed and to adopt a "tilted peptide" structure. Tilted peptides (or oblique-oriented peptides) are short protein fragments (10 to 20 amino acids long) that show an oblique orientation when they interact with a hydrophobic/hydrophilic interface such as the lipid/water interface. The present inventors obtained a synthetic peptide comprising the tilted region of the 16K prolactin and showed that this peptide induces liposome fusion in vitro, a feature of tilted peptides. The inventors constructed an expression vector coding for the tilted peptide of 16K hPRL fused to the maltose binding protein (MBP), namely MPB-PO-PRL, and demonstrated that this fusion protein induces apoptosis of endothelial cells with an activity similar to that of 16K hPRL. As a control, the inventors produced intact MBP protein and MBP fused to a mutated tilted peptide of 16K hPRL, namely MBP-POmut-PRL, that contains mutations predicted to modify the hydrophobic distribution and thus the oblique orientation of the peptide. Both controls were inactive in promoting apoptosis of endothelial cells. Similar results were obtained with MBP fused to the tilted peptide of hGH.

Based on these results, the inventors propose that the tilted peptide is a region, within the 16K fragments, that could be responsible for their antiangiogenic activity; it is postulated that this region is hidden (and thus inactive) in the full-length hormones but becomes accessible in the 16K fragments. It is further proposed that a similar region is responsible for the activity of other inhibitors of angiogenesis that are also protein fragments. The inventors also produced fusion proteins made of MBP and well-known tilted peptides of proteins whose function is not related to angiogenesis the β-amyloid B protein and the fusion protein of SIV virus. These latters also inhibit angiogenesis but at higher concentration than the fusion made with tilted peptide derived from antiangiogenic molecules like the 16K fragments.

The present invention provides a method to design and produce peptides that are able to inhibit angiogenesis and that could be used for the treatment of angiogenesis-related diseases like cancer, retinopathy and psoriasis. From a therapeutic point of view, the present inventors here demonstrate a method for production in an active conformation of antiangiogenic fragments i.e. endostatin or 16K hPRL, that are difficult to produce otherwise.

BRIEF DESCRIPTION OF THE FIGURES.

FIG. 1 shows in A. a protein sequence of hPRL (SEQ ID NO:14). The hPRL protein contains two tilted peptides: the region which is likely to adopt a tilted peptide structure is highlighted in bold (1$^{st}$ tilted peptide SEQ ID NO: 3) and in italics (2$^{nd}$ tilted peptide SEQ ID NO: 8). Alpha-helical regions are indicated by underlining (Keeler, C., et al. J Mol Biol 328:1105-21(2003)). B. Alignment of the tilted peptide regions in the 16K fragments of the PRL/GH family.

FIG. 10 shows that MBP-PO-PRL inhibits capillary formation in vivo in the chick chorioallantoic membrane assay according to example 3.6.5.

FIG. 12 shows that MBP-PO-GH inhibits capillary formation in vivo in the chick chorioallantoic membrane assay according to example 4.2.4.

FIG. 17 shows that 16K hPRL fused to MBP and mutated in its tilted peptide region (MBP-16K hPRLmut) (panel A) is less able to induce caspase 3 activation in endothelial cells than unmutated 16K hPRL fused to MBP (MBP-16K hPRL) according to example 8. Mutation of both tilted peptides of 16K hPRL completely abolishes 16 K hPRL activity (panel B) (Example 8.3 and 8.4).

FIG. 18 shows that 16K hPRL is monomeric in denaturating condition but trimeric in native conditions according to example 9. Panel A: 17% polyacrylamide SDS-PAGE of 16K hPRL. Lane 1-3: SDS-PAGE in the presence of β-ME. Lane 1: purified 16K hPRL. Lane 2: molecular weight marker. Lane 3: protein unrelated to this topics. Lanes 4: SDS-PAGE in the absence of β-ME : purified 16K hPRL. To the right, molecular weight of the marker are shown (in kDa). Panel B: Analytical size exclusion chromatography of 16K hPRL on a Superose 12 molecular sieve A: Calibration of the column with Dextran blue (peak 1), dimeric (peak 2) and monomeric BSA (peak 3), ovalbumin (peak 4) and myoglobin (peak 5); B: 16K hPRL

DETAILED DESCRIPTION OF THE INVENTION

Figure 2:
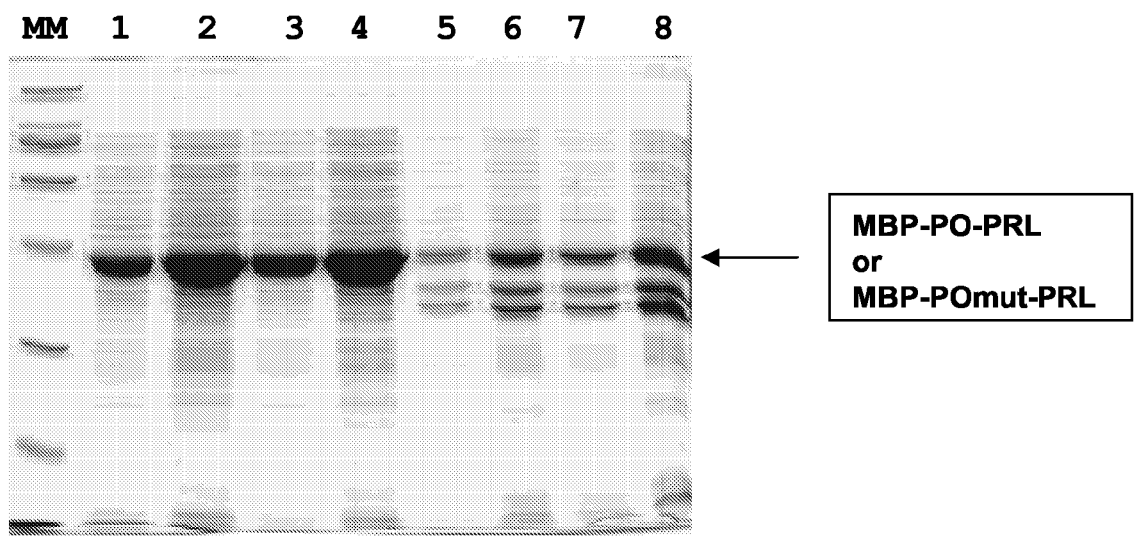
FIG. 2 shows a 12% SDS-PAGE analysis of the MBP-PO-PRL and MBP-POmut-PRL solubility 5 h after IPTG induction according to example 3.4. MM: molecular weight marker; Lanes 1-2: MBP-PO-PRL cell lysate supernatant; Lanes 3-4: MBP-POmut-PRL cell lysate supernatant; Lanes 5-6: MBP-PO-PRL cell lysate pellet; Lanes 7-8: MBP-POmut-PRL cell lysate pellet; 1, 3, 5, 7: the equivalent of 150 μl of a O.D.=1 of culture was loaded. 2, 4, 6, 8: the equivalent of 300 μl of a O.D.=1 of culture was loaded. The arrow indicates the MBP-PO-PRL or MBP-POmut-PRL protein.

This invention provides a new class of molecules which have the ability to inhibit angiogenesis. These molecules are referred to herein as "antiangiogenic tilted peptides".

The term "antiangiogenic tilted peptide" preferably refers to a peptide that is composed of the amino acids of the tilted region of the PRL/GH family. The term "tilted region of the PRL/GH family" refers to the sequence from Phe80 to Glu93 in hPRL and from Leu 75 to Glu 88 in hGH, hGH-V and hPL. More preferred the term "antiangiogenic tilted peptide" refers to a peptide as described in FIG. 1.

The term "antiangiogenic peptide" refers to a peptide that is able to inhibit angiogenesis (Folkman, J. Semin Cancer Biol 13:159-67 (2003)). A peptide is considered as antiangiogenic if it is able to induce endothelial cell apoptosis and/or to inhibit endothelial cell proliferation and/or to inhibits endothelial cell migration.

The term "tilted peptide" refers to a peptide that is considered as tilted. A tilted peptide can be detected using the procedure of molecular modelling described in (Brasseur, R. Mol Membr Biol 17:31-40 (2000)). Briefly, a peptide is considered as tilted if it shows the following properties: the peptide is 10 to 20 amino acids long; its mean hydrophobicity (as calculated by the Eisenberg consensus scale) is higher than 0.1. The hydrophobicity along the sequence is analyzed using different methods such as the Jähnig and Hydrophobic Cluster Analysis methods (Gaboriaud, C., et al. FEBS Lett 224:149-55 (1987), Jahnig, F. Trends Biochem Sci 15:93-5 (1990)). When the peptide is built as a α helix, the angle between the helix axis and the interface plane is between 30° and 70°. The minimal energy conformation is oriented at the hydrophobic/hydrophilic interface. Molecular Hydrophobicity Potentials are calculated and the hydrophobic isopotential envelopes are asymmetric. The characteristic of a tilted peptide is to induce liposome fusion in in vitro experiments.

The term "antiangiogenic tilted peptide" also includes shorter, longer or modified peptides made from the amino acid sequence of the tilted region of the PRL/GH family but with the modified peptide which is considered as tilted. The term "antiangiogenic tilted peptide" also includes peptides with substitutions of any amino acids including substitution of natural amino acids with other molecules, including but not limited to naturally and not-naturally occurring amino acids, as far as the tilted characteristic is maintained.

This invention also provides a method for the production of antiangiogenic tilted peptides using the recombinant technology approach. This peptide used at a concentration ranging from 1 nM to 1 μM, more preferred 20 to 200 nM is able to induce apoptosis of endothelial cells. This method consists in the production of the tilted peptide fused to a carrier polypeptide/protein as for example the "maltose binding protein" (MBP).

Angiogenesis, Angiogenic Conditions and Angiogenic Diseases. The peptides of the invention and their respective pharmaceutical compositions and preparations which are capable of inhibiting angiogenesis are useful for preventing or treating any disease or condition which is associated with or results in or from angiogenesis. Such diseases include formation of malignant tumors, angiofibroma, arteriovenous malformations, arthritis, such as rheumatoid arthritis, atherosclerotic plaques, corneal graft neovascularization, delayed wound healing, proliferative retinopathy such as diabetic retinopathy, macular degeneration, granulations such as those occurring in hemophilic joints, inappropriate vascularization in wound healing such as hypertrophic scars or keloid scars, neovascular glaucoma, ocular tumor, uveitis, non-union fractures, Osier-Weber syndrome, psoriasis, pyogenic glaucoma, retrolental fibroplasia, scleroderma, solid tumors, Kaposi's sarcoma, trachoma, vascular adhesions, chronic varicose ulcers, leukemia, and reproductive disorders such as follicular and luteal cysts and choriocarcinoma, among others.

Given their antiangiogenic activity, the peptides of the invention are also suitable for use in a method of inhibiting mammalian cell proliferation and organization that depends on vascularization, including the selective inhibition of vascularization of tumors, tumor size reduction and elimination. Examples of tumors undergoing angiogenesis include but are not limited to angiofibroma, arteriovenous malformations, ocular tumors, all solid tumors, Kaposi's sarcoma, trachoma and choriocarcinoma.

The peptides of the invention may be used to assess and/or modulate the development of the vasculature of the placenta. Regulation of placental vascularization has important clinical implications, since two disorders of pregnancy, preeclampsia and intrauterine growth retardation, are associated with impairment of vascular development. No clinical tests exist to predict the occurrence of these disorders until pregnancy is seriously compromised. The peptides of the invention can also be used as contraceptive agents.

Production of the Peptides of the Invention

The peptides of the current invention can, for example, be synthesized, prepared from purified full-length hormones, or produced using recombinant methods and techniques known in the art. Although specific techniques for their preparation are described herein, it is to be understood that all appropriate techniques suitable for production of these peptides are intended to be within the scope of this invention.

Generally, these techniques include DNA and protein sequencing, cloning, expression and other recombinant engineering techniques permitting the construction of prokaryotic and eukaryotic vectors encoding and expressing each of the peptides of the invention.

In one mode, the peptides of this invention are conveniently obtained by isolation of intact growth hormone from the human pituitary gland or plasma and isolation of placental lactogen and growth hormone variant hGH-V. The isolated intact hormones may be glycosylated and cleaved to varying degrees.

In another mode, the peptides may be prepared by peptide synthesis according to method described in *Biotechnology and Applied Biochem.*, 12:436 (1990) or by methods described in *Current Protocols in Molecular Biology*, Eds. Ausubel, F. M., et al, John Wiley & Sons, N.Y. (1987).

The peptides of the invention may be produced by expression of a nucleic acid encoding a peptide of interest, or by cleavage from a longer length polypeptide encoded by the nucleic acid. Expression of the encoded polypeptides may be done in bacterial, yeast, plant, insect, or mammalian hosts by techniques well known in the art. As for example, 16K hPRL has been produced in eukaryotic HCT 116 cells. The cDNA coding for the 16K hPRL (stop 140) has been cloned into the mammalian expression vector pRC-CMV. The construct was transferred into the HCT116 human colon cancer cells and stably transfected cells expressing 16K hPRL (stop 140) were obtained. Either conditioned media or purified 16K hPRL (stop 140) from these cells were able to inhibit bFGF-induced bovine endothelial cell proliferation.

In an embodiment, a peptide of interest of the invention is obtained by cloning the DNA sequence into a Vector starting with a DNA codon for methionine inserted upstream of 5' to the first DNA codon of the desired antiangiogenic tilted peptide sequence and modifying the DNA codon corresponding to the last amino acid of a desired antiangiogenic tilted peptide to a stop codon by mutagenesis techniques known in the art. A host cell is transformed with the modified nucleic acid to allow expression of the encoded peptide. In a further embodiment, the cloned hormone DNA is engineered to create a proteolytic cleavage site within the hormone polypeptide. The polypeptide is then cleaved after production in the host to generate the peptide of interest. Examples of mutagenesis techniques include, for example, methods described in *Promega Protocols and Applications GWde*, Promega Corp, Madison, Wis., p. 98 (1891) or according to *Current Protocols in Molecular Biology*, supra.

If the peptide is to be synthesized via a prokaryotic vector, the DNA sequence encoding an antiangiogenic tilted peptide preferably does not contain a signal peptide sequence. In addition, a DNA codon for methionine (Met) is typically inserted upstream of 5' to the first DNA codon of the coding sequence.

The peptides of the invention may be produced as an hybrid or a fusion protein made with a protein and the antiangiogenic peptide. As for example, an antiangiogenic tilted peptide of 16K hPRL has been produced as fusion with the maltose binding protein. The DNA fragment encoding the antiangiogenic tilted peptide of 16K hPRL has been cloned into the pMAL-C2x plasmid so that an in-frame protein fusion between the maltose binding protein and the antiangiogenic tilted peptide of 16K hPRL is produced. This fusion protein is able to induce apoptosis of endothelial cells.

Methods for cloning DNA into a vector and for inserting, deleting and modifying polynucleotides and for site directed mutagenesis are described, for example, in *Promega Protocols and Applications Guide*, supra. Cells or bacteria may be transfected with a vector, preferably with an expression vector, having the desired DNA sequence attached thereto, by known techniques including heat shock, electroporation, calcium phosphate precipitation and lipofection, among others. The terminal peptides or other analogues or fragments may then be extracted and purified by, for example, high pressure liquid chromatography (HPLC), ion exchange chromatography or gel permeation chromatography. However, other methods and techniques known in the art of conducting the different steps or combinations of these steps necessary to derive the peptide of this invention or equivalent steps are contemplated to be within the scope of this invention.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch J. Mol. Biol. 48:443 (1970), by the search for similarity method of Pearson and Lipman Proc. Natl. Acad. Sci. U.S.A. 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

Nucleic Acids of the Invention

Also provided herein are isolated nucleic acids that comprise DNA or RNA sequences (polynucleotides) encoding the peptides of the invention. The nucleic acids of the invention may further comprise vectors for expression of the peptides of the invention. In some embodiments the DNA may comprise cDNA sequences encoding antiangiogenic tilted peptide. It is understood by one of ordinary skill in the art that because of degeneracy in the genetic code, substitutions in the nucleotide sequence may be made which do not result in changes in the encoded amino acid sequence. Thus, "substantially identical" sequences as defined herein are included in the scope of the invention. It is further understood by one of ordinary skill in the art that both complementary strands of any DNA molecule described herein are included within the scope of the invention.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

Agonists

In some embodiments of the invention, agonists of the receptor(s) for the antiangiogenic peptides are provided. Such agonists include but are not limited to mutants of the peptides of the invention and peptide, non-peptide, and peptidomimetic analogs of the peptides of the invention.

Treatment Protocols

The method for treatment of angiogenic diseases comprises administering to a patient an angiogenesis inhibitory amount of one or more peptides of the invention. As used herein, the term "treatment" is intended to refer to the prevention, amelioration, or reduction in severity of a symptom of angiogenesis. Similarly, an angiogenic-inhibitory effective dose of a peptide of the invention is a dose sufficient to prevent, ameliorate, or reduce the severity of a symptom of angiogenesis.

The peptides of the invention may be administered singly or in combination with each other or other angiogenesis inhibitory agents. Typically, the peptides of the invention are administered in an amount of about 8 micrograms to 3,000 µg/kg per day, and more preferably about 20 to 1,500 µg/kg per day preferably once or twice daily. However, other amounts, including substantially lower or higher amounts, may also be administered. The peptides of the invention are administered to a human subject in need of antiangiogenic treatment intramuscularly, subcutaneously, intravenously, intratumorally, by any other acceptable route of administration. In the case of ocular angiogenic diseases, the peptide may also be administered topically to the eye.

Both preventative or therapeutic uses, such as the prevention and/or treatment of diabetic patients to avoid a decrease of their vision produced by vascularization of the retina, contraceptive applications, and the long-term treatment of cancer patients such as for avoiding the reformation of malignant tumors after surgery or chemotherapy are intended.

As it is well-known that some patients, e.g. diabetic patients, suffer from vision loss over a period of time, the present peptide may be suitably utilized for the inhibition or retardation of this process. When utilized for this application, the composition of the invention to be administered may comprise an amount of the peptide about 12 to 3,500 µg/kg per day, and preferably about 25 to 2,700 µg/kg per day. However, different amounts of the peptide may also be administered as seen suitable by a practitioner for specific cases. Smaller amounts may be administered by injection into the anterior chamber of the eye.

For this or any other application the peptide of this invention may be administered in an amount of about 10 to 3,750 µg/kg, and more preferably about 15 to 1,600 µg/kg. Any means of administration is suitable.

The antiangiogenic tilted peptide may be used in combination with other compositions and procedures for treatment of diseases. For example, a tumor may be treated conventionally with surgery, radiation or chemotherapy combined with the antiangiogenic tilted peptide and then the antiangiogenic tilted peptide may be subsequently administered to the patient to extend the dormancy of micrometastasis and to stabilize any residual tumor.

Gene Therapy

Gene therapy utilizing recombinant DNA technology to deliver nucleic acids encoding peptides of the invention into patient cells or vectors which will supply the patient with gene product in vivo is also contemplated within the scope of the present invention.

Gene therapy techniques have the potential for limiting the exposure of a subject to a gene product, such as polypeptide, by targeting the expression of the therapeutic gene to a tissue of interest, such as skeletal muscle, myocardium, vascular endothelium or smooth muscle, or solid or circulating tumor cells. For example, WIPO Patent Application Publication No. WO 93/15609 discloses the delivery of interferon genes to vascular tissue by administration of such genes to areas of vessel wall injury using a catheter system. In another example, an adenoviral vector encoding a protein capable of enzymatically converting a prodrug, a "suicide gene", and a gene encoding a cytokine are administered directly into a solid tumor.

Other methods of targeting therapeutic genes to tissues of interest include the three general categories of transductional targeting, positional targeting, and transcriptional targeting (for a review, see, e.g., Miller et al. FASEB J. 9:190-199 (1995)). Transductional targeting refers to the selective entry into specific cells, achieved primarily by selection of a receptor ligand. Positional targeting within the genome refers to integration into desirable loci, such as active regions of chromatin, or through homologous recombination with an endogenous nucleotide sequence such as a target gene. Transcriptional targeting refers to selective expression attained by the incorporation of transcriptional promoters with highly specific regulation of gene expression tailored to the cells of interest.

Examples of tissue-specific promoters include a liver-specific promoter (Zou et al., Endocrinology 138:1771-1774 (1997)); a small intestine-specific promoter (Oliveira et al., J. Biol. Chem. 271:31831-31838 (1996)); the promoter for creatine kinase, which has been used to direct of dystrophin cDNA expression in muscle and cardiac tissue (Cox et al., Nature 364:725-729 (1993)); and immunoglobulin heavy or light chain promoters for the expression of suicide genes in B cells (Maxwell et al., Cancer Res. 51:4299-4304 (1991)). An endothelial cell-specific regulatory region has also been characterized (Jahroudi et al., Mol. Cell, Biol. 14:999-1008 (1994)). Amphotrophic retroviral vectors have been constructed carrying a herpes simplex virus thymidine kinase gene under the control of either the albumin or alpha-fetoprotein promoters (Huber et al., Proc. Natl. Acad. Sci. U.S.A. 88:8039-8043 (1991)) to target cells of liver lineage and hepatoma cells, respectively. Such tissue specific promoters can be used in retroviral vectors (Hartzoglou et al., J. Biol. Chem. 265:17285-17293 (1990)) and adenovirus vectors (Friedman et al., Mol. Cell. Biol. 6:3791-3797 (1986)) and still retain their tissue specificity.

Other elements aiding specificity of expression in a tissue of interest can include secretion leader sequences, enhancers, nuclear localization signals, endosmolytic peptides, etc. Preferably, these elements are derived from the tissue of interest to aid specificity.

Viral vector systems useful in the practice of the instant invention include but are not limited to adenovirus, herpesvirus, adeno-associated virus, minute virus of mice (MVM), HIV, sindbis virus, and retroviruses such as Rous sarcoma virus, and MoMLV. Typically, the nucleic acid encoding the therapeutic polypeptide or peptide of interest is inserted into such vectors to allow packaging of the nucleic acid, typically with accompanying viral DNA, infection of a sensitive host cell, and expression of the polypeptide or peptide of interest.

For example, the DNA constructs of the invention can be linked through a polylysine moiety to asialo-oromucoid, which is a ligand for the asialoglycoprotein receptor of hepatocytes (Chem. 263:14621-14624 (1988); WO 92/06180).

Similarly, viral envelopes used for packaging the recombinant constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel et al., Proc. Natl. Acad. Sci. U.S.A. 88:8850-8854 (1991)). In other embodiments, molecular conjugates of the instant invention can include microtubule inhibitors (WO 94/06922); synthetic peptides mimicking influenza virus hemagglutinin (Plank et al., J. Biol. Chem. 269:12918-12924 (1994)); and nuclear localization signals such as SV40 T antigen (WO 93/19768).

The nucleic acid can be introduced into the tissue of interest in vivo or ex vivo by a variety of methods. In some embodiments of the invention, the nucleic acid is introduced into cells by such methods as microinjection, calcium phosphate precipitation, liposome fusion, or biolistics. In further embodiments, the nucleic acid is taken up directly by the tissue of interest. In other embodiments, nucleic acid is packaged into a viral vector system to facilitate introduction into cells.

In some embodiments of the invention, the compositions of the invention are administered ex vivo to cells or tissues explanted from a patient, then returned to the patient. Examples of ex vivo administration of gene therapy constructs include Axteaga et al., Cancer Research 56(5):1098-1103 (1996); Nolta et al., Proc Natl. Acad. Sci. USA 93(6): 2414-9 (1996); Koc et al., Seminars in Oncology 23 (1):46-65 (1996); Raper et al., Annals of Surgery 223(2):116-26 (1996); Dalesandro et al., J. Thorac. Cardi. Surg. 11(2):416-22 (1996); and Makarov et al., Proc. Natl. Acad. Sci. USA 93(1): 402-6 (1996).

Formulations and Pharmaceutical Compositions

The peptides of the current invention can, for example, be synthesized, prepared from purified full-length hormones, or produced using recombinant methods and techniques known in the art. In a preferred embodiment the tilted peptide can be fused to a carrier polypeptide/protein as for example the "maltose binding protein" (MBP) and produced using recombinant method. For example, fusion protein made from peptide of scorpion venom and MBP was used as antigens to successfully produce antibodies in rabbit (Legros, C., et al. Vaccine 20:934-42 (2001)). This shows that these fusion proteins can be successfully used as a vaccine providing efficient immune protection against A. Australis venom. Alternatively, the tilted peptide can be synthesized and then fused to a carrier molecule to improve its efficiency. In an alternative embodiment the peptides of the present invention or the recombinant protein comprising said peptide are pegylated. Pegylation is the conjugation of peptides or polypeptides with polyethylene glycol. Pegylated alpha interferon has used as a treatment for mice infected by the Venezuelan equine encephalitis virus (VEEV). The use of pegylated interferon results in greatly enhanced survival to infection to VEEV (Lukaszewski, R. A. and Brooks, T. J. J. Virol 74:5006-15 (2000)). In human therapy, pegylated interferon is currently an efficient treatment of chronical infection with hepatitis C virus (Poynard, T., et al. Lancet 362:2095-100 (2003)).

Concerning a method to experimentally determine if a peptide is tilted: The characteristic of a tilted peptide is to induce liposome fusion in in vitro experiments. This method has been described in (Martin, I., et al. Biochem Biophys Res Commun 175:872-9 (1991)), (Pillot, T., et al. J Biol Chem 271:28757-65 (1996)), (Pillot, T., et al. J Mol Biol 274:381-93 (1997)), (Lins, L., et al. Protein Eng 15:513-20 (2002)).

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human .dosage. Various considerations are described, for example, in *Goodman and Gilman's the Pharmacological Basis of Therapeutics,* 7th Edition (1985), MacMillan Publishing Company, New York, and *Remington's Pharmaceutical Sciences* 18*th Edition,* (1990) Mack Publishing Co, Easton Pa. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety in, e.g., Szoka et al. Ann. Rev. Biophys. Bioeng. 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well-known in the art. Similarly, the compositions can be delivered via a pump to a tissue of interest.

The compositions of the invention are typically administered to patients after the onset of symptoms, although treatment can also be prophylactic in some embodiments. Typically, treatment with direct administration of polypeptides is done daily, weekly, or monthly, for a period of time sufficient to reduce, prevent, or ameliorate symptoms. Treatment with the nucleic acids of the invention is typically done at intervals of several months. In some embodiments, administration of the compositions of the invention is done in utero.

The composition of the invention may also be provided in the kit as a slow-release composition such as a daily, weekly, monthly unit provided as a sponge, dermal patch, subcutaneous implant and the like in a wrapping or container as described above. In this case, the patient may release a unit of the composition from the container and applies it as indicated in the kit instructions. The composition may then be replaced at the end of the specified period by a fresh unit, and so on.

The present composition may also be administered by means of injection, as indicated above. Typically, the peptide may be administered by itself, or, for instance, in the case of a diabetic, in a composition also comprising insulin. The same is true for the slow-release forms of the composition. Similarly, the peptide of the invention may be administered in a composition that also comprises another drug. One such case is that of cancer patients, where different anticancer drugs such as chemotherapeutic or contrast agents and target-specific antibodies, among others, may be provided in a composition also comprising the peptide of the invention. The proportion of peptides to the other drug(s) and carrier may be adjusted accordingly.

The levels of the delivered peptide to a patient may be monitored by immunoassay. To determine the level of the peptide of invention in blood following administration, e.g., intramuscular or subcutaneous administration, an antibody assay may be performed with antibodies specific to the peptide sequence by any of the protocols known in the art. Polyclonal or monoclonal antibodies or the 16K N-terminal fragment receptor may be utilized. The level of the peptide in blood may then be correlated with the progress of the inhibition of any of the diseases the patient is afflicted with.

FIGS. 1(A-B): Panel (A) shows a protein sequence of hPRL (SEQ ID NO: 14). The hPRL protein contains two tilted peptides: the region which is likely to adopt a tilted peptide structure is highlighted in bold ($1^{st}$ tilted peptide SEQ ID NO: 3) and in italics ($2^{nd}$ tilted peptide SEQ ID NO: 8). Alpha-helical regions are indicated by underlining (Keeler, C., et al. J Mol Biol 328:1105-21 (2003)). Panel (B) is an alignment of the tilted peptide regions in the 16K fragments of the PRL/GH family.

Figure 3:
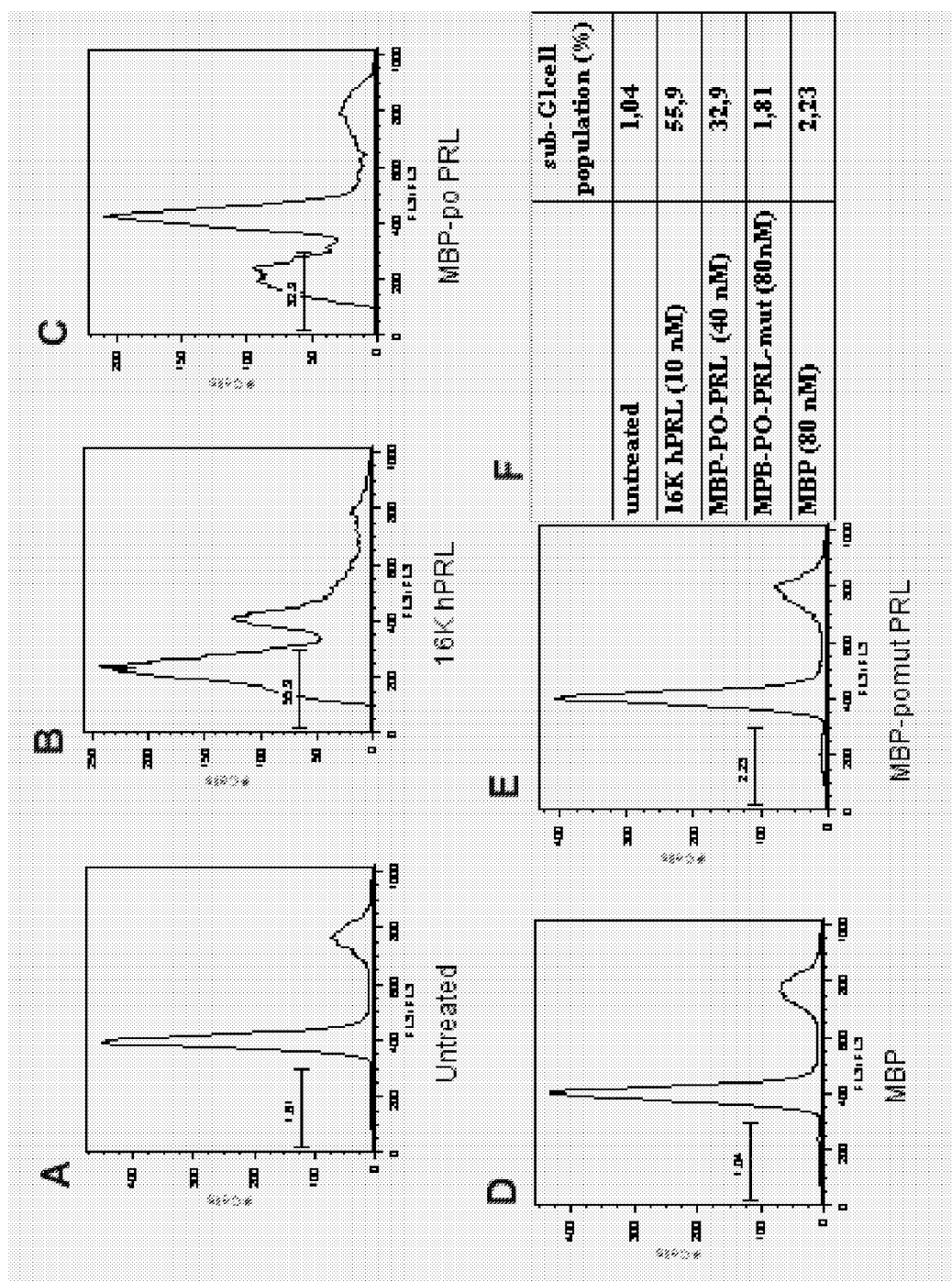
FIG. 3 shows the analysis of the induction of apoptosis by flow cytometry according to example 3.6.1. BACE cells were left untreated (A), or treated with 10 nM E. coli-produced 16K hPRL (B), 40 nM MBP-PO-PRL (C), 80 nM MBP (D) or 80 nM MBP-POmut-PRL(E).

FIGS. 3(A-F) shows the analysis of the induction of apoptosis by flow cytometry according to example 3.6.1. BACE cells were left untreated, Panel (A): or treated with 10 nM E. coli-produced 16K hPRL, Panel (B): 40 nM MBP-PO-PRL, Panel (C): 80 nM MBP, Panel (D): or 80 nM MBP-POmut-PRL, (E). The percentage of sub G1 cell population for each of (A)-(E) is summarized in Panel (F).

Figure 9:
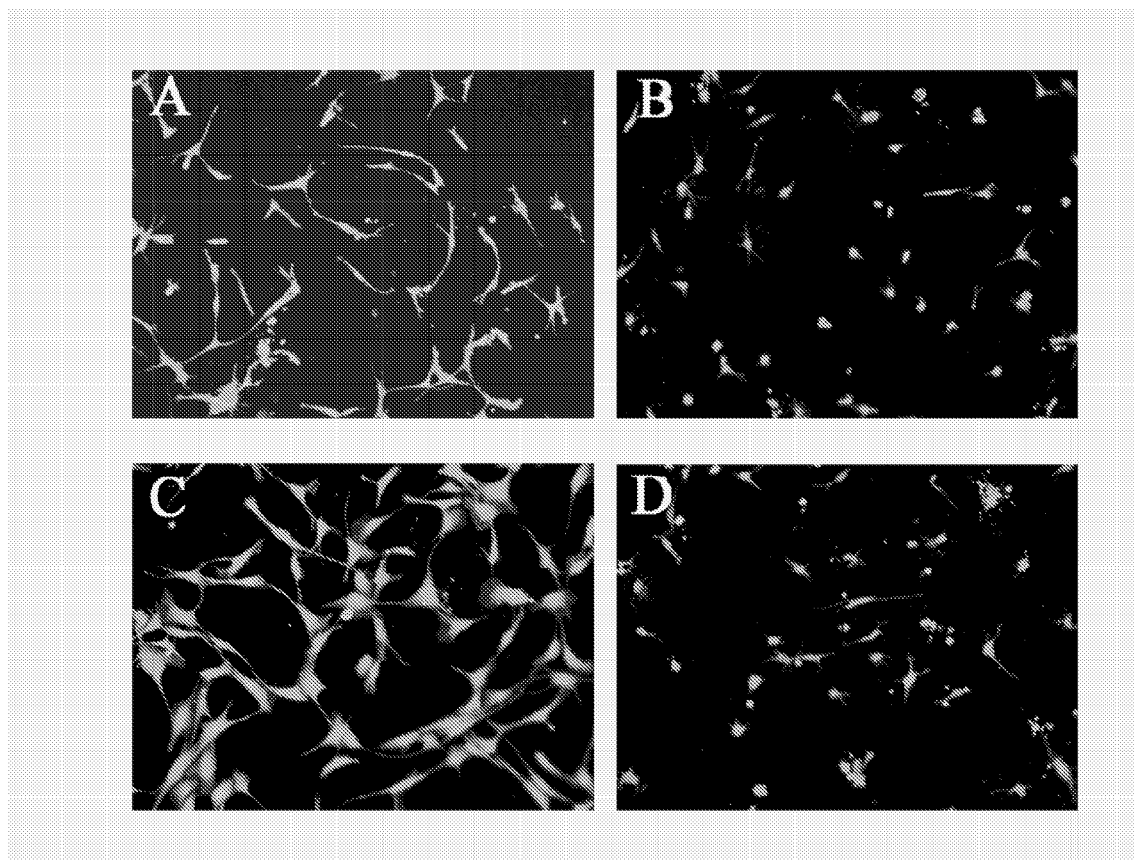
FIG. 9 shows that MBP-PO-PRL inhibits capillary formation in vitro in the collagen gel assay according to example 3.6.4. Panel A: untreated cells, panel B: 10 nM 16K hPRL, panel C: 40 nM MBP-PO-PRL, panel D: 80 nM MBP-PO-mut-PRL.

FIGS. 9(A-D) shows that MBP-PO-PRL inhibits capillary formation in vitro in the collagen gel assay according to example 3.6.4. Panel A: untreated cells, panel B: 10 nM 16K hPRL, panel C: 40 nM MBP-PO-PRL, panel D: 80 nM MBP-POmut-PRL.

FIGS. 10(A-B) shows that MBP-PO-PRL inhibits capillary formation in vivo in the chick chorioallantoic membrane assay according to example 3.6.5. Panel A: chick chorioallantoic membrane images; Panel B: graphical summary of avascular areas.

Figure 11:
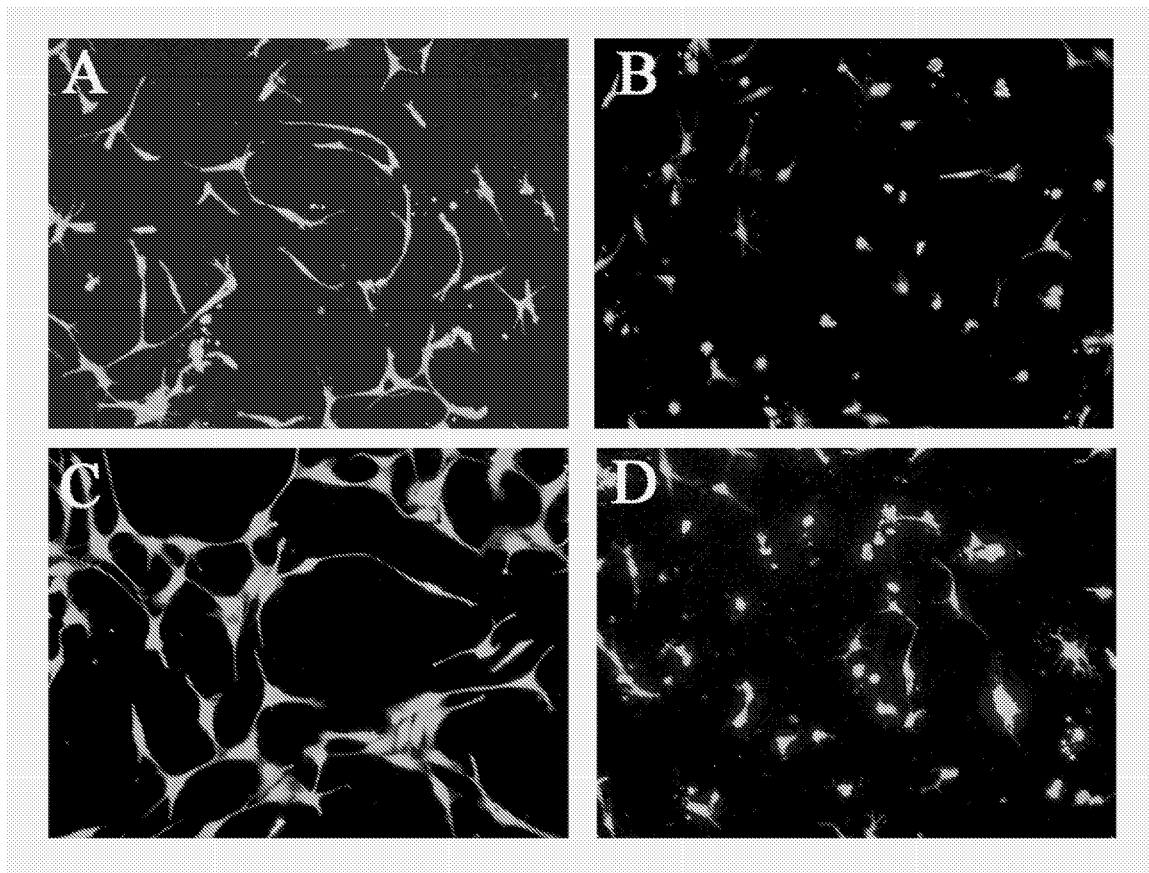
FIG. 11 shows that MBP-PO-GH inhibits capillary formation in vitro in the collagen gel assay according to example 4.2.3. Panel A: untreated cells, panel B: 10 nM 16K hPRL, panel C: 80 nM MBP-PO-GH, panel D: 160 nM MBP-PO-mut-GH.

FIGS. 11(A-D) shows that MBP-PO-GH inhibits capillary formation in vitro in the collagen gel assay according to example 4.2.3. Panel A: untreated cells, panel B: 10 nM 16K hPRL, panel C: 80 nM MBP-PO-GH, panel D: 160 nM MBP-POmut-GH.

FIGS. 12(A-B) shows that MBP-PO-GH inhibits capillary formation in vivo in the chick chorioallantoic membrane assay according to example 4.2.4. Panel A: chick chorioallantoic membrane images; Panel B: graphical summary of avascular areas.

Figure 14:
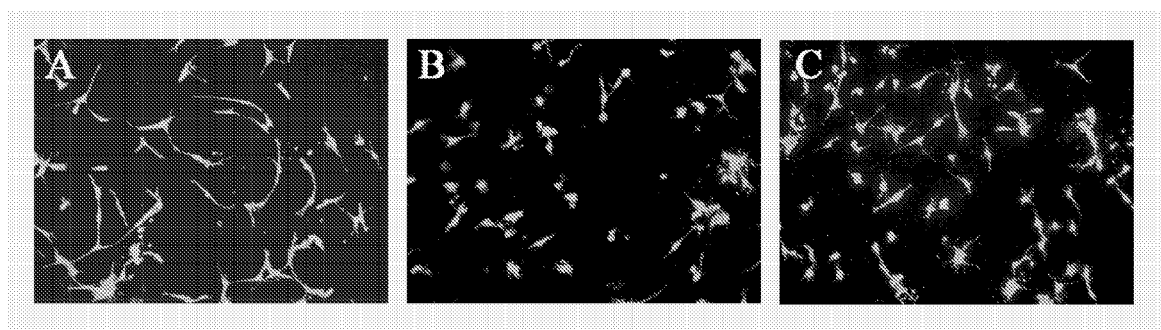
FIG. 14 shows that MBP-PO-SIV and MBP-PO-BA inhibit capillary formation in vitro in the collagen gel assay according to example 6.2.3. Panel A: untreated cells, panel B: 160 nM MBP-PO-SIV, panel C: 160 nM MBP-PO-BA.

FIGS. 14(A-C) shows that MBP-PO-SIV and MBP-PO-BA inhibit capillary formation in vitro in the collagen gel assay according to example 6.2.3. Panel A: untreated cells, panel B: 160 nM MBP-PO-SIV, panel C: 160 nM MBP-PO-BA.

Figure 15:
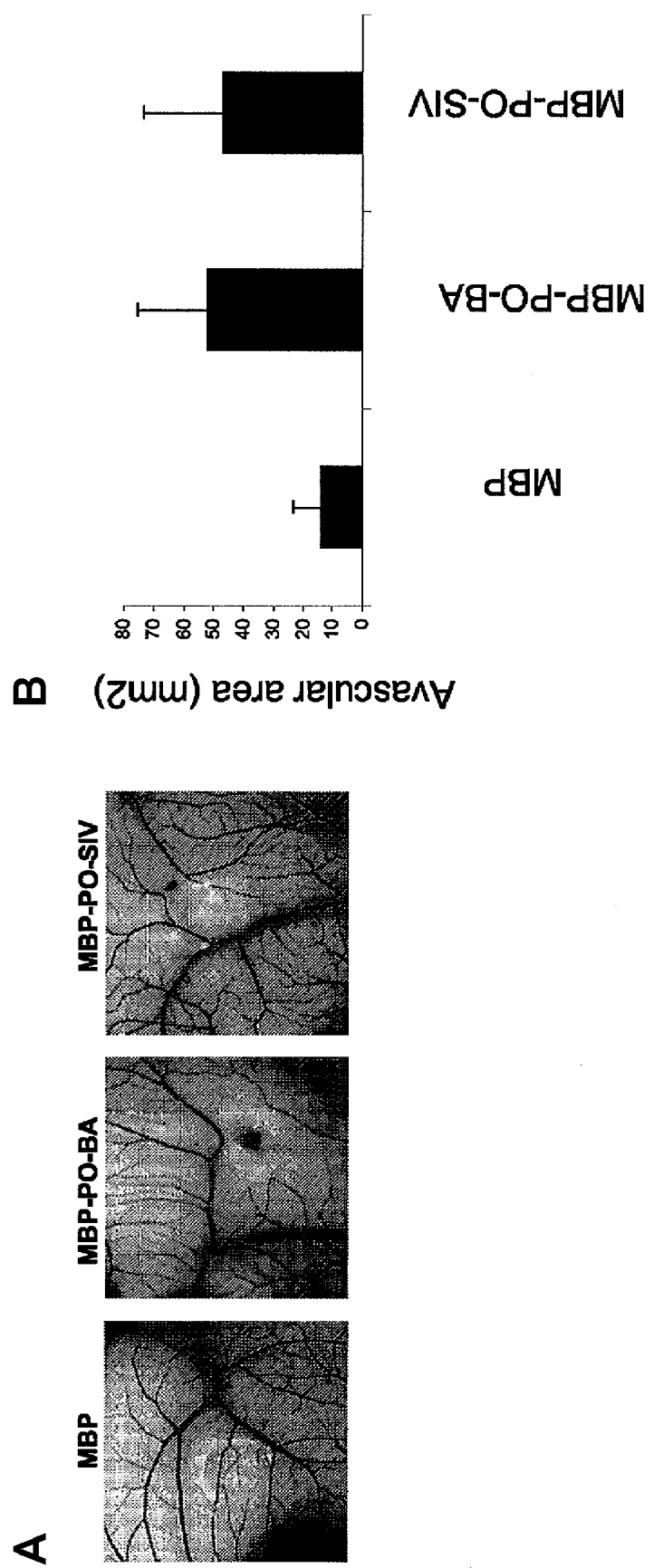
FIG. 15 shows that MBP-PO-SIV and MBP-PO-BA inhibit capillary formation in vivo in the chick chorioallantoic membrane assay according to example 6.2.4.

FIGS. 15(A-B) shows that MBP-PO-SIV and MBP-PO-BA inhibit capillary formation in vivo in the chick chorioallantoic membrane assay according to example 6.2.4. Panel A: chick chorioallantoic membrane images; Panel B: graphical summary of avascular areas.

Figure 16:
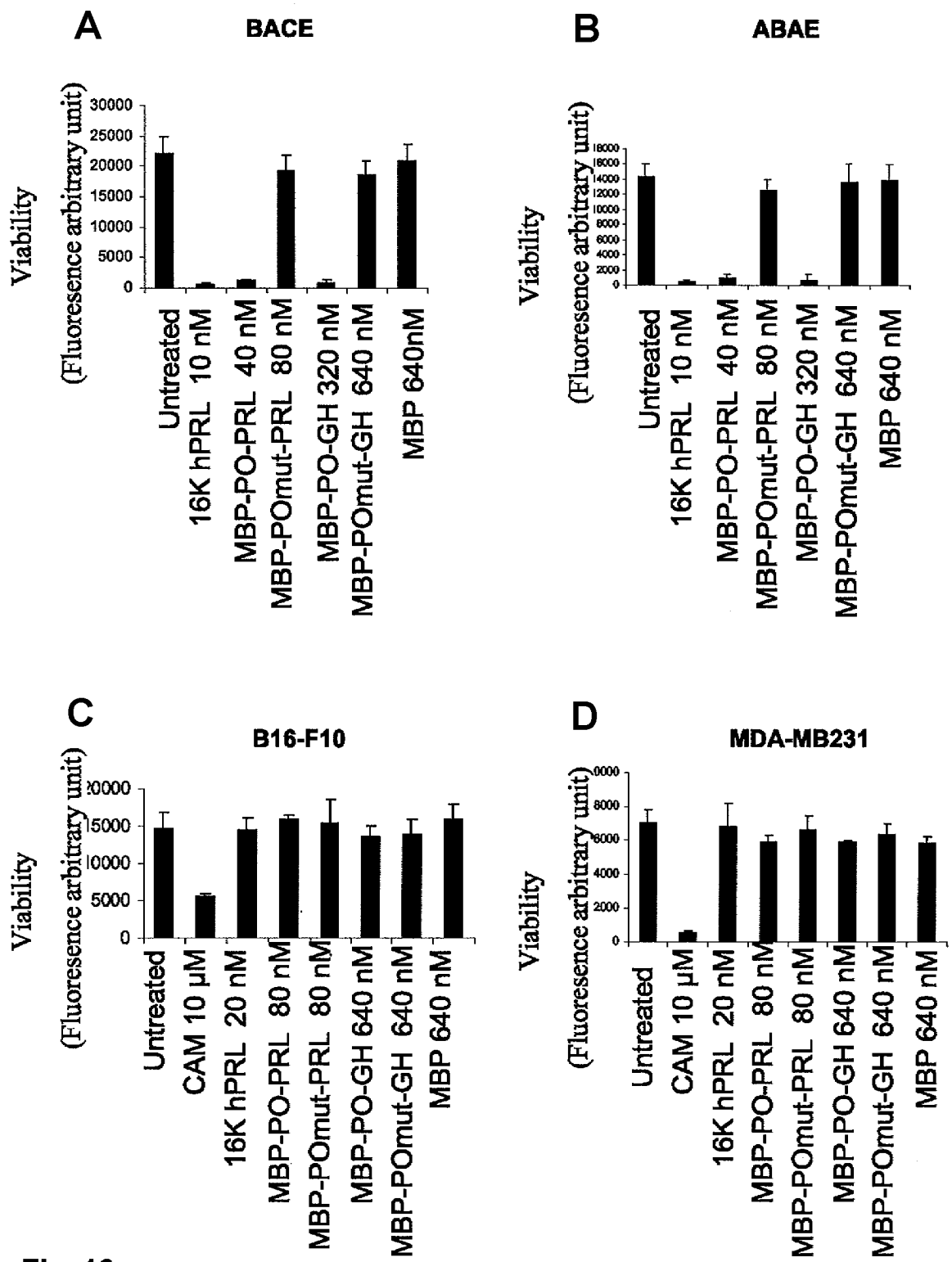
FIG. 16 shows that MBP-PO-PRL and MBP-PO-GH reduce viability of endothelial cells (BACE and ABAE cells) but not of tumoral (B16-F10 and MDA-MB-231) cells according to example 7.

FIGS. 16(A-D) shows that MBP-PO-PRL and MBP-PO-GH reduce viability of endothelial cells (BACE and ABAE cells) but not of tumoral (B16-F10 and MDA-MB-231) cells according to example 7. Panel A: BACE; Panel B: ABAE; Panel C: B16-F10; Panel D: MDA-MB231.

FIGS. 17(A-B) shows that 16K hPRL fused to MBP and mutated in its tilted peptide region (MBP-16K hPRLmut) (panel A) is less able to induce caspase 3 activation in endothelial cells than unmutated 16K hPRL fused to MBP (MBP-16K hPRL) according to example 8. Mutation of both tilted peptides of 16 K hPRL completely abolishes 16 K hPRL activity (panel B) (Example 8.3 and 8.4).

FIGS. 18(A-B) shows that 16K hPRL is monomeric in denaturating condition but trimeric in native conditions according to example 9. Panel A: 17% polyacrylamide SDS-PAGE of 16K hPRL. Lane 1-3: SDS-PAGE in the presence of β-ME. Lane 1: purified 16K hPRL. Lane 2: molecular weight marker. Lane 3: protein unrelated to this topics. Lanes 4: SDS-PAGE in the absence of β-ME: purified 16K hPRL. To the right, molecular weight of the marker are shown (in kDa). Panel B: Analytical size exclusion chromatography of 16K hPRL on a Superose 12 molecular sieve A: Calibration of the column with Dextran blue (peak 1), dimeric (peak 2) and monomeric BSA (peak 3), ovalbumin (peak 4) and myoglobin (peak 5); B: 16K hPRL.

The following examples are intended to illustrate, not limit the scope of this invention.

EXAMPLES

Example 1

Identification of a Tilted Peptide Region in the PRL/GH 16K Fragments

A general procedure of molecular modelling was set up that allows the detection of tilted peptides in a given protein sequence (Brasseur, R. Mol Membr Biol 17:31-40 (2000)). Briefly, tilted peptides are detected in a protein sequence using the following criteria: a) the peptide is 10 to 20 amino acids long, b) the mean hydrophobicity of the peptide (as calculated by the Eisenberg scale consensus scale in Eisenberg, D, Weiss, R, Terwillinger, T 1982, Nature, 299, 371-374) is higher than 0.1; c) the hydrophobicity along the sequence is analyzed using different methods such as the Jähnig and Hydrophobic Cluster Analysis methods (Gaboriaud, C., et al. FEBS Lett 224:149-55 (1987), Jahnig, F. Trends Biochem Sci 15:93-5 (1990)); d) when the peptide is built as a α helix, the angle between the helix axis and the interface plane is between 30° and 70° e) the minimal energy conformation is oriented at the hydrophobic/hydrophilic interface. f) Molecular Hydrophobicity Potentials are calculated and the hydrophobic isopotential envelopes are asymmetric.

Using this procedure, a potential tilted peptide was detected in each the human PRL/GH 16K fragment sequences. This domain is conserved, in terms of obliquity properties, among the sequences of the four 16K fragments.

FIG. 1 shows in A, the protein sequence of hPRL. The region likely to adopt a tilted peptide structure is highlighted in bold. Alpha-helical regions are shown inside rectangles (Keeler, C., et al. J Mol Biol 328:1105-21 (2003)). The arrow indicates the localization of 16K fragments cleavage site. B shows the alignment of the tilted peptide regions in the 16K fragments of the PRL/GH family.

Example 2

Chemical Synthesis of Peptides 2.1. Synthesis of the PO-PRL Peptide

The peptide named PO-PRL corresponding to the tilted peptide region of the 16K hPRL was chemically synthesized. The sequence is FLSLIVSILRSWNE (SEQ ID NO: 3). This peptide was synthesized by the Eurogentec S.A., a private biotech company. The peptide has its N terminus acetylated and C terminus amidated.

2.2. Biophysical Characterization of Tilted Peptides: Lipid Phase Fusion

Lipid phase fusion was measured by following the fluorescence of a liposoluble marker, R18. When incorporated into liposomes at a high surface density, R18 fluorescence is attenuated. Upon dilution of the marker through membrane fusion of labeled and unlabeled liposomes, the attenuation is relieved and R18 fluorescence increases. Labeled liposomes were prepared by blending R18 into the lipid film (see table 1). Labeled and unlabeled liposomes were mixed in a 1:4 ratio (w/w) and diluted to a concentration of 50 μM. Fluorescence is measured at room temperature (excitation λ: 560 nm, emission λ: 590 nm) on a Perkin Elmer LS-50B fluorimeter. The ability of PO-PRL to induce liposome fusion was analyzed in two different liposome preparations at different pH (table 1).

TABLE 1

Composition and preparation of LUV (large unilamellar vesicles). LUV were prepared by extrusion. Briefly, the lipid film was hydrated for one hour at 37 ° C. The suspension was subjected to 5 freeze and thaw cycles followed by 10 successive passages through 2 polycarbonate filters (0.08 μm pore diameter), under a 20 bar nitrogen pressure. Phospholipid concentration was determined by phosphate dosage (Barlett's method).

| Lipid | Uncharged unlabeled liposomes Percentage (w/w) | Uncharged labeled liposomes Percentage (w/w) | Lipid | Charged unlabeled liposomes Percentage (w/w) | Charged labeled liposomes Percentage (w/w) |
|---|---|---|---|---|---|
| PC | 26.6% | 24.9% | PC | 30% | 28.45% |
| PE | 26.6% | 24.9% | PE | 30% | 28.45% |
| SM | 26.6% | 24.9% | PS | 10% | 2.37% |
| CHOL | 20.2% | 18.9% | PI | 2.5% | 9.48% |
| R18 | | 6.3% | SM | 5% | 4.74% |
| | | | CHOL | 22.5% | 21.33% |
| | | | R18 | | 5.18% |

The following buffers were used: pH 8 buffer (10 mM Tris-HCl, pH=8; 150 mM NaCl; 0.01% EDTA; 1 mM NaN$_3$), pH 6 buffer (10 mM Sodium-Acetate, pH=6; 150 mM NaCl; 0.01% EDTA; 1 mM NaN$_3$), pH 4 buffer (10 mM Sodium Acetate, pH=4; 57 mM Acetic Acid)

The following concentrations of the peptide were used:

600 μM corresponding to a molar peptide/lipid ratio (R) of 0.2

300 μM corresponding to a peptide/lipid ratio (R) of 0.1

150 μM corresponding to a peptide/lipid ratio (R) of 0.05

60 μM corresponding to a peptide/lipid ratio (R) of 0.02

30 μM corresponding to a peptide/lipid ratio (R) of 0.01.

Whatever the experimental condition used (charged or uncharged liposomes, pH=4, 6 or 8), the PO peptide induces liposome fusion in lipid phase. Induction of liposome fusion is dose-dependent. Table 2 shows percentages of relative fusion (after 15 min) for both peptides in the different experimental conditions.

TABLE 2

Relative liposome fusion induced by the PO peptide after 15 min. R = peptide/lipid ratio, C = charge and UC = uncharged liposomes. The liposome fusion induced by the PO peptide (R = 0.2; pH = 8, UC) was arbitrary set up at 100%:

| Peptide | R | pH 8 UC | pH 8 C | pH 6 UC | pH 6 C | pH 4 UC | pH 4 C |
|---|---|---|---|---|---|---|---|
| PO | 0.2 | 100 | 64 | 68 | 87 | 97 | 47 |
| | 0.1 | 64 | 41 | 55 | 44 | 105 | 34 |
| | 0.05 | 38 | 34 | 38 | 35 | 100 | 35 |

2.3. Conformation of the Peptide

The conformation of the peptide in solution is analyzed by Fourier transformed infrared spectroscopy (ATR-FTIR). The sample (20 µg) is spread on a Germanium plate and spectra are recorded between 1800 and 1000 cm−1. The deconvolution of the 1700-1600 cm−1 area, corresponding to the amide I band, allows the determination of the secondary structure of the peptide (Goormaghtigh, E., et al. Biochim Biophys Acta 1422:105-85 (1999)). The secondary structure of the peptide is given Table 3. Tilted peptides are often in β structure in solution, while being helical in the presence of lipids (Martin, I., et al. Biochem Biophys Res Commun 175:872-9 (1991)).

TABLE 3 secondary structure of the peptide dissolved in 100% DMSO

| Secondary structure | Peptide PO-PRL |
|---|---|
| Beta | 63% |
| Alpha | 16% |
| Turn | 12% |
| Coil | 9% |

Example 3

Determination of the Antiangiogenic Activity of the Tilted Peptide of 16K hPRL Fused to the MBP Protein 3.1. Expression of MBO-PO-PRL and MBP-POmut-PRL Recombinant Fusion Proteins The tilted peptide fused to the "maltose binding protein" (MBP) was produced by a recombinant DNA technology approach. The gene encoding the fusion protein made of MBP with the tilted peptide of 16K hPRL was constructed as follows and named MPB-PO-PRL. As a control, mutations that modify the hydrophobic distribution were introduced in the tilted peptide of the 16K hPRL. These mutations modify the oblique orientation of the peptide when oriented at a lipid water interface. The modification of the PO sequence consists in the permutation of Leu2 and Asn13 and of Val6 and Ser 11. The gene encoding the fusion protein made of MBP with the mutated tilted peptide of 16K hPRL was constructed as follows and named MPB-POmut-PRL. The sequences of the peptides are:

```
PO of 16K hPRL:    FLSLIVSILRSWNE   (SEQ ID NO: 3)

POmut of 16K hPRL: FNSLISSILRVWLE   (SEQ ID NO: 10)
```

3.2. Construction of the pMBP-PO-PRL and pMBP-POmut-PRL Expression Vectors

Oligonucleotides (Eurogentec s.a.) encoding the desired peptide were inserted at the C terminus of the MBP coding sequence in the pMAL-c2x plasmid (New England Biolabs Inc.). The oligonucleotides have been designed to include the BamH I and Xmn I restrictions sites respectively upstream and downstream of the peptide-coding sequences. These sites allowed us to insert the peptide coding the oligonucleotide into the pMAL-c2x plasmid previously digested by BamH I and Xmn I. One clone for each construct was selected and named, respectively, pMBP-PO-PRL et pMBP-POmut-PRL. Sequences were verified by sequencing.

The oligonucleotide sequences which are used to construct the pMBP-PO-PRL and pMBP-POmut-PRL plasmids are shown below. Mutations are shown in bold. Part of the Xmn I restriction site harboured by the oligonucleotide is shown in italic. Part of the BamHI restriction site harboured by the oligonucleotide is underlined:

```
                                         SEQ ID NO: 17;
PO-PRL for
5'-ATTTCATTTCTGAGCCTGATAGTCAGCATATTGCGATCCTGGAATGA
GTGAG-3',;

SEQ ID NO: 18
PO-PRL rev
3'-TAAAGTAAAGACTCGGACTATCAGTCGTATAACGCTAGGACCTTACT
CACTCCTAG5';

SEQ ID NO: 19
PO mut-PRL for
5'-ATTTCATTTAACAGCCTGATATCCAGCATATTGCGAGTCTGGCTTGA
GTGAG-3';

SEQ ID NO: 20
PO mut-PRL rev
3'-TAAAGTAAATTGTCGGACTATAGGTCGTATAACGCTCAGACCGAACT
CACTCCTAG5';
```

3.3. Construction of a Vector that Allows the MBP Expression

In order to produce a MBP control protein (without any fused peptide), a stop codon was introduced downstream the MBP coding sequence and upstream the peptide insertion site. The pMAL-c2x plasmid was digested by BamHI et XmnI and ligated with annealed "stop for" (5'-ATTTCAT-GATGAGGTACCCTCGAGG-3', SEQ ID NO: 15) and "stop rev" (3'-TAAAGTACTACTCCATGGGAGCTCCCTAG-5', SEQ ID NO: 16) oligonucleotides. These oligonucleotides contain a stop codon and the Xho I restriction site. One clone was selected by XhoI digestion and named pMBP. The sequence was verified by sequencing. In the oligonucleotide sequences used to construct the pMBP plasmid the XhoI is shown in bold. The part of the Xmn I restriction site harboured by the oligonucleotide is shown in italic. The part of the BamHI restriction site harboured by the oligonucleotide is underlined.

3.4. Expression of the MBP and MBP-PO-PRL, MBP-POmut-PRL Fusion Proteins

The constructs pMBP-PO-PRL, pMBP-POmut-PRL and pMBP were transformed into E. coli TOP10F' cells. The culture was performed in glucose-containing LB medium and expression was induced by addition of IPTG. Samples were collected at different incubation times and analyzed by SDS-PAGE. In order to analyze the solubility of the MBP-PO-PRL, MBP-POmut-PRL and MBP proteins, the cells were collected 5 h after IPTG induction and disrupted in a French press. The lysates were centrifuged and the pellets and supernatants, were analyzed by 16% SDS-PAGE. As shown in FIG. 2, MBP-PO-PRL et MBP-POmut-PRL proteins are present to almost 90% in the soluble fraction. The letter "F" indicates the band of the fusion protein. The production was estimated by SDS-PAGE to be at around 45 mg/l of culture. Similar results were obtained with MBP. FIG. 2 shows an 12% SDS-PAGE analysis of the MBP-PO and MBP-POmut solubility 5 h after IPTG induction:

MM: molecular weight marker.

Lanes 1-2: MBP-PO-PRL cell lysate supernatant.

Lanes 3-4: MBP-POmut-PRL cell lysate supernatant

Lanes 5-6: MBP-PO-PRL cell lysate pellet

Lanes 7-8: MBP-POmut-PRL cell lysate pellet 1, 3, 5, 7: the equivalent of 150 µl of a O.D.=1 of culture was loaded. 2, 4, 6, 8: the equivalent of 300 µl of a O.D.=1 of culture was loaded

3.5. Purification of MBP and MBP-PO-PRL, MBP-PO-mut-PRL Proteins

MBP-PO-PRL, MBP-POmut-PRL and MBP were first purified by affinity chromatography. The soluble proteins were loaded onto an amylose affinity resin (New England Biolabs Inc.), washed and eluted with maltose. The fractions containing the protein of interest were collected and dialyzed overnight against Tris-HCl 20 mM, pH=7.5. The three samples were then purified by anion-exchange chromatography.

3.6. Biological Activity of the MBP-PO-PRL, MBP-POmut-PRL and MBP Proteins

3.6.1. MBP-PO-PRL Induces Apoptosis in Endothelial Cells

In order to determine the effect of MPB-PO-PRL on endothelial cell apoptosis, the inventors have analyzed the DNA content of MBP-PO-PRL treated cells by flow cytometry. For this purpose, DNA was labeled with propidium iodide. Bovine adrenal cortex endothelial (BACE) cells were plated in low-glucose Dulbbecco's modified Eagle's medium containing 10% fetal calf serum (FCS) and 100 U/ml penicillin/streptomycin per ml (10% FCS medium) at a density of cells $5 \times 10^5$/100 mm plate. 24 h after plating, cells were treated for 18 h with the proteins of interest. The cells were then harvested and fixed and permeabilized in ice-cold ethanol for 2 h before centrifugation and incubation (at 37° C. for 30 min) in PBS containing Rnase (5 µg/ml) and propidium iodide (50 µg/ml). The cells were analysed using a Coulter Epics XL flow cytometer.

Results are shown in FIG. 3. The graph obtained with untreated cells is typical of an asynchonized cell culture showing sub-G1, G0/G1, S, G2/M cells population. Position of the sub-G1 population is indicated by a bar. The presence of a sub-G1 population corresponds to the presence of apoptotic bodies which is a hallmark of apoptosis. Percentage of the sub-G1 cell population are shown in panel F. *E. coli*-produced 16K hPRL was used as a control. Results show that a 18-h treatment of cells with MBP-PO-PRL and 16K hPRL resulted in the percentage of sub-G1 cell population of respectively 32,9 and 55,9 whereas percentage sub-G1 population of untreated cells is only 1%. MBP or MBP-PO-PRL-mut treated cells values are not significantly different from untreated cells values.

3.6.2. MBP-PO-PRL Induces Caspase 3 Activation in Endothelial Cells

Figure 4:
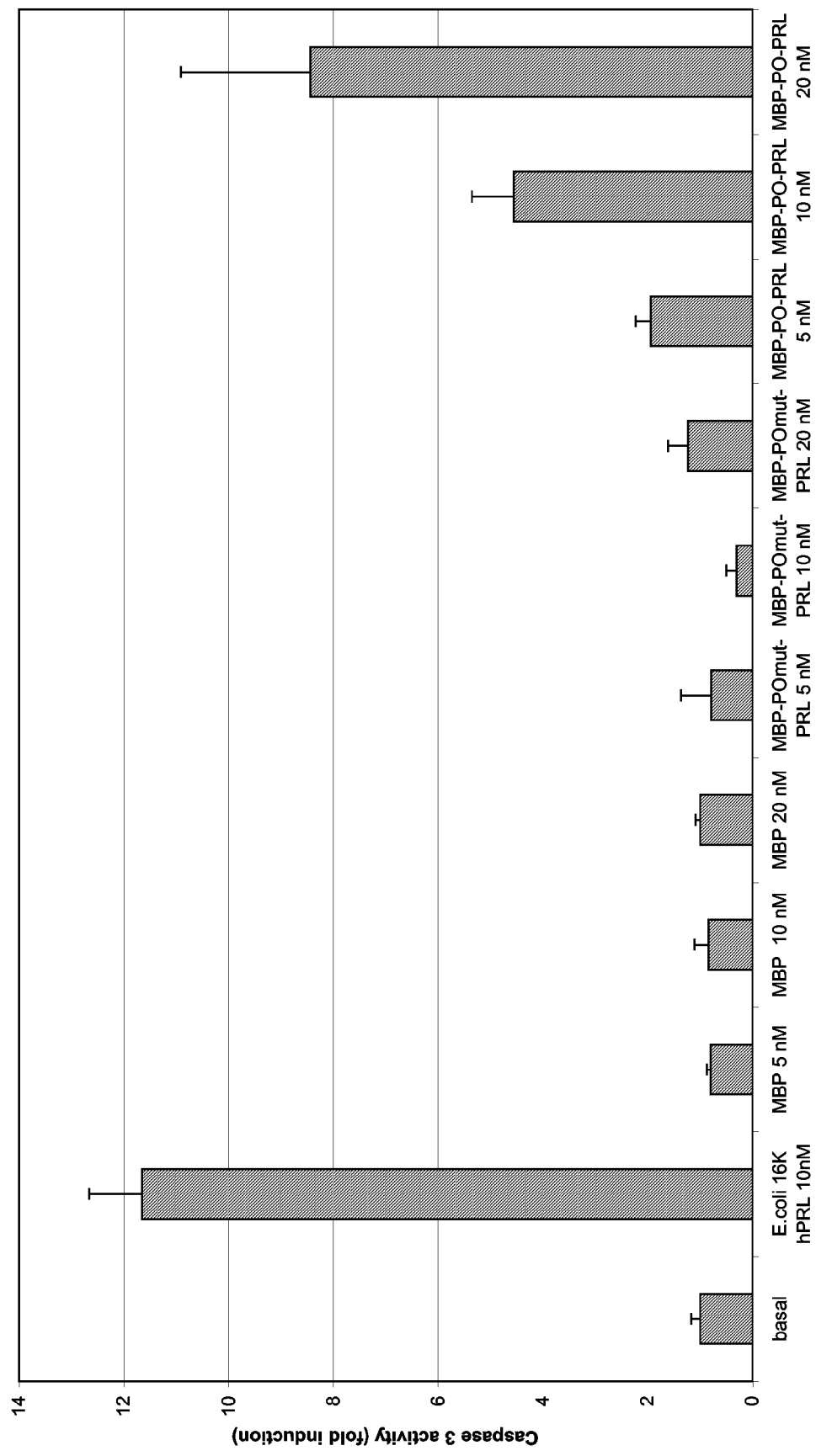
FIG. 4 shows the activation of Caspase 3 by the MBP-PO-PRL, MBP-POmut-PRL and MBP proteins according to example 3.6.2. Basal: untreated BACE cells. E.coli 16K hPRL: positive control.

To confirm that MBP-PO-PRL induces apoptosis in BACE cells, the inventors studied activation of the caspase cascade. Activation of the effector protease caspase-3 is one of the most common events of the apoptotic signaling pathway. Bovine adrenal cortex endothelial (BACE) cells were treated with increasing concentrations of the tested proteins. *E. coli*-produced 16K hPRL was used as a control. 18 h after treatment, cells were lyzed and caspase 3 activity was measured (Caspace assay system, Promega). The results presented in FIG. 4 reveal that MBP-PO-PRL induces caspase 3 activity in a dose-dependent manner, while MBP-POmut-PRL and MBP, were completely inactive. At 40 nM concentration, the MBP-PO-PRL displayed an activity comparable to 10 nM *E. coli*-produced 16K hPRL. These results clearly show that the tilted peptide from 16K hPRL, fused to MBP, is able to specifically induce caspase 3 activation in endothelial cells. Mutations affecting the distribution of the hydrophobic residues abolished this activity.

3.6.3. MBP-PO-PRL Inhibits Proliferation of Endothelial Cells

The ability of MBP-PO-PRL to inhibit ABAE (adult bovine aortic endothelial cell) cells proliferation was examined in vitro. Synchronized ABAE cells were plated with or without 10% FBS medium and treated for 18 h with increasing concentrations of 16K hPRL or MBP-PO-PRL. For the last three hours, the cells were incubated with 500,000 cpm of [$^3$H] thymidine, washed in 5% trichloroacetic acid, solubilized in NaOH, and counted. Results were expressed in cpm and each bar represents the mean±SD, n=3. Proliferation was induced by treating the cells with bFGF 50 pM and 1% FCS. *E. coli*-produced 16K hPRL was used as a control.

Figure 5:
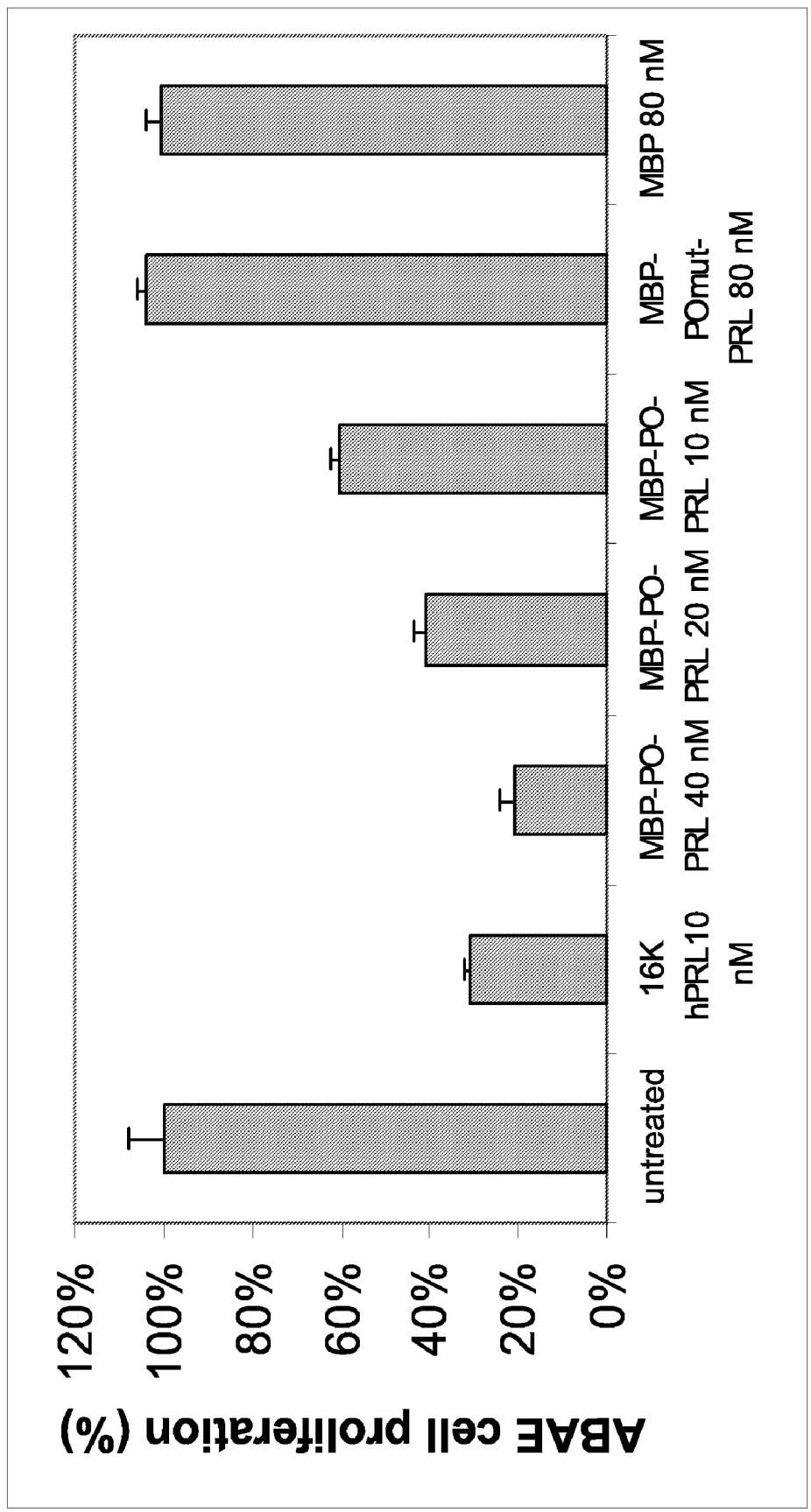
FIG. 5 shows the inhibition of ABAE cell proliferation by the MBP-PO-PRL according to example 3.6.3.

As shown in FIG. 5, MBP-PO-PRL has a dose-dependent inhibitory effect on ABAE cell proliferation. At 40 nM concentration, the MBP-PO-PRL displayed an activity comparable to 10 nM *E. coli*-produced 16K hPRL. MBP or MBP-POmut-PRL treated cell values are not significantly different from untreated cell values. These results clearly show that the tilted peptide from 16K hPRL, fused to MBP, is able to specifically inhibit endothelial cell proliferation. Mutations affecting the distribution of the hydrophobic residues abolished this activity.

3.6.4. MBP-PO-PRL Prevents in vitro Capillary Formation

In order to further analyze the ability of the MBP-PO-PRL to prevent angiogenesis in vitro, its capacity to prevent capillary formation was analyzed in a collagen gel assay. This assay was performed as follows: 20000 cells were plated between two collagen gels (5 volumes rat tail collagen, 1 volume 10×M199 medium, 50 mM NaHCO$_3$). Gels were overlaid with 10% FBS medium containing or not recombinant proteins of interest. As shown in FIG. 9, when included into collagen gels, BACE cells form capillary-like structure (panel A) while addition of 10 nM 16K hPRL prevents capillary formation (panel B). 40 nM MBP-PO-PRL (panel C) is able to inhibit the ability of BACE cells to form capillary structure while 80 nM MBP-POmut-PRL (panel D) has no effect.

3.6.5. MBP-PO-PRL Prevents in vivo Capillary Formation

The antiangiogenic activity of the MBP-PO-PRL was examined in vivo in an early-stage chick chorioallantoic membrane (CAM) assay. The chick CAM assay is a widely and relatively rapid method used to study angiogenesis in vivo. On the 3$^{rd}$ day of development, fertilized chicken embryos were removed from their shell, placed in Petri dishes and incubated at 37° C. On the 7$^{th}$ day, disks (5 mm) of methylcellulose (0.5%, Sigma) containing 40 µg of recombinant proteins and 4 µg of BSA were laid on the chicken CAM. 48 h later, white india ink was injected into the chorioallantoic sac and avascular area was determined. Quantification was performed by measuring the avascular area on at least 7 eggs. As shown in FIG. 10, an avascular area is present in the area surrounding the methylcellulose disk containing 40 µg of MBP-PO-PRL whereas the control MBP-POmut-PRL has no significant effect. Theses results show that MBP-PO-PRL is able to prevent angiogenesis in vivo.

Example 4

Determination of the Antiangiogenic Activity of the Tilted Peptide of 16K hGH Fused to the MBP Protein

4.1. Production of MBO-PO-GH and MBP-POmut-GH Recombinant Fusion Proteins

Using the same procedure as described above, the present inventors produced a fusion protein made of MBP and the tilted peptide of 16K hGH. As a control, mutations that modify the hydrophobic distribution were introduced in the tilted peptide of the 16K hGH. Protein name and peptides sequences are shown in table 4. The inventors evaluated the ability of the MBP-PO-GH, MBP-POmut-GH to induce apoptosis and to inhibits proliferation of endothelial cells as described above. The results clearly show that the tilted peptide from 16K hGH, fused to MBP, is able to specifically induces apoptosis in endothelial cells. Mutations affecting the distribution of the hydrophobic residues abolished this activity.

TABLE 4

Sequences of the tilted peptide of 16K hGH fused to the MBP protein. In italics mutated peptide that have been designed to modify the hydrophobic distribution is shown.

| Protein name | Fusion protein name | Tilted peptide sequence |
|---|---|---|
| 16K hGH | MBP-PO-GH | LLRISLLLIQSWLE (SEQ ID NO: 1) |
| 16K hGH | MBP-PO-GHmut | *LSQILSSLIQSWLE* (SEQ ID NO: 11) |

Figure 6:
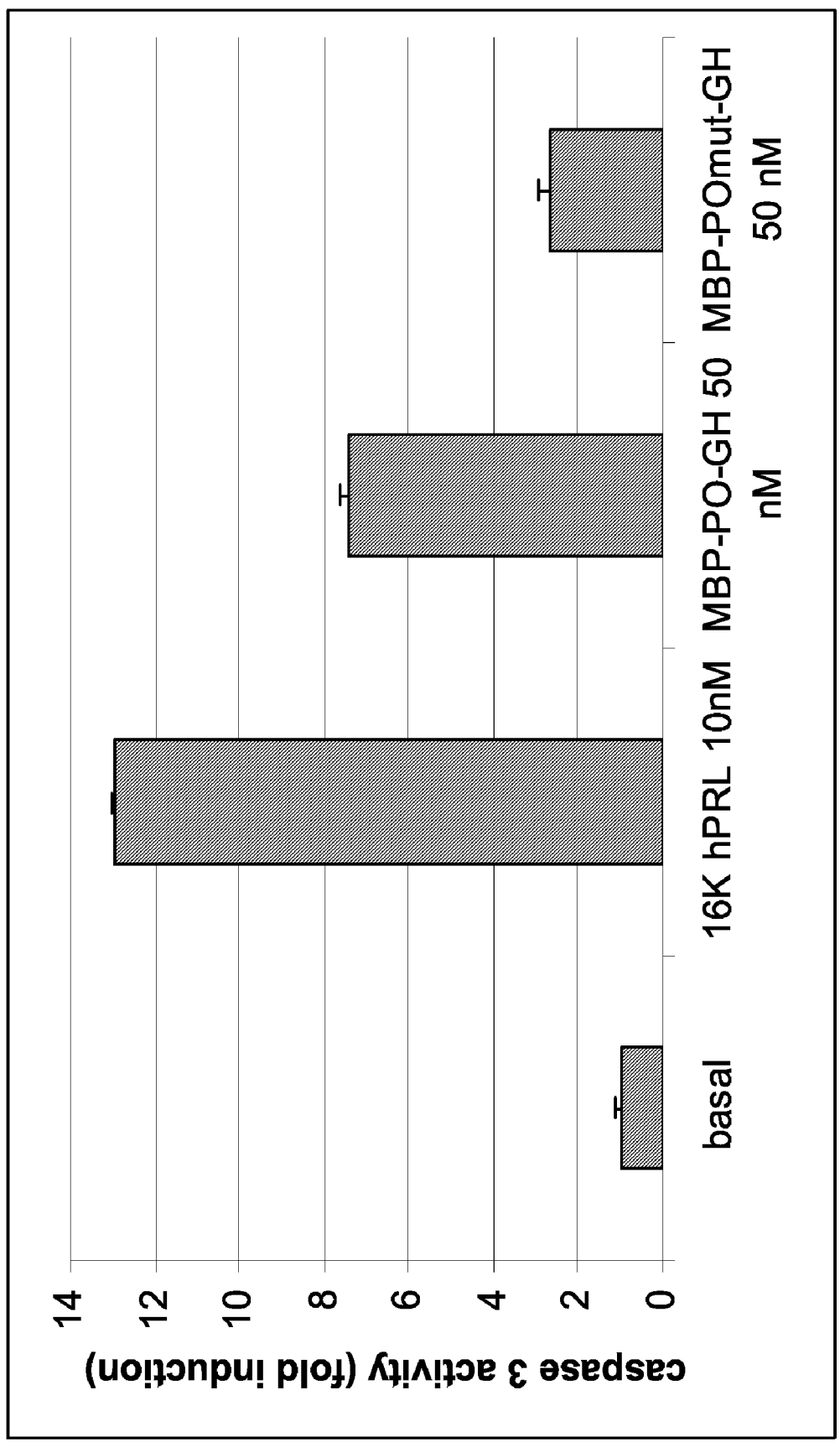
FIG. 6 shows that MBP-PO-GH induces caspase 3 activation in BACE cells according to example 4.2.1.

4.2. Biological Activity of the MBP-PO-GH, MBP-POmut-GH and MBP Proteins 4.2.1. MBP-PO-GH Induces Caspase 3 Activation in Endothelial Cells In order to test the ability of MBP-PO-GH to induce apoptosis in BACE cells, the inventors studied activation of the caspase cascade. BACE cells were treated with increasing concentrations of the tested proteins. *E. coli*-produced 16K hPRL was used as a control. 18 h after treatment, cells were lyzed and caspase 3 activity was measured (Caspace assay system, Promega). The results presented in FIG. 6 reveal that MBP-PO-GH induces caspase 3 activity, while MBP-POmut-GH and MBP, were completely inactive. These results clearly show that the tilted peptide from 16K hGH, fused to MBP, is able to specifically induce caspase 3 activation in endothelial cells. Mutations affecting the distribution of the hydrophobic residues abolished this activity.

4.2.2. MBP-PO-GH Inhibits Proliferation of Endothelial Cells

The ability of MBP-PO-GH to inhibit ABAE cells proliferation was examined in vitro. Synchronized ABAE cells were plated with or without 10% FBS medium and treated for 18 h with increasing concentrations of 16K hPRL or MBP-PO-GH. For the last three hours, the cells were incubated with 500,000 cpm of [$^3$H] thymidine, washed in 5% trichloroacetic acid, solubilized in NaOH, and counted. Results were expressed in cpm and each bar represents the mean±SD, n=3. Proliferation was induced by treating the cells with bFGF 50 pM and 1% FCS. *E. coli*-produced 16K hPRL was used as a control.

Figure 7:
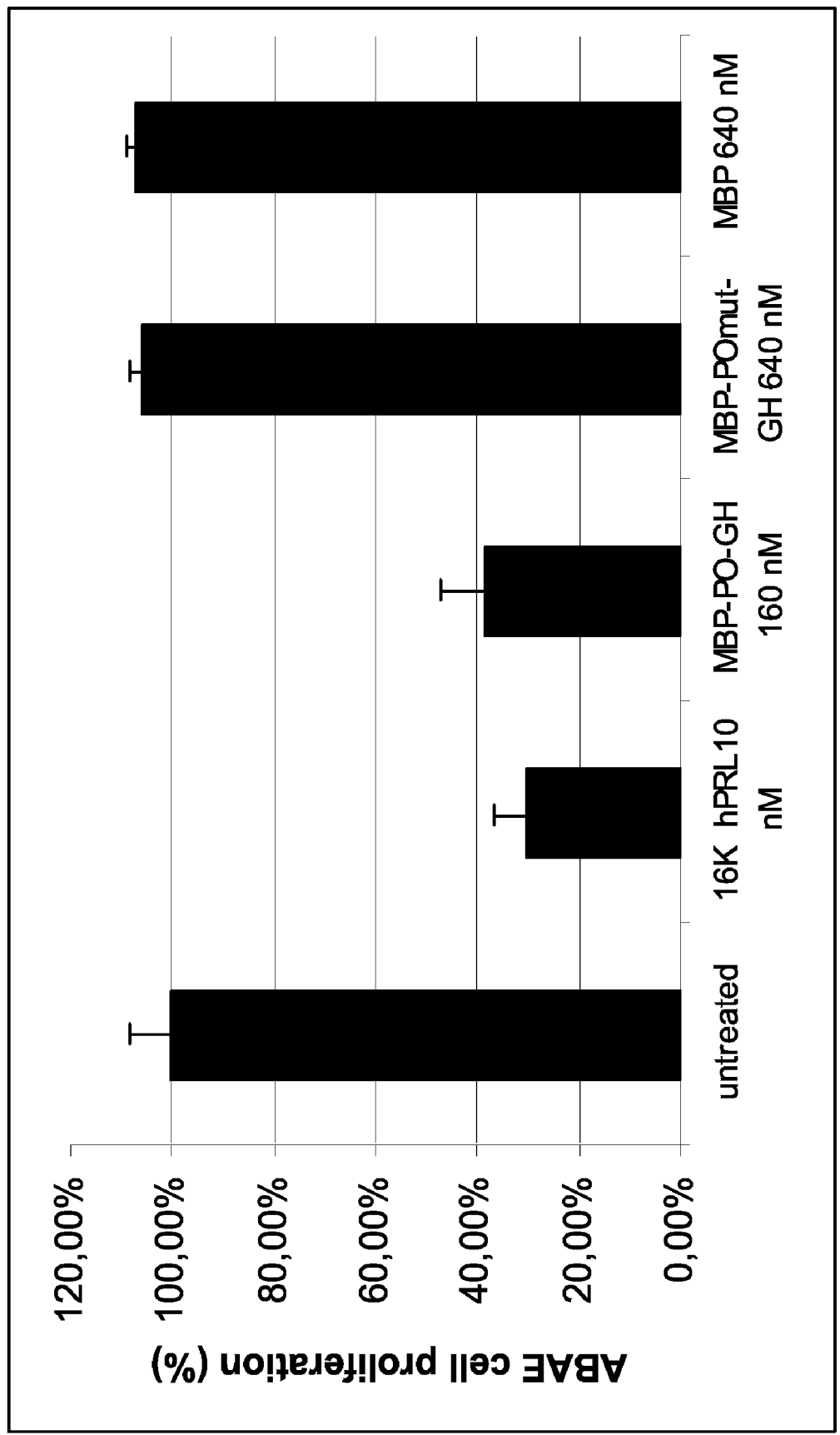
FIG. 7 shows the inhibition of ABAE cell proliferation by the MBP-PO-GH according to example 4.2.2.

As shown in FIG. 7, MBP-PO-GH inhibits ABAE cell proliferation. MBP or MBP-POmut-GH treated cell values are not significantly different from untreated cell values. These results clearly show that the tilted peptide from 16K hGH, fused to MBP, is able to specifically inhibit endothelial cell proliferation. Mutations affecting the distribution of the hydrophobic residues abolished this activity.

4.2.3. MBP-PO-GH Prevents in vitro Capillary Formation

In order to further analyze the ability of the MBP-PO-GH to prevent angiogenesis in vitro, their capacity to prevent capillary formation was analyzed in a collagen gel assay as described above. As shown in FIG. 11, when included into collagen cells, BACE cells form capillary-like structure (panel A) while addition of 10 nM 16K hPRL prevents capillary formation (panel B). 160 nM MBP-PO-GH is able to inhibit the ability of BACE cells to form capillary structure (panel C) while 320 nM MBP-POmut-GH has no effect (panel D).

4.2.4. MBP-PO-PRL and MBP-PO-GH Prevent in vivo Capillary Formation

The antiangiogenic activity of the MBP-PO-GH was examined in vivo in the CAM assay as described above. As shown in FIG. 12, an avascular area is present in the area surrounding the methylcellulose disk containing 40 μg of MBP-PO-GH whereas the control MBP-POmut-GH has no significant effect. Theses results show that MBP-PO-GH is able to prevent angiogenesis in vivo.

Example 5

Determination of the Antiangiogenic Activity of the Tilted Peptide of 16K hPL Fused to the MBP Protein Using the same procedure as described above, a fusion protein made of MBP and the tilted peptide of 16K hPL was produced. As a control, mutations that modify the hydrophobic distribution were introduced in the tilted peptide of the 16K hPL. Protein name and peptides sequences are shown in table 5. The ability of the MBP-PO-PL, MBP-POmut-PL to induce apoptosis in endothelial cells was evaluated as described above. The results clearly show that the tilted peptide from 16K hPL, fused to MBP, is able to specifically induces apoptosis in endothelial cells. Mutations affecting the distribution of the hydrophobic residues abolished this activity.

TABLE 5

Sequences of the tilted peptide of 16K hPL fused to the MBP protein. In italics mutated peptide that have been designed to modify the hydrophobic distribution is shown.

| Protein name | Fusion protein name | Tilted peptide sequence |
|---|---|---|
| 16K hPL | MBP-PO-PL | LLRISLLLIESWLE SEQ ID NO: 2 |
| 16K hPL | MBP-PO-PLmut | LSQILSSLIESWLE SEQ ID NO: 12 |

Example 6

Expression and Biological Activity of Fusion Proteins Between MBP and Known Tilted Peptides 6.1. Production of MBO-PO-SIV and MBP-PO-BA Recombinant Fusion Proteins The inventors also produced fusion proteins between MBP and two well-known tilted peptides of proteins whose function is not related to angiogenesis i.e. the β-amyloid protein (Pillot, T., et al. J Biol Chem 271:28757-65 (1996)) and the fusion protein of simian immunodeficiency virus (SIV) virus (Horth, M., et al. Embo J 10:2747-55 (1991)). The same strategy as described above was used to generate fusion proteins made of MBP and the tilted peptides. Protein name and peptides sequences are shown in table 7. Fusion proteins were expressed and purified as described above. The ability of these peptides to induce apoptosis in endothelial cells was evaluated as described above. The results clearly show that the tilted peptides, from the β-amyloid protein amyloid and fusion protein of SIV fused to MBP, are able to specifically induce apoptosis and inhibit proliferation of endothelial cells. Mutations affecting the distribution of the hydrophobic residues abolished this activity.

TABLE 7

Sequences of the β-amyloid and SIV tilted peptide fused to the MBP protein.

| Protein name | Fusion protein name | Tilted peptide sequence |
| --- | --- | --- |
| β-amyloid | MBP-PO-BA | GAIIGLMVGGVVIA (SEQ ID NO: 6) |
| SIV fusion protein | MBP-PO-SIV | GVFVLGFLGFLA (SEQ ID NO: 7) |

6.2. Biological Activity of the MBP-PO-SIV and MBP-PO-BA Recombinant Proteins

Figure 8:
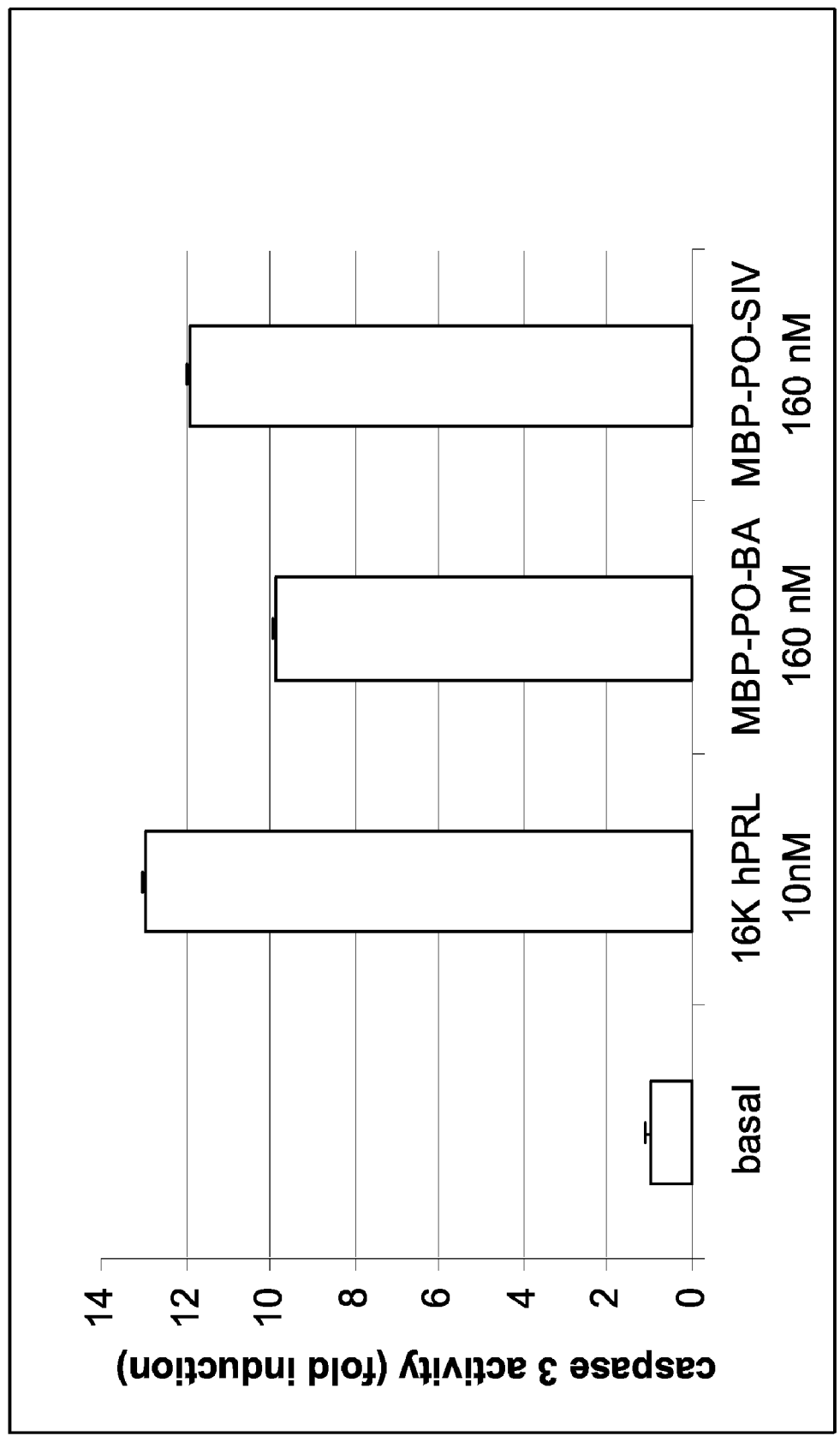
FIG. 8 shows the MBP-PO-SIV and MBP-PO-BA induce caspase 3 activation in BACE cells according to example 6.2.1.

6.2.1. MBP-PO-SIV and MBP-PO-BA Induce Caspase 3 Activation in Endothelial Cells In order to test the ability of MBP-PO-SIV and MBP-PO-BA to induce apoptosis in BACE cells, the inventors studied activation of the caspase cascade. BACE cells were treated with increasing concentrations of the tested proteins. *E. coli*-produced 16K hPRL was used as a control. 18 h after treatment, cells were lyzed and caspase 3 activity was measured (Caspace assay system, Promega). The results presented in FIG. 8 reveal that MBP-PO-SIV and MBP-PO-BA induces caspase 3 activity. These results clearly show that the tilted peptide from fusion protein of simian immunodeficiency virus and the tilted peptide from the β-amyloid protein, fused to MBP, are able to specifically induce caspase 3 activation in endothelial cells.

6.2.2. MBP-PO-SIV and MBP-PO-BA Inhibit Endothelials Cell Proliferation

Figure 13:
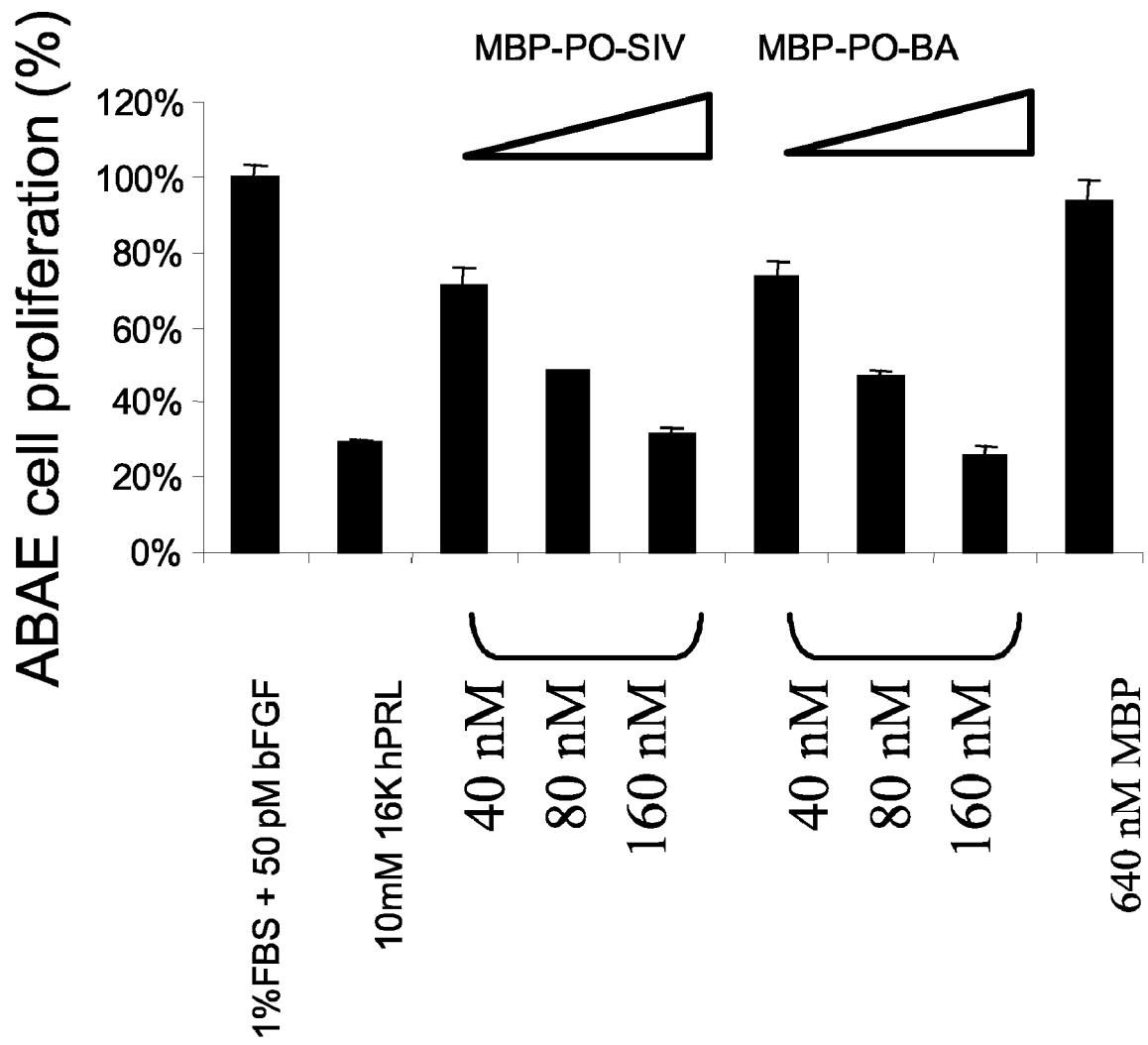
FIG. 13 shows the inhibition of endothelial cell proliferation by MBP-PO-SIV and MBP-PO-BA according to example 6.2.2.

The ability of MBP-PO-SIV and MBP-PO-BA to inhibit ABAE cell proliferation was examined as described above. The results presented in FIG. 13 show that, MBP-PO-SIV and MBP-PO-BA exert a dose-dependent inhibitory effect on ABAE cell proliferation. At 160 nM concentration, the MBP-PO-SIV and MBP-PO-BA displays an activity comparable to 10 nM *E. coli*-produced 16K hPRL. These results clearly show that the tilted peptide from the fusion protein of simian immunodeficiency virus and the tilted peptide from the β-amyloid B protein fused to MBP, are able to inhibit endothelial cell proliferation.

6.2.3. MBP-PO-SIV and MBP-PO-BA Prevent in vitro Capillary Formation

The ability of MBP-PO-SIV and MBP-PO-BA to inhibit BACE capillary formation in vitro was examined as described above. As shown in FIG. 14, when included into collagen gels, BACE cells form capillary-like structures (panel A), 160 nM MBP-PO-SIV (panel B) and MBP-PO-BA (panel C) are able to prevent capillary structures formation. These results clearly show that the tilted peptide from the fusion protein of simian immunodeficiency virus and the tilted peptide from the β-amyloid B protein fused to MBP, are able to prevent capillary gel formation.

6.2.4. MBP-PO-SIV and MBP-PO-BA Prevent in vivo Capillary Formation

The ability of MBP-PO-SIV and MBP-PO-BA to inhibit capillary formation in vivo was examined as described above. As shown in FIG. 15, an avascular area is present in the area surrounding the methylcellulose disks containing 40 μg of MBP-PO-SIV or MBP-PO-BA. These results clearly show that the tilted peptide from the fusion protein of simian immunodeficiency virus and the tilted peptide from the β-amyloid B protein fused to MBP, are able to prevent capillary formation in vivo.

Example 7

The Ability of MBP-PO-PRL, MBP-PO-GH to Reduce Viability of Endothelial Cells is Specific for Endothelial Cells In order to determine whether the effect of tilted peptides exerted on endothelial cells is cell specific, a viability assay was performed on BACE and ABAE endothelial cells and on two tumoral cells lines, the B16-F10 murine melanoma cells and the MDA-MB-231 human breast cancer cell. Viable cells are detected by the presence of intracellular esterase, determined by the enzymatic conversion of non fluorescent calcein AM (an ester derivative) into fluorescent calcein.

25000 BACE or ABAE cells were plated in 24-well plates in 0.5 ml 10% FCS/DMEM medium and incubated with the recombinant proteins for 24 h. Cells were washed with PBS and incubated with 1 μM calcein-AM for 30 min. Fluorence was then measured with a fluorometer at 535 nm. Viability is expressed as fluorescence arbitrary unit. As shown in FIG. 16, 40 nM MBP-PO-PRL, 320 nM MBP-PO-GH reduced viability of both endothelial cell types while 80 nM MBP-POmut-PRL, 640 nM MBP-POmut-GH or 640 nM MBP have no effect. As positive control, endothelial cells were incubated with 10 nM hPRL 16K.

To determine whether the activity of the MBP-PO-PRL and MBP-PO-GH is specific for endothelial cells, their ability to affect viability of B16-F10 and MDA-MB-231 cell line was determined. 25000 MDA-MB-231 cells and B16-F10 cells were plated in 24-well plates, respectively in 0.5 ml 10% FCS/RPMI medium and in 10% FCS/DMEM 4500 medium. The cells were treated with recombinant proteins or camptothecin for 72 h. Cells were washed, incubated with calcein-AM and fluorescence determined as described above. As shown in FIG. 16, 10 nM 16K hPRL, 40 nM MBP-PO-PRL, 320 nM MBP-PO-GH or 640 nM MBP do not affect viability of B16-F10 or MDA-MB-231 cells whereas campthotecin does. These results show that the capacity of tilted peptides to reduce cell viability is specific for endothelial cells. Similar results were obtained with MBP-PO-SIV and MBP-PO-BA.

Example 8

Mutations that Disrupt the Obliquity of the Tilted Peptide of 16K hPRL Inhibit its Antiangiogenic Activity

8.1. Production of the MBP-16K hPRL and MBP-16K hPRL mut Recombinant Fusion Proteins.

To determine whether the tilted peptide region of the 16K hPRL is responsible of its antiangiogenic activity, mutations were introduced in the 16K hPRL. The tilted peptide sequence FLSLIVSILRSWNE (SEQ ID NO: 3) was replaced by the sequence FNSLISSILRVWLE (SEQ ID NO: 10). The 16K hPRL and the 16K hPRL mutated in its tilted peptide region were produced in fusion with the MBP. The 16K hPRL mutated in its tilted peptide region was called MBP-16 KhPRLmut. As a control, we produced the 16K hPRL fused with the MBP and called it MBP-16 KhPRL.

The 16K hPRL and the mutated 16K hPRL coding sequences were obtained by amplification by PCR. The oligonucleotides used for the PCR were designed in order to include XmnI and BamHI restriction sites respectively upstream and downstream the 16K hPRL or the mutated 16K hPRL coding sequence. One clone of each construct was selected and sequence was verified by sequencing. Recombinant proteins were produced and purified as described above.

8.2. Biological Activity of the MBP-16K hPRL and MBP-16K hPRL mut.

The ability of MBP-16K hPRL and MBP-16K hPRLmut to induce caspase 3 activation was determined as described above. As show in FIG. 17, the activation of the caspase 3 is reduced by 40-50% in a dose dependent manner when ABAE cells are treated with the MBP-16 KhPRLmut by comparison with the MBP-16 KhPRL. These results show that the tilted peptide region is essential for the activity of 16K hPRL.

8.3. Production of the MBP-16K hPRL Mutated in its Second Tilted Peptide Region

Using the same procedure as described above, a second tilted peptide was identified in the hPRL sequence. The sequence of this second tilted peptide is PLYHLVTEVRGM-QEA (SEQ ID NO: 8).

To determine if this second tilted peptide region of the 16K hPRL plays a role in 16K hPRL antiangiogenic activity, mutations were introduced in this region of the 16K hPRL. The tilted peptide sequence PLYHLVTEVRGMQEA (SEQ ID NO: 8) was replaced by the sequence PQHYLETWRG-MLEA (SEQ ID NO: 9). The 16K hPRL mutated in its two tilted peptide regions was produced in fusion with the MBP. This protein is called MBP-16 KhPRLmut PO 1+2.

The MBP-16 KhPRLmut PO 1+2 coding sequences were obtained by amplification by PCR. The oligonucleotides used for the PCR were designed in order to include XmnI and BamHI restriction sites respectively upstream and downstream the mutated 16K hPRL coding sequence. One clone of each construct was selected and sequences were verified by sequencing. Recombinant proteins were produced and purified as described above.

8.4. Biological Activity of the MBP-16K hPRL and MBP-16 KhPRLmut PO 1+2

The ability of MBP-16K hPRL and MBP-16 KhPRLmut PO 1+2 to induce caspase 3 activation was determined as described above. As show in FIG. 17, panel B, the activation of the caspase 3 is abolished when ABAE cells are treated with the MBP-16 KhPRLmut PO 1+2 by comparison with the MBP-16 KhPRL. These results show that both tilted peptide regions are required for the antiangiogenic activity of 16K hPRL.

Example 9

16K hRPL is Trimeric in Native Conditions

The apparent molecular mass (app. M.M.) of 16K hPRL was determined both in native and denaturating conditions. 16K hPRL was produced as described in Tabruyn, S. P., et al. Mol Endocrinol 17:1815-23 (2003). As shown in FIG. 18, under denaturating conditions, the app. M.M. of 16K hPRL deduced from its migration profile on SDS-PAGE is approximately 16000. The addition of a reducing agent (1'-mercaptoethanol) does not modify its migration. In order to determine 16K hPRL app.M.M. in native conditions, a Superose 12 size exclusion chromatography was performed. 16 KhPRL is eluted in a major peak which, according to our column calibration, corresponds to an app. M.M. of 46700. Since the calculated M.M. of this 16K hPRL is 15900, the 16K hPRL eluted in this peak are presumably under a trimeric form. These trimers are not covalently bound since addition of β-ME does not change the migration profile while performing SDS-PAGE. As the use of ionic detergents or denaturating agents such as urea is the only way to separate these multimers, it suggests that they are formed by strong hydrophobic interactions. The results show that 16K hPRL is trimer in native conditions.

The invention claimed is:

1. A composition comprising an isolated antiangiogenic peptide or a fusion protein comprising a heterologous protein fused to the antiangiogenic peptide, wherein the peptide has antiangiogenic activity and consists of the amino acid sequence:

X1-X2-X3-X4-X5-X6-X7-X8-X9-X10-X11-X12-X13-X14, wherein

X1 is any amino acid residue compatible with forming a helix;
X2 is an amino acid residue of: Leu;
X3 is an amino acid residue of: Arg, Ser;
X4 is an amino acid residue of: Ile, Leu;
X5 is any amino acid residue compatible with forming a helix;
X6 is an amino acid residue of: Leu, Val;
X7 is an amino acid residue of: Leu, Ser;
X8 is any amino acid residue compatible with forming a helix;
X9 is any amino acid residue compatible with forming a helix;
X10 is an amino acid residue of: Gln, Glu, Arg;
X11 is an amino acid residue of: Ser;
X12 is an amino acid residue of: Trp;
X13 is an amino acid residue of: Leu, Asn;
X14 is an amino acid residue of: Glu.

2. The composition according to claim 1, wherein
X1 is an amino acid residue of: Leu, Phe;
X2 is an amino acid residue of: Leu;
X3 is an amino acid residue of: Arg, Ser;
X4 is an amino acid residue of: lie, Leu;
X5 is an amino acid residue of: Ser, Ile;
X6 is an amino acid residue of: Leu, Val;
X7 is an amino acid residue of: Leu, Ser,
X8 is an amino acid residue of: Leu, lie;
X9 is an amino acid residue of: lie, Leu;
X10 is an amino acid residue of: Gin, Giu, Arg;
X11 is an amino acid residue of: Ser;
X12 is an amino acid residue of: Trp;
X13 is an amino acid residue of: Leu, Asn;
X14 is an amino acid residue of: Glu.

3. The composition according to claim 1, wherein the amino acid sequence X1-X14 of the peptide is SEQ ID NO: 3.

4. The composition according to claim 1, wherein the amino acid sequence X1-X14 of the peptide is a tilted peptide.

5. The composition according to claim 1, wherein the amino acid sequence X1-X14 of the peptide is a tilted peptide and wherein the calculated mean hydrophobicity of the tilted peptide is higher than 0.1 and the tilted peptide is defined by the characteristics that if the three-dimensional structure of the peptide is arranged as an alpha-helix, the calculated hydrophobic isopotential of the peptide is asymmetric and the calculated minimal energy conformation is oriented at a hydrophobic/hydrophilic interface and the calculated angle between the helix axis and the interface plane between hydrophobic and hydrophilic phases is between 30° and 70°.

6. The composition according to claim 1, wherein the amino acid sequence X1-X14 of the peptide is a tilted peptide and wherein the calculated mean hydrophobicity of the tilted peptide is higher than 0.2.

7. The composition according claim 1, wherein the amino acid sequence X1-X14 of the peptide is a tilted peptide and wherein the calculated angle between the helix axis of the tilted peptide and the interface plane between hydrophobic and hydrophilic phases is between 35° and 65°.

8. The composition according to claim 1, wherein the heterologous protein is maltose binding protein.

9. The composition of claim 1 wherein the peptide consists of SEQ ID NO: 3.

10. The composition according to claim 1, wherein the peptide is a tilted peptide.

11. The composition according to claim 1, wherein the amino acid sequence X1-X14, the antiangiogenic peptide, or the fusion protein forms a trimeric structure.

12. A method of inhibiting angiogenesis comprising administering an effective dose the composition according to claim 1 to a subject in need thereof.

* * * * *

UNITED STATES PATENT AND TRADEMARK OFFICE
CERTIFICATE OF CORRECTION

PATENT NO. : 7,655,626 B2
APPLICATION NO. : 11/573660
DATED : February 2, 2010
INVENTOR(S) : Martial et al.

It is certified that error appears in the above-identified patent and that said Letters Patent is hereby corrected as shown below:

On the Title Page (Item 56), line 18, please delete "Inhibit" and insert therefore, --inhibit--.

At Figure 3 of the drawings, below panel C, in the label for the x-axis, please delete "MBP-po PRL" and insert therefore, --MBP-PO-PRL--.

At Figure 3 of the drawings, below panel E in the label for the x-axis, please delete "MBP-pomut PRL" and insert therefore, --MBP-POmut-PRL--.

At Figure 16 of the drawings, below panel A in the y-axis, please delete "Fluoresence" and insert therefore, --Fluorescence--.

At Figure 16 of the drawings, below panel B in the y-axis, please delete "Fluoresence" and insert therefore, --Fluorescence--.

At Figure 16 of the drawings, below panel C in the y-axis, please delete "Fluoresence" and insert therefore, --Fluorescence--.

At Figure 16 of the drawings, below panel D in the y-axis, please delete "Fluoresence" and insert therefore, --Fluorescence--.

At column 2, lines 32-33, please delete "Opthalmol" and insert therefore, --Ophthalmol--.

At column 6, line 33, please delete "(hPRL)" and insert therefore, --(hPRL);--.

At column 9, line 48, please delete "hGH-v)" and insert therefore, --hGH-v);--.

Signed and Sealed this

Third Day of August, 2010

David J. Kappos
*Director of the United States Patent and Trademark Office*

CERTIFICATE OF CORRECTION (continued)
U.S. Pat. No. 7,655,626 B2

At column 11, line 10 (approx), please delete "fusiogenic" and insert therefore, --fusogenic--.

At column 12, lines 29-36 (approx), please delete:

"FIG. 1 shows in A. a protein sequence of hPRL (SEQ ID NO: 14). The hPRL protein contains two tilted peptides: the region which is likely to adopt a tilted peptide structure is highlighted in bold (1$^{st}$ tilted peptide SEQ ID NO: 3) and in italics (2$^{nd}$ tilted peptide SEQ ID NO: 8). Alpha-helical regions are indicated by underlining (Keeler, C., et al. J Mol Biol 328:1105-21(2003)). B. Alignment of the tilted peptide regions in the 16K fragments of the PRL/GH family."

and insert therefore,

--FIGS. 1(A-B): Panel (A) shows a protein sequence of hPRL (SEQ ID NO: 14). The hPRL protein contains two tilted peptides: the region which is likely to adopt a tilted peptide structure is highlighted in bold (1st tilted peptide SEQ ID NO: 3) and in italics (2nd tilted peptide SEQ ID NO: 8). Alpha-helical regions are indicated by underlining (Keeler, C., et al. J Mol Biol 328:1105-21 (2003)). Panel (B) is an alignment of the tilted peptide regions in the 16K fragments of the PRL/GH family.--.

At column 12, lines 47-51 (approx), please delete:

"FIG. 3 shows the analysis of the induction of apoptosis by flow cytometry according to example 3.6.1. BACE cells were left untreated (A), or treated with 10 nM E. coli-produced 16K hPRL (B), 40 nM MBP-PO-PRL (C), 80 nM MBP (D) or 80 nM MBP-POmut-PRL(E)."

and insert therefore,

--FIGS. 3(A-F) shows the analysis of the induction of apoptosis by flow cytometry according to example 3.6.1. BACE cells were left untreated, Panel (A): or treated with 10 nM E. coli-produced 16K hPRL, Panel (B): 40 nM MBP-PO-PRL, Panel (C): 80 nM MBP, Panel (D): or 80 nM MBP-POmut-PRL, (E). The percentage of sub G1 cell population for each of (A)-(E) is summarized in Panel (F).--.

At column 12, lines 66-67 through column 13, lines 1-14, please delete:

"FIG. 9 shows that MBP-PO-PRL inhibits capillary formation in vitro in the collagen gel assay according to example 3.6.4. Panel A: untreated cells, panel B: 10 nM 16K hPRL, panel C: 40 nM MBP-PO-PRL, panel D: 80 nM MBP-POmut-PRL.

FIG. 10 shows that MBP-PO-PRL inhibits capillary formation in vivo in the chick chorioallantoic membrane assay according to example 3.6.5.

FIG. 11 shows that MBP-PO-GH inhibits capillary formation in vitro in the collagen gel assay according to example 4.2.3. Panel A: untreated cells, panel B: 10 nM 16K hPRL, panel C: 80 nM MBP-PO-GH, panel D: 160 nM MBP-POmut-GH.

FIG. 12 shows that MBP-PO-GH inhibits capillary formation in vivo in the chick chorioallantoic membrane assay according to example 4.2.4."

and insert therefore,

--FIGS. 9(A-D) shows that MBP-PO-PRL inhibits capillary formation in vitro in the collagen gel assay according to example 3.6.4. Panel A: untreated cells, panel B: 10 nM 16K hPRL, panel C: 40 nM MBP-PO-PRL, panel D: 80 nM MBP-POmut-PRL.

FIGS. 10(A-B) shows that MBP-PO-PRL inhibits capillary formation in vivo in the chick chorioallantoic membrane assay according to example 3.6.5. Panel A: chick chorioallantoic membrane images; Panel B: graphical summary of avascular areas.

FIGS. 11(A-D) shows that MBP-PO-GH inhibits capillary formation in vitro in the collagen gel assay according to example 4.2.3. Panel A: untreated cells, panel B: 10 nM 16K hPRL, panel C: 80 nM MBP-PO-GH, panel D: 160 nM MBP-POmut-GH.

FIGS. 12(A-B) shows that MBP-PO-GH inhibits capillary formation in vivo in the chick chorioallantoic membrane assay according to example 4.2.4. Panel A: chick chorioallantoic membrane images; Panel B: graphical summary of avascular areas.--.

At column 13, lines 18-48, please delete:

"FIG. 14 shows that MBP-PO-SIV and MBP-PO-BA inhibit capillary formation in vitro in the collagen gel assay according to example 6.2.3. Panel A: untreated cells, panel B: 160 nM MBP-PO-SIV, panel C: 160 nM MBP-PO-BA.

FIG. 15 shows that MBP-PO-SIV and MBP-PO-BA inhibit capillary formation in vivo in the chick chorioallantoic membrane assay according to example 6.2.4.

FIG. 16 shows that MBP-PO-PRL and MBP-PO-GH reduce viability of endothelial cells (BACE and ABAE cells) but not of tumoral (B16-F10 and MDA-MB-231) cells according to example 7.

FIG. 17 shows that 16K hPRL fused to MBP and mutated in its tilted peptide region (MBP-16K hPRLmut) (panel A) is less able to induce caspase 3 activation in endothelial cells than unmutated 16K hPRL fused to MBP (MBP-16K hPRL) according to example 8. Mutation of both tilted peptides of 16 K hPRL completely abolishes 16 K hPRL activity (panel B) (Example 8.3 and 8.4).

FIG. 18 shows that 16K hPRL is monomeric in denaturating condition but trimeric in native conditions according to example 9. Panel A: 17% polyacrylamide SDS-PAGE of 16K hPRL. Lane 1-3: SDS-PAGE in the presence of β-ME. Lane 1: purified 16K hPRL. Lane 2: molecular weight marker. Lane 3: protein unrelated to this topics. Lanes 4: SDS-PAGE in the absence of β-ME: purified 16K hPRL. To the right, molecular weight of the marker are shown (in kDa). Panel B: Analytical size exclusion chromatography of 16K hPRL on a Superose 12 molecular sieve A: Calibration of the column with Dextran blue (peak 1), dimeric (peak 2) and monomeric BSA (peak 3), ovalbumin (peak 4) and

CERTIFICATE OF CORRECTION (continued)
U.S. Pat. No. 7,655,626 B2 myoglobin (peak 5); B: 16K hPRL"

and insert therefore,

--FIGS. 14(A-C) shows that MBP-PO-SIV and MBP-PO-BA inhibit capillary formation in vitro in the collagen gel assay according to example 6.2.3. Panel A: untreated cells, panel B: 160 nM MBP-PO-SIV, panel C: 160 nM MBP-PO-BA.

FIGS. 15(A-B) shows that MBP-PO-SIV and MBP-PO-BA inhibit capillary formation in vivo in the chick chorioallantoic membrane assay according to example 6.2.4. Panel A: chick chorioallantoic membrane images; Panel B: graphical summary of avascular areas. FIGS. 16(A-D) shows that MBP-PO-PRL and MBP-PO-GH reduce viability of endothelial cells (BACE and ABAE cells) but not of tumoral (B16-F10 and MDA-MB-231) cells according to example 7. Panel A: BACE; Panel B: ABAE; Panel C: B16-F10; Panel D: MDA-MB231.

FIGS. 17(A-B) shows that 16K hPRL fused to MBP and mutated in its tilted peptide region (MBP-16K hPRLmut) (panel A) is less able to induce caspase 3 activation in endothelial cells than unmutated 16K hPRL fused to MBP (MBP-16K hPRL) according to example 8. Mutation of both tilted peptides of 16K hPRL completely abolishes 16K hPRL activity (panel B) (Example 8.3 and 8.4).

FIGS. 18(A-B) shows that 16K hPRL is monomeric in denaturating condition but trimeric in native conditions according to example 9. Panel A: 17% polyacrylamide SDS-PAGE of 16K hPRL. Lane 1-3: SDS-PAGE in the presence of β-ME. Lane 1: purified 16K hPRL. Lane 2: molecular weight marker. Lane 3: protein unrelated to this topics. Lanes 4: SDS-PAGE in the absence of β-ME: purified 16K hPRL. To the right, molecular weight of the marker are shown (in kDa). Panel B: Analytical size exclusion chromatography of 16K hPRL on a Superose 12 molecular sieve A: Calibration of the column with Dextran blue (peak 1), dimeric (peak 2) and monomeric BSA (peak 3), ovalbumin (peak 4) and myoglobin (peak 5); B: 16K hPRL.--.

At column 19, line 19, please delete "Amphotrophic" and insert therefore, --Amphotropic--.

At column 19, line 31 (approx), please delete "endosmolytic" and insert therefore, --endosomolytic--.

At column 19, line 45 (approx), please delete "asialo-oromucoid," and insert therefore, --asialoorosomucoid,--.

At column 23, lines 39-67 (approx) through column 24, lines 1-50, below "inhibition of any of the diseases the patient is afflicted with." please delete:

"FIGS. 1(A-B): Panel (A) shows a protein sequence of hPRL (SEQ ID NO: 14). The hPRL protein contains two tilted peptides: the region which is likely to adopt a tilted peptide structure is highlighted in bold ($1^{st}$ tilted peptide SEQ ID NO: 3) and in italics ($2^{nd}$ tilted peptide SEQ ID NO: 8). Alpha-helical regions are indicated by underlining (Keeler, C., et al. J Mol Biol 328:1105-21 (2003)). Panel (B) is an alignment of the tilted peptide regions in the 16K fragments of the PRL/GH family.

FIGS. 3(A-F) shows the analysis of the induction of apoptosis by flow cytometry according to example 3.6.1. BACE cells were left untreated, Panel (A): or treated with 10 nM E. coli-produced 16K hPRL, Panel (B): 40 nM MBP-PO-PRL, Panel (C): 80 nM MBP, Panel (D): or 80 nM MBP-POmut-PRL, (E). The percentage of sub G1 cell population for each of (A)-(E) is summarized in Panel (F).

FIGS. 9(A-D) shows that MBP-PO-PRL inhibits capillary formation in vitro in the collagen gel assay according to example 3.6.4. Panel A: untreated cells, panel B: 10 nM 16K hPRL, panel C: 40 nM MBP-PO-PRL, panel D: 80 nM MBP-POmut-PRL.

FIGS. 10(A-B) shows that MBP-PO-PRL inhibits capillary formation in vivo in the chick chorioallantoic membrane assay according to example 3.6.5. Panel A: chick chorioallantoic membrane images; Panel B: graphical summary of avascular areas.

FIGS. 11(A-D) shows that MBP-PO-GH inhibits capillary formation in vitro in the collagen gel assay according to example 4.2.3. Panel A: untreated cells, panel B: 10 nM 16K hPRL, panel C: 80 nM MBP-PO-GH, panel D: 160 nM MBP-POmut-GH.

FIGS. 12(A-B) shows that MBP-PO-GH inhibits capillary formation in vivo in the chick chorioallantoic membrane assay according to example 4.2.4. Panel A: chick chorioallantoic membrane images; Panel B: graphical summary of avascular areas.

FIGS. 14(A-C) shows that MBP-PO-SIV and MBP-PO-BA inhibit capillary formation in vitro in the collagen gel assay according to example 6.2.3. Panel A: untreated cells, panel B: 160 nM MBP-PO-SIV, panel C: 160 nM MBP-PO-BA.

FIGS. 15(A-B) shows that MBP-PO-SIV and MBP-PO-BA inhibit capillary formation in vivo in the chick chorioallantoic membrane assay according to example 6.2.4. Panel A: chick chorioallantoic membrane images; Panel B: graphical summary of avascular areas.

FIGS. 16(A-D) shows that MBP-PO-PRL and MBP-PO-GH reduce viability of endothelial cells (BACE and ABAE cells) but not of tumoral (B16-F10 and MDA-MB-231) cells according to example 7. Panel A: BACE; Panel B. ABAE; Panel C. B16-F10; Panel D: MDA-MB231.

FIGS. 17(A-B) shows that 16K hPRL fused to MBP and mutated in its tilted peptide region (MBP-16K hPRLmut) (panel A) is less able to induce caspase 3 activation in endothelial cells than unmutated 16K hPRL fused to MBP (MBP-16K hPRL) according to example 8. Mutation of both tilted peptides of 16 K hPRL completely abolishes 16 K hPRL activity (panel B) (Example 8.3 and 8.4).

FIGS. 18(A-B) shows that 16K hPRL is monomeric in denaturating condition but trimeric in native conditions according to example 9. Panel A: 17% polyacrylamide SDS-PAGE of 16K hPRL. Lane 1-3: SDS-PAGE in the presence of β-ME. Lane 1: purified 16K hPRL. Lane 2: molecular weight marker. Lane 3: protein unrelated to this topics. Lanes 4: SDS-PAGE in the absence of β-ME: purified 16K hPRL. To the right, molecular weight of the marker are shown (in kDa). Panel B: Analytical size exclusion chromatography of 16K hPRL on a Superose 12 molecular sieve A: Calibration of the column with Dextran blue (peak 1), dimeric (peak 2) and monomeric BSA (peak 3), ovalbumin (peak 4) and myoglobin (peak 5); B: 16K hPRL.".

At column 26, line 13 (approx), please delete "Barlett's" and insert therefore, --Bartlett's--.

At column 26, line 34 (approx), please delete "Acid)" and insert therefore, --Acid).--.

At column 28, line 15 (approx), please delete "PO mut-PRL" and insert therefore, --POmut-PRL--.

At column 28, line 18, please delete "PO mut-PRL" and insert therefore, --POmut-PRL--.

At column 28, line 67, please delete "loaded" and insert therefore, --loaded.--.

At column 29, line 20, please delete "Dulbbecco's" and insert therefore, --Dulbecco's.--.

At column 29, line 31, please delete "asynchonized" and insert therefore, --asynchronized.--.

At column 34, line 22, please delete "Fluorence" and insert therefore, --Fluorescence.--.

At column 34, lines 36-37, please delete "campthotecin" and insert therefore, --camptothecin--.

At column 34, line 41, please delete "campthotecin" and insert therefore, --camptothecin--.

At column 35, lines 24-25 (approx), please delete "PQHYLETWRGMLEA" and insert therefore, --PQHYLETVVRGMLEA--.

CERTIFICATE OF CORRECTION (continued)
U.S. Pat. No. 7,655,626 B2

At column 36, line 22 (approx), please delete "(1" and insert therefore, --(β--.

In Claim 2 at column 57, line 46, please delete "lie," and insert therefore, --Ile,--.

In Claim 2 at column 57, line 49, please delete "Ser," and insert therefore, --Ser;--.

In Claim 2 at column 57, line 50, please delete "lie;" and insert therefore, --Ile;--.

In Claim 2 at column 57, line 51, please delete "lie," and insert therefore, --Ile,--.

In Claim 2 at column 57, line 52, please delete "Gin, Giu," and insert therefore, --Gln, Glu,--.

In Claim 12 at column 58, line 52, after "dose" please add --of--.

SEQUENCE LISTING

<160> NUMBER OF SEQ ID NOS: 49

<210> SEQ ID NO 1
<211> LENGTH: 14
<212> TYPE: PRT
<213> ORGANISM: Artificial sequence
<220> FEATURE:
<223> OTHER INFORMATION: synthetic peptide

<400> SEQUENCE: 1

Leu Leu Arg Ile Ser Leu Leu Leu Ile Gln Ser Trp Leu Glu
1               5                   10

<210> SEQ ID NO 2
<211> LENGTH: 14
<212> TYPE: PRT
<213> ORGANISM: Artificial sequence
<220> FEATURE:
<223> OTHER INFORMATION: synthetic peptide

<400> SEQUENCE: 2

Leu Leu Arg Ile Ser Leu Leu Leu Ile Glu Ser Trp Leu Glu
1               5                   10

<210> SEQ ID NO 3
<211> LENGTH: 14
<212> TYPE: PRT

```
<213> ORGANISM: Artificial sequence
<220> FEATURE:
<223> OTHER INFORMATION: synthetic peptide

<400> SEQUENCE: 3

Phe Leu Ser Leu Ile Val Ser Ile Leu Arg Ser Trp Asn Glu
1               5                   10

<210> SEQ ID NO 4
<211> LENGTH: 17
<212> TYPE: PRT
<213> ORGANISM: Artificial sequence
<220> FEATURE:
<223> OTHER INFORMATION: synthetic peptide

<400> SEQUENCE: 4

Asp Ser Thr Lys Cys Gly Lys Leu Ile Cys Thr Gly Ile Ser Ser Ile
1               5                   10                  15

Pro

<210> SEQ ID NO 5
<211> LENGTH: 18
<212> TYPE: PRT
<213> ORGANISM: Artificial sequence
<220> FEATURE:
<223> OTHER INFORMATION: synthetic peptide

<400> SEQUENCE: 5

Ala Gly Ala Val Val Gly Gly Leu Gly Gly Tyr Met Leu Gly Ser Ala
1               5                   10                  15

Met Ser

<210> SEQ ID NO 6
<211> LENGTH: 14
<212> TYPE: PRT
<213> ORGANISM: Artificial sequence
<220> FEATURE:
<223> OTHER INFORMATION: synthetic peptide

<400> SEQUENCE: 6

Gly Ala Ile Ile Gly Leu Met Val Gly Gly Val Val Ile Ala
1               5                   10

<210> SEQ ID NO 7
<211> LENGTH: 12
<212> TYPE: PRT
<213> ORGANISM: Artificial sequence
<220> FEATURE:
<223> OTHER INFORMATION: synthetic peptide

<400> SEQUENCE: 7

Gly Val Phe Val Leu Gly Phe Leu Gly Phe Leu Ala
1               5                   10

<210> SEQ ID NO 8
<211> LENGTH: 15
<212> TYPE: PRT
<213> ORGANISM: Artificial sequence
<220> FEATURE:
<223> OTHER INFORMATION: synthetic peptide

<400> SEQUENCE: 8

Pro Leu Tyr His Leu Val Thr Glu Val Arg Gly Met Gln Glu Ala
1               5                   10                  15
```

```
<210> SEQ ID NO 9
<211> LENGTH: 15
<212> TYPE: PRT
<213> ORGANISM: Artificial sequence
<220> FEATURE:
<223> OTHER INFORMATION: synthetic peptide

<400> SEQUENCE: 9

Pro Gln His Tyr Leu Glu Thr Val Val Arg Gly Met Leu Glu Ala
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: synthetic peptide

<400> SEQUENCE: 10

Phe Asn Ser Leu Ile Ser Ser Ile Leu Arg Val Trp Leu Glu
1               5                   10

<210> SEQ ID NO 11
<211> LENGTH: 14
<212> TYPE: PRT
<213> ORGANISM: Artificial sequence
<220> FEATURE:
<223> OTHER INFORMATION: synthetic peptide

<400> SEQUENCE: 11

Leu Ser Gln Ile Leu Ser Ser Leu Ile Gln Ser Trp Leu Glu
1               5                   10

<210> SEQ ID NO 12
<211> LENGTH: 14
<212> TYPE: PRT
<213> ORGANISM: Artificial sequence
<220> FEATURE:
<223> OTHER INFORMATION: synthetic peptide

<400> SEQUENCE: 12

Leu Ser Gln Ile Leu Ser Ser Leu Ile Glu Ser Trp Leu Glu
1               5                   10

<210> SEQ ID NO 13
<211> LENGTH: 15
<212> TYPE: PRT
<213> ORGANISM: Artificial sequence
<220> FEATURE:
<223> OTHER INFORMATION: synthetic peptide

<400> SEQUENCE: 13

Ala Ser Leu Leu Ser Phe Met Gln Gly Tyr Met Lys His Ala Thr
1               5                   10                  15

<210> SEQ ID NO 14
<211> LENGTH: 199
<212> TYPE: PRT
<213> ORGANISM: Homo sapiens

<400> SEQUENCE: 14

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
                20                  25                  30

Ser Ser Glu Met Phe Ser Glu Phe Asp Lys Arg Tyr Thr His Gly Arg
```

-continued

```
                35                  40                  45
Gly Phe Ile Thr Lys Ala Ile Asn Ser Cys His Thr Ser Ser Leu Ala
         50                  55                  60
Thr Pro Glu Asp Lys Glu Gln Ala Gln Gln Met Asn Gln Lys Asp Phe
 65                  70                  75                  80
Leu Ser Leu Ile Val Ser Ile Leu Arg Ser Trp Asn Glu Pro Leu Tyr
                 85                  90                  95
His Leu Val Thr Glu Val Arg Gly Met Gln Glu Ala Pro Glu Ala Ile
                100                 105                 110
Leu Ser Lys Ala Val Glu Ile Glu Glu Gln Thr Lys Arg Leu Leu Glu
            115                 120                 125
Gly Met Glu Leu Ile Val Ser Gln Val His Pro Glu Thr Lys Glu Asn
130                 135                 140
Glu Ile Tyr Pro Val Trp Ser Gly Leu Pro Ser Leu Gln Met Ala Asp
145                 150                 155                 160
Glu Glu Ser Arg Leu Ser Ala Tyr Tyr Asn Leu Leu His Cys Leu Arg
                165                 170                 175
Arg Asp Ser His Lys Ile Asp Asn Tyr Leu Lys Leu Leu Lys Cys Arg
            180                 185                 190
Ile Ile His Asn Asn Asn Cys
        195

<210> SEQ ID NO 15
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 15
atttcatgat gaggtaccct cgagg                                          25

<210> SEQ ID NO 16
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 16
taaagtacta ctccatggga gctccctag                                      29

<210> SEQ ID NO 17
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 17
atttcatttc tgagcctgat agtcagcata ttgcgatcct ggaatgagtg ag            52

<210> SEQ ID NO 18
<211> LENGTH: 56
<212> TYPE: DNA
<213> ORGANISM: Artificial sequence
<220> FEATURE:
<223> OTHER INFORMATION: synthetic oligonucleotide

<400> SEQUENCE: 18
taaagtaaag actcggacta tcagtcgtat aacgctagga ccttactcac tcctag        56
```

<210> SEQ ID NO 19
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 19
atttcattta acagcctgat atccagcata ttgcgagtct ggcttgagtg ag            52

<210> SEQ ID NO 20
<211> LENGTH: 56
<212> TYPE: DNA
<213> ORGANISM: Artificial sequence
<220> FEATURE:
<223> OTHER INFORMATION: synthetic oligonucleotide

<400> SEQUENCE: 20
taaagtaaat tgtcggacta taggtcgtat aacgctcaga ccgaactcac tcctag        56

<210> SEQ ID NO 21
<211> LENGTH: 14
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: any amino acid forming a helix
<220> FEATURE:
<221> NAME/KEY: MISC_FEATURE
<222> LOCATION: (2)..(2)
<223> OTHER INFORMATION: Leu, Ile or Val
<220> FEATURE:
<221> NAME/KEY: MISC_FEATURE
<222> LOCATION: (3)..(3)
<223> OTHER INFORMATION: X= Arg, Lys, His, Ser or Thr
<220> FEATURE:
<221> NAME/KEY: MISC_FEATURE
<222> LOCATION: (4)..(4)
<223> OTHER INFORMATION: Ile, Leu or Val
<220> FEATURE:
<221> NAME/KEY: MISC_FEATURE
<222> LOCATION: (5)..(5)
<223> OTHER INFORMATION: any amino acid forming a helix
<220> FEATURE:
<221> NAME/KEY: MISC_FEATURE
<222> LOCATION: (6)..(6)
<223> OTHER INFORMATION: Leu, Ile or Val
<220> FEATURE:
<221> NAME/KEY: MISC_FEATURE
<222> LOCATION: (7)..(7)
<223> OTHER INFORMATION: Leu, Ile, Val, Ser or Thr
<220> FEATURE:
<221> NAME/KEY: MISC_FEATURE
<222> LOCATION: (8)..(8)
<223> OTHER INFORMATION: any amino acid forming a helix
<220> FEATURE:
<221> NAME/KEY: MISC_FEATURE
<222> LOCATION: (9)..(9)
<223> OTHER INFORMATION: any amino acid forming a helix
<220> FEATURE:
<221> NAME/KEY: MISC_FEATURE
<222> LOCATION: (10)..(10)
<223> OTHER INFORMATION: Gln, Glu, Asp, Arg, His, Lys or Asn
<220> FEATURE:
<221> NAME/KEY: MISC_FEATURE
<222> LOCATION: (11)..(11)
<223> OTHER INFORMATION: Ser or Thr
<220> FEATURE:
<221> NAME/KEY: MISC_FEATURE
<222> LOCATION: (12)..(12)

```
<223> OTHER INFORMATION: Trp, Tyr or Phe
<220> FEATURE:
<221> NAME/KEY: MISC_FEATURE
<222> LOCATION: (13)..(13)
<223> OTHER INFORMATION: Leu, Ile, Val, Asn or Gln
<220> FEATURE:
<221> NAME/KEY: MISC_FEATURE
<222> LOCATION: (14)..(14)
<223> OTHER INFORMATION: Glu, Gln, Asp or Asn

<400> SEQUENCE: 21

Xaa Xaa Xaa Xaa Xaa Xaa Xaa Xaa Xaa Xaa Xaa Xaa Xaa Xaa
1               5                   10

<210> SEQ ID NO 22
<211> LENGTH: 14
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: any amino acid forming a helix
<220> FEATURE:
<221> NAME/KEY: MISC_FEATURE
<222> LOCATION: (3)..(3)
<223> OTHER INFORMATION: Arg or Ser
<220> FEATURE:
<221> NAME/KEY: MISC_FEATURE
<222> LOCATION: (4)..(4)
<223> OTHER INFORMATION: Ile or Leu
<220> FEATURE:
<221> NAME/KEY: MISC_FEATURE
<222> LOCATION: (5)..(5)
<223> OTHER INFORMATION: any amino acid forming a helix
<220> FEATURE:
<221> NAME/KEY: MISC_FEATURE
<222> LOCATION: (6)..(6)
<223> OTHER INFORMATION: Leu or Val
<220> FEATURE:
<221> NAME/KEY: MISC_FEATURE
<222> LOCATION: (7)..(7)
<223> OTHER INFORMATION: Leu or Ser
<220> FEATURE:
<221> NAME/KEY: MISC_FEATURE
<222> LOCATION: (8)..(8)
<223> OTHER INFORMATION: any amino acid forming a helix
<220> FEATURE:
<221> NAME/KEY: MISC_FEATURE
<222> LOCATION: (9)..(9)
<223> OTHER INFORMATION: any amino acid forming a helix
<220> FEATURE:
<221> NAME/KEY: MISC_FEATURE
<222> LOCATION: (10)..(10)
<223> OTHER INFORMATION: Gln, Glu or Arg
<220> FEATURE:
<221> NAME/KEY: MISC_FEATURE
<222> LOCATION: (13)..()
<223> OTHER INFORMATION: Leu or Asn
<220> FEATURE:
<221> NAME/KEY: MISC_FEATURE
<222> LOCATION: (13)..(13)
<223> OTHER INFORMATION: Leu or Asn

<400> SEQUENCE: 22

Xaa Leu Xaa Xaa Xaa Xaa Xaa Xaa Xaa Xaa Ser Trp Xaa Glu
1               5                   10

<210> SEQ ID NO 23
<211> LENGTH: 14
<212> TYPE: PRT
<213> ORGANISM: Artificial sequence
<220> FEATURE:
<223> OTHER INFORMATION: synthetic peptide
```

```
<220> FEATURE:
<221> NAME/KEY: MISC_FEATURE
<222> LOCATION: (1)..(1)
<223> OTHER INFORMATION: Leu or Phe
<220> FEATURE:
<221> NAME/KEY: MISC_FEATURE
<222> LOCATION: (3)..(3)
<223> OTHER INFORMATION: Arg or Ser
<220> FEATURE:
<221> NAME/KEY: MISC_FEATURE
<222> LOCATION: (4)..(4)
<223> OTHER INFORMATION: Ile or Leu
<220> FEATURE:
<221> NAME/KEY: MISC_FEATURE
<222> LOCATION: (5)..(5)
<223> OTHER INFORMATION: Ser or Ile
<220> FEATURE:
<221> NAME/KEY: MISC_FEATURE
<222> LOCATION: (6)..(6)
<223> OTHER INFORMATION: Leu or Val
<220> FEATURE:
<221> NAME/KEY: MISC_FEATURE
<222> LOCATION: (7)..(7)
<223> OTHER INFORMATION: Leu or Ser
<220> FEATURE:
<221> NAME/KEY: MISC_FEATURE
<222> LOCATION: (8)..(8)
<223> OTHER INFORMATION: Leu or Ile
<220> FEATURE:
<221> NAME/KEY: MISC_FEATURE
<222> LOCATION: (9)..(9)
<223> OTHER INFORMATION: Ile or Leu
<220> FEATURE:
<221> NAME/KEY: MISC_FEATURE
<222> LOCATION: (10)..(10)
<223> OTHER INFORMATION: Gln, Glu or Arg
<220> FEATURE:
<221> NAME/KEY: MISC_FEATURE
<222> LOCATION: (13)..(13)
<223> OTHER INFORMATION: Leu or Asn

<400> SEQUENCE: 23

Xaa Leu Xaa Xaa Xaa Xaa Xaa Xaa Xaa Ser Trp Xaa Glu
1               5                   10

<210> SEQ ID NO 24
<211> LENGTH: 12
<212> TYPE: PRT
<213> ORGANISM: Artificial sequence
<220> FEATURE:
<223> OTHER INFORMATION: synthetic peptide

<400> SEQUENCE: 24

Gly Ala Ile Ile Gly Leu Met Val Gly Gly Val Val
1               5                   10

<210> SEQ ID NO 25
<211> LENGTH: 12
<212> TYPE: PRT
<213> ORGANISM: Artificial sequence
<220> FEATURE:
<223> OTHER INFORMATION: synthetic peptide

<400> SEQUENCE: 25

Ala Val Gly Ile Gly Ala Leu Phe Leu Gly Phe Leu
1               5                   10

<210> SEQ ID NO 26
<211> LENGTH: 21
<212> TYPE: PRT
<213> ORGANISM: Artificial sequence
<220> FEATURE:
<223> OTHER INFORMATION: synthetic peptide
```

```
<400> SEQUENCE: 26

Lys Thr Asn Met Lys His Met Ala Gly Ala Ala Ala Gly Ala Val
1               5                   10                  15

Val Gly Gly Leu Gly
            20

<210> SEQ ID NO 27
<211> LENGTH: 12
<212> TYPE: PRT
<213> ORGANISM: Artificial sequence
<220> FEATURE:
<223> OTHER INFORMATION: synthetic peptide

<400> SEQUENCE: 27

Phe Ala Gly Val Val Leu Ala Gly Ala Ala Leu Gly
1               5                   10

<210> SEQ ID NO 28
<211> LENGTH: 18
<212> TYPE: PRT
<213> ORGANISM: Artificial sequence
<220> FEATURE:
<223> OTHER INFORMATION: synthetic peptide

<400> SEQUENCE: 28

Phe Ile Gly Ala Ile Ile Gly Ser Val Ala Leu Gly Val Ala Thr Ala
1               5                   10                  15

Ala Gly

<210> SEQ ID NO 29
<211> LENGTH: 17
<212> TYPE: PRT
<213> ORGANISM: Artificial sequence
<220> FEATURE:
<223> OTHER INFORMATION: synthetic peptide

<400> SEQUENCE: 29

Phe Leu Gly Phe Leu Leu Gly Val Gly Ser Ala Ile Ala Ser Gly Val
1               5                   10                  15

Ala

<210> SEQ ID NO 30
<211> LENGTH: 17
<212> TYPE: PRT
<213> ORGANISM: Artificial sequence
<220> FEATURE:
<223> OTHER INFORMATION: synthetic peptide

<400> SEQUENCE: 30

Phe Phe Gly Ala Val Ile Gly Thr Ile Ala Leu Gly Val Ala Thr Ser
1               5                   10                  15

Ala

<210> SEQ ID NO 31
<211> LENGTH: 12
<212> TYPE: PRT
<213> ORGANISM: Artificial sequence
<220> FEATURE:
<223> OTHER INFORMATION: synthetic peptide

<400> SEQUENCE: 31

Ser Pro Val Ala Ala Leu Thr Leu Gly Leu Ala Leu
1               5                   10
```

<210> SEQ ID NO 32
<211> LENGTH: 17
<212> TYPE: PRT
<213> ORGANISM: Artificial sequence
<220> FEATURE:
<223> OTHER INFORMATION: synthetic peptide

<400> SEQUENCE: 32

Gly Pro Val Ser Leu Thr Leu Ala Leu Leu Leu Gly Gly Leu Thr Met
1               5                   10                  15

Gly

<210> SEQ ID NO 33
<211> LENGTH: 17
<212> TYPE: PRT
<213> ORGANISM: Artificial sequence
<220> FEATURE:
<223> OTHER INFORMATION: synthetic peptide

<400> SEQUENCE: 33

Gly Ala Ala Ile Gly Leu Ala Trp Ile Pro Tyr Phe Gly Pro Ala Ala
1               5                   10                  15

Glu

<210> SEQ ID NO 34
<211> LENGTH: 19
<212> TYPE: PRT
<213> ORGANISM: Artificial sequence
<220> FEATURE:
<223> OTHER INFORMATION: synthetic peptide

<400> SEQUENCE: 34

Met Leu Leu Gln Ala Phe Leu Phe Leu Leu Ala Gly Phe Ala Ala Lys
1               5                   10                  15

Ile Ser Ala

<210> SEQ ID NO 35
<211> LENGTH: 12
<212> TYPE: PRT
<213> ORGANISM: Artificial sequence
<220> FEATURE:
<223> OTHER INFORMATION: synthetic peptide

<400> SEQUENCE: 35

Arg Pro Ala Leu Leu Ala Leu Leu Ala Leu Pro Ala
1               5                   10

<210> SEQ ID NO 36
<211> LENGTH: 16
<212> TYPE: PRT
<213> ORGANISM: Artificial sequence
<220> FEATURE:
<223> OTHER INFORMATION: synthetic peptide

<400> SEQUENCE: 36

Val Thr Val Val Leu Trp Ser Ala Tyr Pro Val Val Trp Leu Ile Gly
1               5                   10                  15

<210> SEQ ID NO 37
<211> LENGTH: 18
<212> TYPE: PRT
<213> ORGANISM: Artificial sequence
<220> FEATURE:
<223> OTHER INFORMATION: synthetic peptide

```
<400> SEQUENCE: 37

Gly Ala Gly Ile Val Pro Leu Asn Ile Glu Thr Leu Leu Phe Met Val
1               5                   10                  15
Leu Asp

<210> SEQ ID NO 38
<211> LENGTH: 18
<212> TYPE: PRT
<213> ORGANISM: Artificial sequence
<220> FEATURE:
<223> OTHER INFORMATION: synthetic peptide

<400> SEQUENCE: 38

Ile Lys Lys Ala Gly Thr Glu Leu Val Asn Phe Leu Ser Tyr Phe Val
1               5                   10                  15
Glu Leu

<210> SEQ ID NO 39
<211> LENGTH: 15
<212> TYPE: PRT
<213> ORGANISM: Artificial sequence
<220> FEATURE:
<223> OTHER INFORMATION: synthetic peptide

<400> SEQUENCE: 39

Ala Ser Leu Leu Ser Phe Met Gln Gly Tyr Met Lys His Ala Thr
1               5                   10                  15

<210> SEQ ID NO 40
<211> LENGTH: 16
<212> TYPE: PRT
<213> ORGANISM: Artificial sequence
<220> FEATURE:
<223> OTHER INFORMATION: synthetic peptide

<400> SEQUENCE: 40

Phe Gly Phe Pro Glu His Leu Leu Val Asp Phe Leu Gln Ser Leu Ser
1               5                   10                  15

<210> SEQ ID NO 41
<211> LENGTH: 13
<212> TYPE: PRT
<213> ORGANISM: Artificial sequence
<220> FEATURE:
<223> OTHER INFORMATION: synthetic peptide

<400> SEQUENCE: 41

Asp Phe Phe Thr Ile Trp Leu Asp Leu Asn Met Phe Leu
1               5                   10

<210> SEQ ID NO 42
<211> LENGTH: 13
<212> TYPE: PRT
<213> ORGANISM: Artificial sequence
<220> FEATURE:
<223> OTHER INFORMATION: synthetic peptide

<400> SEQUENCE: 42

Phe Leu Glu Leu Tyr Arg His Ile Ala Gln His Gly Phe
1               5                   10

<210> SEQ ID NO 43
<211> LENGTH: 13
<212> TYPE: PRT
```

```
<213> ORGANISM: Artificial sequence
<220> FEATURE:
<223> OTHER INFORMATION: synthetic peptide

<400> SEQUENCE: 43

Ile Gly Glu Ala Ile Arg Val Ile Ala Glu Arg Gly Leu
1               5                   10

<210> SEQ ID NO 44
<211> LENGTH: 20
<212> TYPE: PRT
<213> ORGANISM: Artificial sequence
<220> FEATURE:
<223> OTHER INFORMATION: synthetic peptide

<400> SEQUENCE: 44

Gly Leu Phe Gly Ala Ile Ala Gly Phe Ile Glu Asn Gly Trp Glu Gly
1               5                   10                  15

Met Ile Asp Gly
            20

<210> SEQ ID NO 45
<211> LENGTH: 16
<212> TYPE: PRT
<213> ORGANISM: Artificial sequence
<220> FEATURE:
<223> OTHER INFORMATION: synthetic peptide

<400> SEQUENCE: 45

Met Glu Asn Ile Thr Ser Gly Phe Leu Gly Pro Leu Leu Val Leu Gln
1               5                   10                  15

<210> SEQ ID NO 46
<211> LENGTH: 13
<212> TYPE: PRT
<213> ORGANISM: Artificial sequence
<220> FEATURE:
<223> OTHER INFORMATION: synthetic peptide

<400> SEQUENCE: 46

Thr Glu Leu Val Asn Phe Leu Ser Tyr Phe Val Glu Leu
1               5                   10

<210> SEQ ID NO 47
<211> LENGTH: 14
<212> TYPE: PRT
<213> ORGANISM: Artificial sequence
<220> FEATURE:
<223> OTHER INFORMATION: synthetic peptide

<400> SEQUENCE: 47

Val Ile Gly Thr Asn Ala Val Ser Ile Glu Thr Asn Ile Glu
1               5                   10

<210> SEQ ID NO 48
<211> LENGTH: 17
<212> TYPE: PRT
<213> ORGANISM: Artificial sequence
<220> FEATURE:
<223> OTHER INFORMATION: synthetic peptide

<400> SEQUENCE: 48

Asp Ser Thr Lys Cys Gly Lys Leu Ile Cys Thr Gly Ile Ser Ser Ile
1               5                   10                  15

Pro
```

```
<210> SEQ ID NO 49
<211> LENGTH: 15
<212> TYPE: PRT
<213> ORGANISM: Artificial sequence
<220> FEATURE:
<223> OTHER INFORMATION: synthetic peptide

<400> SEQUENCE: 49

Ala Ser Leu Leu Ser Phe Met Gln Gly Tyr Met Lys His Ala Thr
1               5                   10                  15
```